(12) United States Patent
Doty

(10) Patent No.: US 7,361,192 B2
(45) Date of Patent: Apr. 22, 2008

(54) SPINAL DISC PROSTHESIS AND METHODS OF USE

(76) Inventor: Keith L. Doty, 316 NW. 17th St., Gainesville, FL (US) 32603-1615

( * ) Notice: Subject to any disclaimer, the term of this patent is extended or adjusted under 35 U.S.C. 154(b) by 301 days.

(21) Appl. No.: 11/112,832

(22) Filed: Apr. 22, 2005

(65) Prior Publication Data

US 2006/0241767 A1 Oct. 26, 2006

(51) Int. Cl.
*A61F 2/44* (2006.01)
(52) U.S. Cl. ............... 623/17.12; 623/17.11; 623/17.13; 623/17.14; 623/17.15; 623/17.16
(58) Field of Classification Search .. 623/17.11–17.16; 606/61; 403/53, 63
See application file for complete search history.

(56) References Cited

U.S. PATENT DOCUMENTS

| 4,309,777 A | 1/1982 | Patil |
| 4,349,921 A | 9/1982 | Kuntz |
| 4,595,663 A | 6/1986 | Krohn et al. |
| RE32,449 E | 6/1987 | Clausen et al. |
| 4,714,469 A | 12/1987 | Kenna |
| 4,759,766 A | 7/1988 | Buettner-Jantz et al. |
| 4,759,769 A | 7/1988 | Hedman et al. |
| 4,846,840 A | 7/1989 | Leclerq et al. |
| 4,863,476 A | 9/1989 | Shepperd |
| 4,911,718 A | 3/1990 | Lee et al. |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,997,432 A | 3/1991 | Keller |
| 5,002,576 A | 3/1991 | Furhmann et al. |
| 5,024,670 A | 6/1991 | Smith et al. |
| 5,037,438 A | 8/1991 | Davidson |
| 5,047,055 A | 9/1991 | Bao et al. |
| 5,071,437 A | 12/1991 | Steffee |
| 5,080,675 A | 1/1992 | Lawes et al. |
| 5,258,031 A | 11/1993 | Salib et al. |
| 5,258,043 A | 11/1993 | Stone |
| 5,306,307 A | 4/1994 | Senter et al. |

(Continued)

FOREIGN PATENT DOCUMENTS

DE 2263842 7/1974

(Continued)

OTHER PUBLICATIONS

Bao, Q.-B. et al. "Artificial Disc Technology" *Neurosurg Focus*, 2000, vol. 9, No. 4.

(Continued)

*Primary Examiner*—Eduardo C. Robert
*Assistant Examiner*—Andrew Yang
(74) *Attorney, Agent, or Firm*—Saliwanchik, Lloyd & Saliwanchik

(57) ABSTRACT

The subject invention provides a modular six-degrees-of-freedom spatial mechanism for spinal disc prosthesis, with three rotational and three translational degrees-of-freedom within the entire workspace of a Functional Spinal Unit (FSU). The prosthetic disc mechanism attaches to upper and lower plates anchored between vertebrae of an FSU. Scaling, conjoined with motion limit stops, allows the device to realize almost any nominal spinal articulation, from the cervical to lumbar regions.

54 Claims, 27 Drawing Sheets

U.S. PATENT DOCUMENTS

| | | | |
|---|---|---|---|
| 5,306,308 A | 4/1994 | Gorss et al. | |
| 5,306,309 A | 4/1994 | Wagner et al. | |
| 5,308,412 A | 5/1994 | Shetty et al. | |
| 5,314,477 A | 5/1994 | Marnay | |
| 5,314,478 A | 5/1994 | Oka et al. | |
| 5,320,644 A | 6/1994 | Baumgartner | |
| 5,401,269 A | 3/1995 | Buettner-Jantz et al. | |
| 5,415,704 A | 5/1995 | Davidson | |
| 5,425,773 A | 6/1995 | Boyd et al. | |
| 5,458,642 A | 10/1995 | Beer et al. | |
| 5,562,738 A | 10/1996 | Boyd et al. | |
| 5,674,296 A | 10/1997 | Bryan et al. | |
| 5,676,701 A | 10/1997 | Yuan et al. | |
| 5,782,832 A | 7/1998 | Larsen et al. | |
| 5,827,328 A | 10/1998 | Buttermann | |
| 5,865,846 A | 2/1999 | Bryan et al. | |
| 6,001,130 A | 12/1999 | Bryan et al. | |
| 6,019,792 A | 2/2000 | Cauthen | |
| 6,136,031 A | 10/2000 | Middleton | |
| 6,156,067 A | 12/2000 | Bryan et al. | |
| 6,179,874 B1 | 1/2001 | Cauthen | |
| 6,296,664 B1 | 10/2001 | Middleton | |
| 6,315,797 B1 | 11/2001 | Middleton | |
| 6,348,071 B1 | 2/2002 | Steffee et al. | |
| 6,368,350 B1 | 4/2002 | Erickson et al. | |
| 6,395,032 B1 | 5/2002 | Gauchet | |
| 6,419,706 B1 | 7/2002 | Graf | |
| 6,458,159 B1 | 10/2002 | Thalgott | |
| 6,520,996 B1 | 2/2003 | Manasas et al. | |
| 6,572,653 B1 | 6/2003 | Simonson | |
| 6,579,321 B1 | 6/2003 | Gordon et al. | |
| 6,626,943 B2 | 9/2003 | Eberlein et al. | |
| 6,645,248 B2 | 11/2003 | Casutt | |
| 6,656,224 B2 | 12/2003 | Middleton | |
| 6,669,732 B2 | 12/2003 | Serhan et al. | |
| 6,733,532 B1 | 5/2004 | Gauchet et al. | |
| 6,736,850 B2 | 5/2004 | Davis | |
| 6,749,635 B1 | 6/2004 | Bryan | |
| 6,770,095 B2 | 8/2004 | Grinberg et al. | |
| 6,802,867 B2 | 10/2004 | Manasas et al. | |
| 6,960,232 B2 | 11/2005 | Lyons et al. | |
| 6,966,929 B2 | 11/2005 | Mitchell | |
| 7,022,138 B2 * | 4/2006 | Mashburn | 623/17.13 |
| 2004/0167626 A1 * | 8/2004 | Geremakis et al. | 623/17.15 |
| 2005/0273169 A1 * | 12/2005 | Purcell | 623/17.12 |
| 2006/0235525 A1 * | 10/2006 | Gil et al. | 623/17.13 |

FOREIGN PATENT DOCUMENTS

| | | |
|---|---|---|
| DE | 3023353 | 4/1981 |
| EP | 0042271 | 12/1981 |
| EP | 0176728 | 4/1986 |
| EP | 2718635 | 10/1995 |
| EP | 0699426 | 3/1996 |
| SU | 1225561 | 4/1986 |
| WO | WO 91/13598 | 9/1991 |
| WO | WO 92/14423 | 9/1992 |
| WO | WO 93/10725 | 6/1993 |
| WO | WO 94/04100 | 3/1994 |
| WO | WO 98/14142 | 4/1998 |

OTHER PUBLICATIONS

Bao, Q.-B. et al. "The Artificial Disc: Theory, Design and Materials" *Biomaterials*, 1996, pp. 1157-1167, vol. 17, No. 12.

Bogduk, N. et al. "Biomechanics of the Cervical Spine. I: Normal Kinematics" *Clinical Biomechanics*, 2000, pp. 633-648, vol. 15.

Bogduk, N. et al. "A Biological Basis for Instataneous Centres of Rotation of the Vertebral Column" *Proc. Instn. Mech. Engrs.*, 1995, pp. 177-183, vol. 209.

Mameren, H. van et al. "Cervical Spine Motion in the Sagittal Plane II: Position of Segmental Averaged Instantaneous Centers of Rotation—A Cineradiographic Study" *Spine*, 1992, pp. 467-474, vol. 17, No. 5.

Panjabi, M. M. "Point of View: Instantaneous Center of Rotation and Instability of the Cervical Spine" *Spine*, 1997, pp. 647-648, vol. 22.

Panjabi, M. M. et al. "Articular Facets of the Human Spine: Quantitative Three-Dimensional Anatomy" *Spine*, 1993, pp. 1298-1310, vol. 18, No. 10.

Yoganandan, N, Maiman DJ, Pintar FA: Biomechanics of the cervical spine. In Principles of Spinal Surgery, Menezes AH, Sonntag VKH (ed), McGraw-Hill, 1996. Chapter 5, pp. 69-83.

Bogdun, N, et al. "Clinical Anatomy of the Lumbar Spine, "ISBN 0-443-03505-9, Churchill-Livingstone Melbourne Edinburgh London New York, 1987.

Buttner-Jantz K., et a. "The Artificial Disc", ISBN 3-540-41779-6, Springer-Verlag, Berlin Heidelberg New York, 2003.

Mow, V.C. and Hayes, W.C. "Basic Orthopaedic Biomechanics", $2^{nd}$ Edition, Lippincott-Raven Publ., NY, 1997.

Herman, A.M. et al. "A new Computer-Aided Technique for Analysis of Lateral Cervical Radiographs in Post-Operative Patients with Degenerative Disease" Cervical Spine Research Society, $13^{th}$ Annual Meeting, Dec. 5-7, 2002, Miami Beach, FL.

Margulies, J.Y. and Adler, R.L., "Geometry of Scoliotic Space Curves" Biotechnologies for Spinal Surgery Meeting, Apr. 11-13, 2002, Halle, Germany (Abstract).

Zigler, Jack, "Lumbar Artificial Disc Surgery for Chronic Back Pain", 2004, pp. 1-24 found at www.spine-health.com/research/discupdate/artificial/artificial01.html.

* cited by examiner

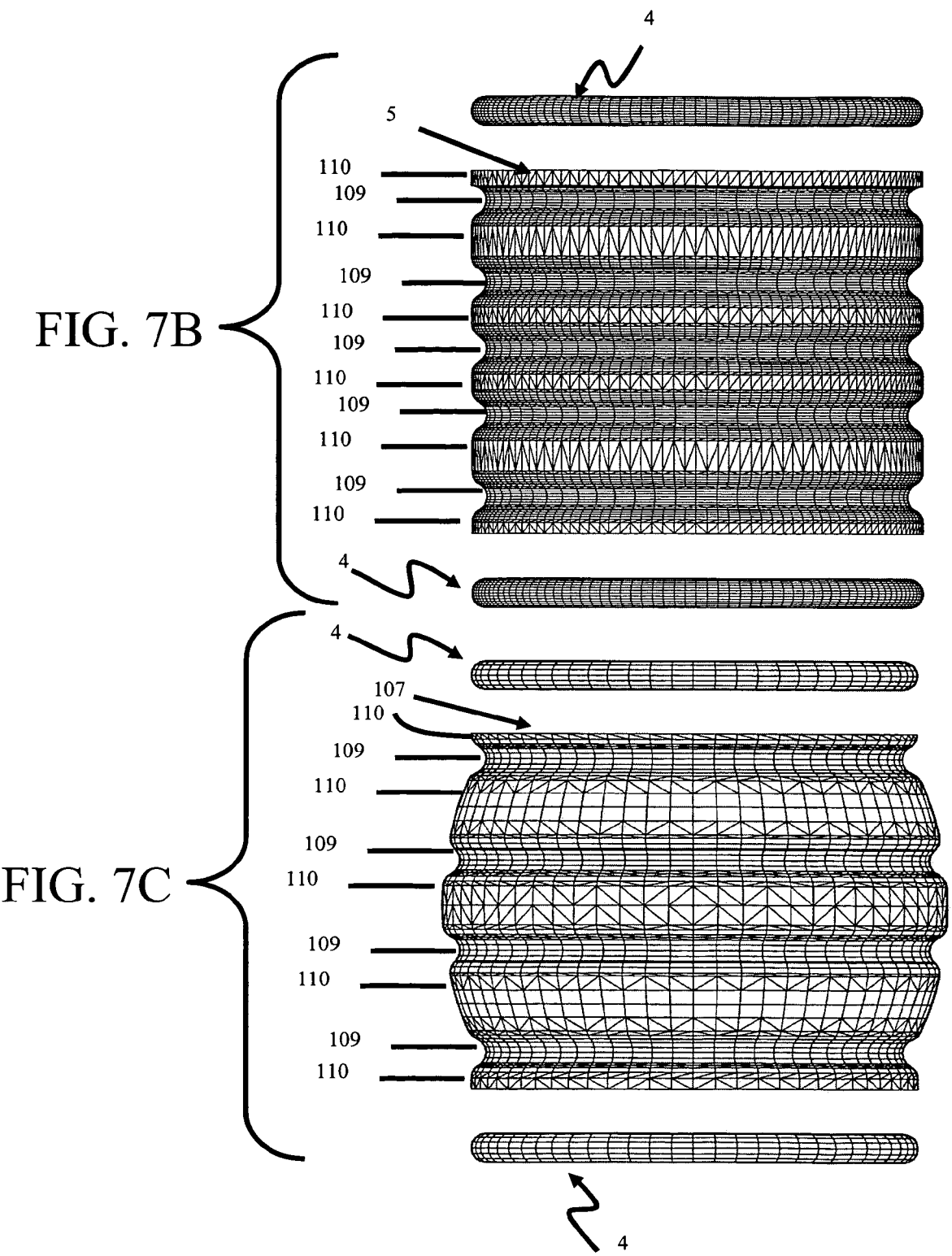

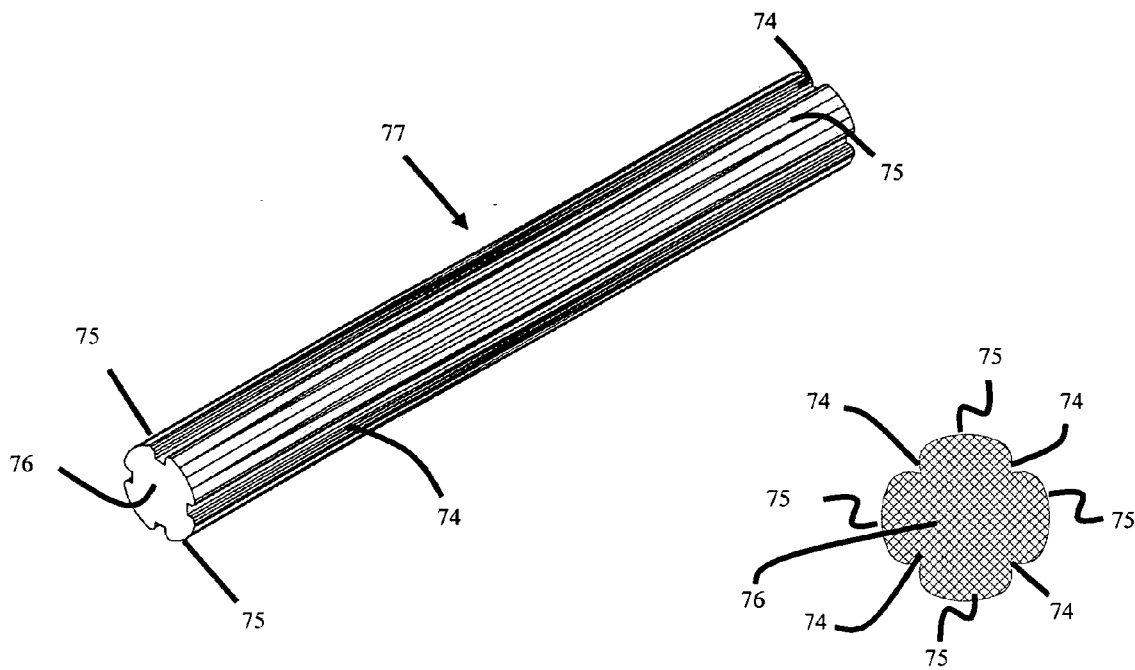
FIG. 23A
FIG. 23B
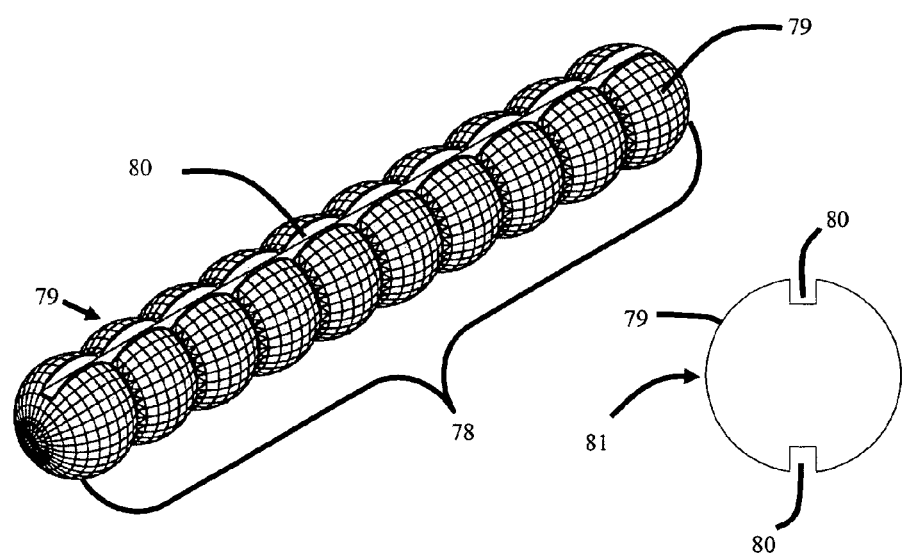
FIG. 24A
FIG. 24B

SPINAL DISC PROSTHESIS AND METHODS OF USE

BACKGROUND OF INVENTION

Spinal disc herniation, a common ailment, often induces pain, as well as neurologically and physiologically debilitating processes for which relief becomes paramount. If conservative treatments fail, the more drastic measures of discectomies and spinal fusion may be indicated. The latter treatment, while providing short term relief, often leads to excessive forces on facet joints adjacent to the fusion and creates further problems over time. Drastic treatments are usually unable to restore normal disc function. The loss of disc function has led to a number of disc prosthesis that attempt to provide natural motion.

The literature documents that the Instantaneous Axis of Rotation (IAR) during sagittal rotation of the superior vertebra with respect to the inferior vertebra of a Functional Spinal Unit (FSU) in the cervical spine moves significant distances during flexion and extension of the spine (Mameren H. van, Sanches H., Beursgens J., Drukker, J., "Cervical Spine Motion in the Sagittal Plane II: Position of Segmental Averaged Instantaneous Centers of Rotation-A Cineradiographic Study", *Spine* 1992, Vol.17, No.5, pp. 467-474). This motion varies widely between functional spinal units on an individual spine and between individuals and depends on age, time-of-day, and the general health and condition of the intervertebral discs, facet joints and other components of the FSU and spine. A moving IAR means that the superior vertebra both rotates and translates while moving with respect to the inferior vertebra of an FSU. Natural spinal motions place severe requirements on the design of a prosthetic disc; simple rotational joints are not able meet those requirements.

In addition, motion coupling between axial and lateral bending and other functional spinal units involved in the overall spinal motion increases the complexity and difficulty in developing a prosthetic disc replacement that realizes natural spinal motion. The complex facet surfaces in an FSU significantly influence and constrain sagittal, lateral and axial motions. The orientation of these facet surfaces vary with FSU location in the spine and induce wide variations in motion parameters and constraints. The complex motion of a superior vertebra with respect to the associated inferior vertebra of an FSU, certainly in the cervical spine, cannot be realized by a simple rotation or simple translation, or even a combination of rotation and translation along a fixed axis, and still maintain the integrity and stability of the FSU and facet joints.

One advantage of a general motion spatial mechanism as a disc prosthesis, as described in this application, is that it solves the complex, challenging motion problem posed by nature for disc prosthesis and offers a scalable mechanism for disc replacement without loss of general motion capabilities in the FSU.

Researchers have attempted to design a successful intervertebral disc for years. Salib et al., U.S. Pat. No. 5,258,031; Marnay, U.S. Pat. No. 5,314,477; Boyd et al., U.S. Pat. No. 5,425,773; Yuan et al., U.S. Pat. No. 5,676,701; and Larsen et al., U.S. Pat. No. 5,782,832 all use ball-and-socket arrangements fixed to the superior and inferior plates rigidly attached to the vertebrae of an FSU. However, these designs limit motion to rotation only about the socket when the two plates are in contact. As the literature points out (Bogduk N. and Mercer S., "Biomechanics of the cervical spine. I: Normal kinematics", *Clinical Biomechanics, Elsevier*, 15(2000) 633-648; and Mameren H. van, Sanches H., Beursgens J., Drukker, J., "Cervical Spine Motion in the Sagittal Plane II: Position of Segmental Averaged Instantaneous Centers of Rotation-A Cineradiographic Study", Spine 1992, Vol. 17, No. 5, pp. 467-474), this restricted motion does not correspond to the natural motion of the vertebrae, even for sagittal plane motion, much less for combined sagittal, lateral and axial motion. Further, when the two plates, as described in the cited patents, are not in contact, the devices are unable to provide stability to the intervertebral interface, which can allow free motion and lead to disc related spondylolisthesis, FSU instability and excessive facet loading.

As a further elaboration on the many ball-and-socket configurations, consider Salib et. al. (U.S. Pat. No. 5,258,031) as an example of previous efforts to address this problem. The Salib ball-and-socket arrangement only provides 3 independent axes of rotation and no translation when engaged.

During complex motions of an FSU, the superior vertebra, in general, requires translation along three independent directions. A sliding ovate structure in an oversized socket cannot perform such general translation motions, either, as it must engage in a trajectory dictated by its socket's geometrical surface and does not change the deleterious effects that may occur on the facet joints of the unit. The current invention overcomes these deficiencies of prior art devices by providing a full 6 degrees-of-freedom throughout the motion space of the FSU. In a preferred embodiment, the subject invention is also able to provide shock absorption, static compression and extension load bearing, as well as some torsion load bearing from a strong, flexible, corrugated boot covering.

The Cauthen rocker arm device (U.S. Pat. Nos. 6,019,792 and 6,179,874) appears to have similar motion and instability limitations as do the freely moving sliding disc cores found in the Bryan et al. patents (U.S. Pat. Nos. 5,674,296; 5,865,846; 6,001,130; and 6,156,067) and the SB Charité™ prosthesis, as described by Búttner-Jantz K., Hochschuler S. H., McAfee P. C. (Eds), *The Artificial Disc*, ISBN 3-540-41779-6 Springer-Verlag, Berlin Heidelberg New York, 2003; and U.S. Pat. No. 5,401,269; and Buettner-Jantz et al. U.S. Pat. No. 4,759,766) devices. In addition, the sliding disc core devices of the Bryan et al. and SB Charité™ devices do not permit natural motion of the joint for any fixed shape of the core.

When the FSU extends, the prosthesis's sliding core, in some cases, generates unnatural constraining forces on the FSU by restricting closure of the posterior intervertebral gap in the FSU. In any case, the core does not mechanically link the upper and lower plates of the prosthesis and has no means of maintaining the intervertebral gap throughout the range of motion. Such conditions inevitably contribute to prosthetic disc spondylolisthesis. In general, unconstrained or over-constrained relative motion between the two vertebral plates in a prosthetic disc contributes to FSU instability over time.

Further, current prosthetic disc technology is able only to minimally and rigidly support static loading. For example, load bearing and shock absorption in the SB Charité™ design and others (e.g. Bryan et al., U.S. Pat. No. 5,865,846) rely on the mechanical properties of the resilient, ultra-high-molecular-weight polyethylene core to provide both strength and static and dynamic loading. The rigidity of the sliding core appears to offer little energy absorption and flexibility to meet the intervertebral gap requirements during motion, and most likely generates excessive reaction forces on the spine during flexion, forces that potentially produce extra stress on facet joints and effect mobility.

With respect to the lower vertebra in an FSU, all possible, natural loci of motion of any four non-planar, non-collinear points located in the superior vertebra define the natural workspace of the FSU. This workspace varies from FSU to FSU on the spine, creating considerable spinal disc prosthesis design problems.

The FSU workspace boundary is dictated by the sagittal, lateral and axial angle limits reported in the literature (Mow V. C. and Hayes W. C., *Basic Orthopaedic Biomechanics*, Lippincott-Raven Pub., N.Y., $2^{nd}$ Addition, 1997). However, these angle limits do not reveal the underlying complex motion between two vertebrae in an FSU. The study by Mameren H. van, Sanches H., Beursgens J., Drukker, J., "Cervical Spine Motion in the Sagittal Plane II: Position of Segmental Averaged Instantaneous Centers of Rotation-A Cineradiographic Study", Spine 1992, Vol. 17, No. 5, pp. 467-474 demonstrates this complexity in the cervical spine, even when the motion is restricted to flexion and extension. The subject invention is able to accommodate a broader range of motions, since it moves freely with 6-DOF within the angle limits reported for all axes.

BRIEF SUMMARY

The subject invention provides a spinal disc prosthesis capable of providing spatial movement with up to 6 degrees of freedom. In a preferred embodiment, the device of the subject invention facilitates sagital, lateral, and polar vertebral movement when utilized in the spine of an animal. In one embodiment, the modular spinal disc prosthesis of the subject invention comprises superior and inferior vertebral plates, as well as a flexible, boot-protected replaceable 6-DOF modular prosthetic disc mechanism (linkage). The up to 6 degrees of freedom provided by the subject invention are provided by means of up to 3 independent rotational degrees of freedom and by means of up to 3 independent linear degrees of freedom. Said rotational degrees of freedom can be provided by means of a ball and socket joint, a cylinder and socket joint, a piston and socket joint, a universal (or Hooke) joint, or variations thereof. In a preferred embodiment, the modular prosthetic disc mechanism of the subject invention can comprise three orthogonal prismatic joints for general positioning in three-dimensional space and a spherical joint for three-dimensional orienting.

In a further preferred embodiment, the subject invention comprises a socket-base for containing a chambered-ball such that the chambered-ball is capable of rotating within the socket-base, providing 3-DOF for orienting the superior vertebral plate with the inferior vertebral plate. The chambered-ball itself possesses a cavity for containing a piston. The piston is slidably fixed within the cavity of the chambered-ball such that the piston is capable of sliding to and fro in the chambered-ball cavity.

The piston possesses a cavity for containing a spring or similar device or material to absorb shocks and excessive loads on the disc prosthesis. The spring is fixedly attached at one end at or near the floor of the chambered-ball and extends within the cavity of the chambered-ball such that the piston, inserted into the cavity of the chambered-ball, is able to rest on top of the opposite end of the spring or similar device. The combined piston and chambered-ball joint constitutes a polar-axis prismatic joint. The piston slides in and out of the chambered-ball cavity along the piston centerline, which also coincides with the polar-axis of the chambered-ball. The piston and chambered-ball unit thereby function as a telescoping joint. Loads placed on the top piston are absorbed by the spring or similar device as the piston is recessed into the chambered-ball cavity.

In yet a further preferred embodiment, a dual-track, orthogonal linear bearing is fixedly attached to the distal end of the piston. This linear bearing is slidably attached to a further element of the device referred to as a plane-bearing guide to create yet a further kinematically connected element of the device of the subject invention. The plane-bearing guide has two linear raceways, sagital-oriented and lateral-oriented, on opposite sides, which are perpendicular to each other. The linear bearing on the piston is slidably affixed within the sagital-oriented raceway. When positioned within a spine, the combined piston and plane-bearing guide allows movement of the functional spinal unit (FSU) along the raceway within the plane described by the polar axis and the line of action of this joint. This joint is called the sagittal prismatic joint since the aforementioned plane which moves about in space, is the sagittal plane for pure flexion of the spine.

In still a further preferred embodiment, additional dual-track, orthogonal linear bearings, located on a part of the device referred to as a cap-plate, are slidably affixed within the lateral-raceways on the plane-bearing guide. When positioned within a spine, the combined cap-plate and plane-bearing guide allows movement of the FSU along the raceway within the plane described by the polar axis and the line of action of this joint. This joint is called the lateral prismatic joint. The aforementioned plane moves about in space, but is the frontal plane for pure lateral bending.

Thus, the plane-bearing guide element provides two prismatic joints: the cap-plate and the plane-bearing guide for the lateral prismatic joint, and the plane-bearing guide and the piston for the sagittal prismatic joint. Together, the prismatic joints provide two orthogonal degrees-of-freedom.

In a preferred embodiment, ball-bearings are utilized in combination with the sagittal and lateral prismatic joint raceways. Ball-bearings are able to provide smooth movement and reduced friction between the elements of the prismatic joints. Alternative embodiments utilize bearing stops to limit movement within one or more of the prismatic joints. In another embodiment, the sagittal and lateral prismatic joints use surface bearings dictated by the geometry of the lower pair forming the joint.

In a preferred embodiment, a flexible boot surrounds the functional elements of the prosthetic device. In a further preferred embodiment, the boot is wrapped around the prosthetic device and clamped, or otherwise connected, to the cap-plate at the superior end and the socket-base at the inferior end. In yet a further preferred embodiment, the boot is sealed such that surrounding bodily fluids cannot contact the functional elements of the prosthetic device. In still a further preferred embodiment, the sealed boot can contain fluids to lubricate the functional elements of the prosthetic device.

In a preferred embodiment, one or more vertebral plates are utilized to connect the prosthetic device of the subject invention between two vertebrae. Specifically, superior and inferior vertebral plates can be attached to the respective vertebrae within a spine. The prosthetic device of the subject invention can thus be positioned between, and connected to, the vertebral plates.

In a further preferred embodiment, vertebral plates are threaded in opposite directions. This allows the prosthetic device to be positioned between the vertebral plates and turned in one direction to screw the prosthetic device to both vertebral plates at the same time. It may also be preferable to utilize screws to hold the prosthetic device in place after it has been screwed to the vertebral plates.

Thus, the present invention provides an articulated, modular 6-Degree-of-Freedom (6-DOF) spatial mechanism for intervertebral spinal disc prosthesis that provides highly advantageous spatial motion between upper and lower vertebrae of an FSU.

The unit may be used to assist in maintaining natural spinal flexibility and motion during simultaneous, dynamically changing, curvilinear axial, lateral and sagittal rotations and translations, regardless of the details and wide variations of that motion in humans.

The unit may also be used to assist in maintaining proper disc spacing, absorbing compression shocks, sustaining static loads, helping to eliminate spinal cord and nerve root compression, resisting torsion and extension forces and reducing excessive facet joint stress and wear.

The mechanism's components, when coupled together, form a device that preserves its own mechanical integrity, connectedness (kinematic chain), and motion properties throughout the biologically constrained motion space (workspace) of the FSU. The complete generality of the device allows for modifying the range of the mechanism's motion parameters and workspace, physical size, material composition, and mechanical strength to suit ordinary mechanical applications as well as spinal disc prosthetics.

The complete 6-DOF motion capability of the prosthetic disc linkage mechanism, which in a preferred embodiment modularly fits between the vertebral plates as a replaceable unit, is able to allow natural motions dictated by the muscles and ligaments of the spine. A central compression-extension, machined helical spring with an elastomeric or hydrophilic gel partially filling the spring core, automatically rotates to align itself with a normal component of applied force and absorbs and transmits spinal shocks while helping to maintain normal intervertebral spacing. The mechanism can support further shock absorption and automatic bearing lubrication by means of a self-contained internal hydraulic pumping and damping system using a biocompatible, for example, but not limited to, a silicone fluid, or, for thermoplastic bearings and mechanism parts, for example, but not limited to, a biocompatible saline solution.

Throughout normal motion, the system of the subject invention stabilizes the FSU because of its ability to maintain continuity of mechanical connection between the superior and inferior vertebrae while at the same time providing load bearing and permitting motion only within the nominal disc operating range or workspace. The mechanical continuity is realized by a kinematic chain of jointed elements. In order to stabilize the FSU, a preferred embodiment of the subject invention generates nominal forces opposing vertebral motions by means of a central, rotating, machined helical spring with an elastomer or hydrophilic gel core and by means of the device structure itself. The mechanism also includes hydraulic-damping to absorb and even out energy shocks.

BRIEF DESCRIPTION OF DRAWINGS

FIG. 2A illustrates an embodiment with a right-circular cylinder boot and FIG. 2B illustrates an embodiment with a spherical boot.

FIGS. 7A, 7B and 7C illustrate exploded views of one embodiment prosthesis of the subject invention. FIG. 7A illustrates interior elements of one embodiment. FIG. 7B illustrates a right-circular cylinder boot utilized with clamping rings and FIG. 7C illustrates an embodiment with a spherical boot utilized with clamping rings.

FIGS. 23A and 23B and FIGS. 24A and 24B represent alternative rod-bearings that may be used to replace ball-bearings in the prismatic joints. In circular form, they can also replace ring bearings. The bearings do not roll but have different contact surfaces, resulting from different choices of cross-sections and lateral surface shapes, and grooves for lubrication flow.

FIG. 25B portrays the sagittal plane projection of the device elements through the polar-axis of the ball. The projection indicates that the plane-bearing guide, cap plate, and superior vertebral plate slide from anterior to posterior positions along the sagittal prismatic joint.

FIG. 26B portrays the sagittal plane projection of the device elements, through the polar-axis of the ball. The projection indicates that the plane-bearing guide, cap-plate and superior vertebral plate slide from posterior to anterior positions along the sagittal prismatic joint.

FIG. 27B is a cross-sectional view of the frontal plane projection through the polar-axis of the ball which indicates that in pure right-lateral bending, the cap-plate and superior vertebral plate slide from left-to-right along the lateral prismatic joint.

DETAILED DISCLOSURE

Figure 1C:
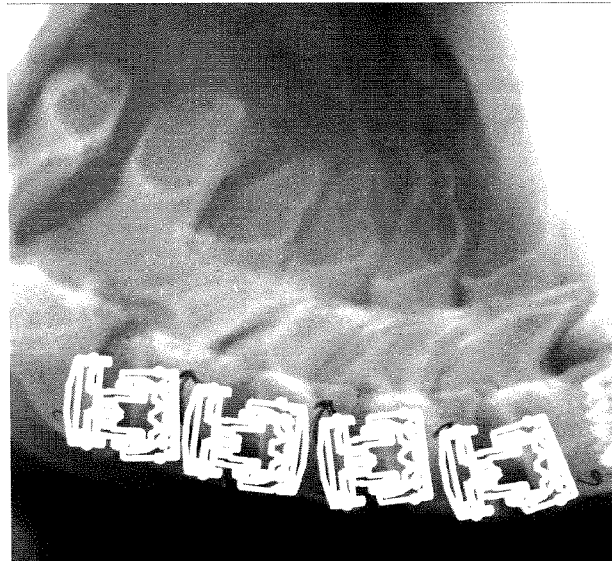
FIGS. 1A-1C (photographs) are photographs of superimposed sagittal plane projections, through the central axis of the spinal disc prosthesis, onto sagittal view radiograms of the cervical spine, from left to right, in flexion, neutral, and extension. The modular 6-DOF spatial mechanism is shown as prostheses for C2-C3, C3-C4, C4-C5, and C5-C6 since the workspace of the invention is able to correspond to the workspace of each of these functional spinal units.

The subject invention provides a spinal disc prosthesis capable of providing spatial movement with up to 6 independent degrees of freedom. The modular prosthetic disc of the subject invention contains the mechanisms responsible for its general motion capability. These mechanisms consist of three orthogonal prismatic joints for general positioning in three-dimensional space and a spherical joint for three-dimensional orienting. The current invention differs from existing designs since, in a preferred embodiment, it provides six-degrees-of-freedom throughout the FSU workspace while bearing loads and maintaining the integrity of intervertebral spacing.

In a preferred embodiment, the subject invention possesses three orthogonal linear (prismatic) joints and a three-independent rotational degrees-of-freedom orienting ball-and-socket joint that, when assembled for insertion into a spine, form a kinematic chain. When appropriately scaled, the device tracks arbitrary three-dimensional translational and three-dimensional rotational motions of the superior vertebra with respect to the inferior vertebra of an FSU from C2-C3 down to L5-S1.

The modular 6-DOF spatial mechanism for human spinal disc prosthesis described here overcomes problems inherent in previous devices and can offer a number of other novel features such as modularity, scalability, static and dynamic loading, shock absorption, lubrication pumping, hydraulic damping, and wide applicability throughout the spinal column.

A preferred embodiment of the spinal disc prosthesis of the subject invention is operated by the muscles and ligaments of the spine. These muscles and ligaments work against the spring-damping system of the prosthesis and dictate the motion of the FSU vertebra rigidly attached to superior vertebral plate of the prosthesis. The 3-DOF spherical joint realized by the ball-and-socket elements tracks the spatial orientation of the superior vertebral plane fixed in the superior vertebral plate which, in turn, is fixed in the superior vertebra of the FSU. The instantaneous axis of rotation changes during the motion of the superior vertebra of the FSU and, therefore, in general, differs from the fixed rotation center of the ball-and socket joint. Ball-and-socket action alone, therefore, does not produce all the required translations of the superior vertebra, but does produce the correct and final orientation. It requires the polar-axis (piston-and-ball) prismatic joint, along with the lateral and sagittal prismatic joints to fix the three coordinate position of a point in the superior vertebral plane. Together the ball-and-socket and the three prismatic joints form the kinematic chain that determines the location and orientation of the vertebral plane, completely fixing it in space. In this manner the prosthetic spinal disc tracks and constrains the motion of the superior vertebra to its natural locus of motion.

Advantageously, the devices of the subject invention can provide 1) effective static load bearing through the spring, 2) hydraulic damping and shock absorption by means of hydraulic pumping action conjoined with spring and elastomer (or hydrophilic gel) reaction in the spring core, 3) automatic hydraulic lubrication of all joints, 4) intervertebral stability, 5) 6-DOF motion tracking throughout the prosthesis workspace, 6) and a mechanically programmable prosthesis workspace.

The motion elements of the prosthetic device of the subject invention can be fabricated of, for example, titanium steel, titanium-carbide-coated stainless steel, polyurethane, polyurethane thermoplastic, cobalt-chromium-molybdenum alloy, plastic, glass, or other materials or combinations thereof. In a preferred embodiment, the motion elements of the prosthetic device of the subject invention are fabricated from titanium and use hardened ball-bearings on moving interfaces. In a further preferred embodiment, a mix of polyurethane thermoplastic bearings and polyurethane, titanium, cobalt-chromium-molybdenum alloy and titanium-carbide-coated hardened stainless steel components are utilized.

In a preferred embodiment, the modular 6-DOF spatial mechanism for spinal disc prosthesis of the subject invention comprises a superior and an inferior vertebral plate, as well as a flexible, boot-protected, modular and replaceable 6-DOF prosthetic disc mechanism (linkage). The vertebral plates can be formed from a biocompatible material such as, for example, titanium, cobalt-chromium-molybdenum alloy, or titanium-carbide-coated stainless steel with a bone fusion matrix on the side of the plate shaped as a spherical surface to enhance surface area contact between vertebra and the vertebral plate.

The current invention allows installation of the vertebral plates followed by the modular prosthetic disc mechanism, or the whole prosthesis at once, depending on indicated surgical procedures and efficiencies.

Any number of existing techniques known to those with skill in the art may be used to embed the superior vertebral plate of the subject invention into the bone of the superior vertebra and the inferior vertebral plate into the bone of the inferior vertebra of an FSU.

In a preferred embodiment, a boot surrounds the prosthetic device of the subject invention and provides a biocompatible barrier between fluids that may be sealed within the prosthetic device and fluids within surrounding tissues. The boot may comprise a sturdy, flexible or elastic material, such as, for example, corrugated materials, woven fiber materials, and elastic materials, or other non-homogeneous materials. In a further preferred embodiment, the boot comprises woven, flexible fibers embedded in a strong, flexible silicon elastomer. The embedded fiber weave, in the embodiment mentioned above, can assist in torsion loading on the prosthesis as well as loading during flexion and extension. In an additional preferred embodiment, the weave direction of the embedded fibers is diagonal relative to the central axis of a preferred, spherical or right-circular cylinder embodiment of the boot structure.

In contrast to the skirt in the Bryan et al. design (U.S. Pat. Nos. 5,674,296; 5,865,846; 6,001,130; and 6,156,067), the boot of the subject invention can serve multiple purposes, other than sealing fluids. In a preferred embodiment, the corrugated boot, consisting of a rugged fiber elastomer designed for flexibility and toughness, can assist in torsion loading and opposes extension under nominal conditions, thus, reducing nominal spinal muscle stress in the neutral position. The boot can also help maintain the integrity of the prosthesis, and can share, with the interlinking mechanisms the force loads that are placed on the subject prosthetic device. In this sense, the boot performs, for example, as a prosthetic ligament.

In a preferred embodiment, the corrugated boot has asymmetric thickness, using more reinforcing fiber in the posterior portion and less in the anterior portion, making the anterior portion more flexible and the posterior portion less flexible, but stronger and more durable. This configuration can reduce interaction with the spinal column or nerve ganglia when the boot is expanding and/or contracting. As the FSU flexes, the boot contracts, primarily the highly flexible thinner sections. In a neutral position, the boot is under about 20% stretching in the anterior part and about 10% or less in the posterior. At maximum extension the boot stretches another 20% in the anterior portion and again, about 10% or less in the posterior.

In a preferred embodiment, the modular prosthetic disc mechanism of the subject invention connects with the superior and inferior vertebral plates at each end. In a further preferred embodiment, the modular prosthetic disc mechanism of the subject invention connects with the superior and inferior vertebral plates by twisting or screwing into the superior and inferior vertebral plates connected to the respective vertebra. Thus, in yet another preferred embodiment the superior and inferior vertebral plates possess an opposite screw sense, such that twisting or turning in a single direction connects the modular prosthetic disc mechanism to both vertebral plates simultaneously. This enables easier installation and replacement of the prosthetic device if necessary.

In a preferred embodiment, a threaded projection on the cap-plate of the modular prosthetic disc mechanism screws into the superior vertebral plate and a threaded projection on the socket-base screws into the inferior vertebral plate. The modular prosthetic disc mechanism, after being firmly screwed onto the vertebral plates, locks and aligns to those plates by one or more anterior screws. In a further preferred embodiment, three anterior screws are utilized to secure each vertebral plate.

While the intent of the subject invention is to provide a reliable spinal disc prosthesis that does not fail over the patient's lifetime, special stress or operational conditions might require its replacement. The modular features of the subject invention provide a means for surgical removal or replacement of the prosthetic disc linkage without disturbing the bone-prosthesis interface, as long as there is no damage to the vertebral-plates or the interfaces of those plates with the vertebrae. This modularization of the prosthetic device of the subject invention provides aspects of performance, serviceability, safety and security heretofore unavailable in this field, and at a considerably reduced risk to the patient.

Figure 1B:
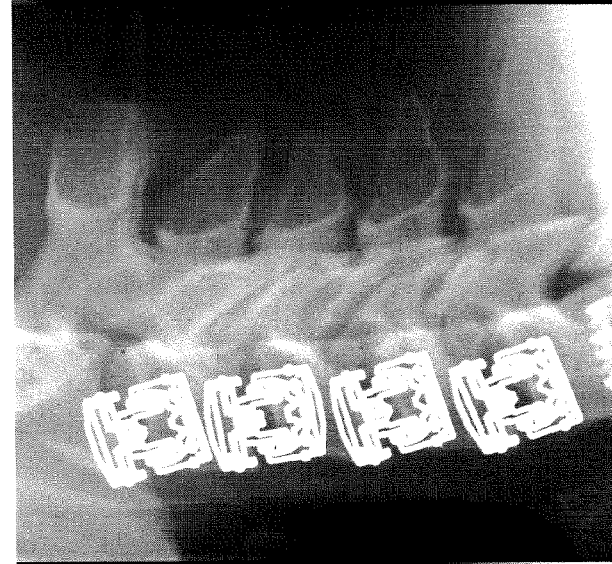
Figure 1A:

FIGS. 1A-1C illustrate possible installations of the invention into four locations (FSUs) in the cervical spine: C2-C3, C3-C4, C4-C5, C5-C6. The dimensional freedom of the device tolerates some misalignment. The degree of tolerance depends upon the FSU and its motion requirements. Those FSUs with less demanding motion requirements (smaller workspaces) will most likely accommodate greater misalignment errors.

In an alternative embodiment, the superior vertebral plate may be formed as part of the cap-plate and the inferior vertebral plate may be formed as part of the socket-base, such that each previous pair of elements forms a single element. This alternate embodiment requires no threading or lock screws and eliminates the module of the prosthesis.

However, all the other features of the subject invention as discussed above would still be applicable to this alternate embodiment.

As noted above, the modular prosthetic disc mechanism of the subject invention provides six-degrees-of-freedom (6-DOF) throughout the FSU workspace. In a preferred embodiment, the modular prosthetic disc mechanism base element, the socket-base or socket element, consists of a right-circular cylinder with a spherical cavity with a radius of curvature r that depends on the overall size of the socket-base. In a preferred embodiment, a ring-bearing circles the lower interior spherical surface of the socket cavity to support a chambered-ball. The line from the ball-bearing centers on the socket ring-bearing to the ball center intersects the spherical surface of the ball at the bearing point of contact. Together, the socket and chambered-ball form a ball-and-socket joint that realizes the necessary three-dimensional orientation of the superior vertebra by the prosthesis. Alternate embodiments can utilize different external geometries for the socket-base, such as, but not limited to, elliptical, square, rectangular, and combinations thereof. However, the cavity that contains the chambered-ball or the area that supports or confines the chambered-ball must be able to produce three independent rotational degrees-of-freedom in the ball-and-socket joint formed with this element and a chambered-ball. Thus, in a preferred embodiment, the socket-base cavity is spherical.

The device of the subject invention can also comprise a partially-spherical chambered-ball, which may be slightly larger than a hemisphere, which locks into a spherical cavity in the socket-base, that itself is also slightly larger than a hemisphere.

In a preferred embodiment, the chambered-ball also has one or more hydraulic portals for transferring, for example, lubricants, biocompatible saline solutions, combinations thereof, or other materials throughout the mechanism.

In a further embodiment, a girdle ring-bearing on the exterior surface of the chambered-ball, just below the chambered-ball's equator, rotates with the ball and provides a second ring-bearing for transferring loads from the chambered-ball to the socket-base. The girdle ring-bearing does not rotate out of the socket cavity, being blocked by a chambered-ball ring-bearing fastened inside the ball's cavity opening.

In one embodiment, the socket joint may be manufactured as two halves within which the chambered-ball is positioned before the two halves are sealed around the chambered-ball. In a further embodiment, the socket's spherical cavity and spherical ball share the same axis or center, but the socket has a slightly larger radius of curvature than the ball in order to allow for bearing gaps between the chambered-ball's spherical surface and the surface of the socket's spherical cavity.

In another embodiment, the ball and socket form a lower kinematic pair wherein the interfacing spherical surfaces form the joint bearings.

The subject invention can also utilize a piston 12 comprising a right-circular cylinder 66 (FIG. 11, FIG. 22) located within the cavity of the chambered-ball. Also, in a preferred embodiment, the chambered-ball possesses a right-circular cylindrical cavity for holding a piston of the same cross section, but of slightly smaller radius, to allow gaps for the piston and chambered-ball ring-bearings. The piston and chambered-ball form a cylindrical joint, in which the piston with a right-circular cylinder cross-section can rotate about its center axis within the ball. In a further preferred embodiment, the piston has the ability to telescope in and out of the chambered-ball cavity 35 (FIG. 9) to match the required intervertebral gap required by the position of the FSU. In an alternate embodiment, a piston with a non-circular cross section can be utilized with a chambered-ball cavity having matching cross sections. The chambered-ball and telescoping piston together create the polar-axis prismatic joint 115 (FIG. 12).

The piston itself preferably possesses a right-circular cylindrical cavity for mounting a machined helical spring for load management. The piston ring-bearing attaches to the end of the piston. At maximal flexion, the piston recesses into the ball cavity. At maximal extension the piston extends out of the ball cavity until the ring bearings interfere and prevent/oppose further extension. In other FSU configurations that include lateral bending and axial rotation, the piston will be at positions between these extremes.

The piston is comprised of a rigid material that can be, for example, titanium steel, titanium-carbide-coated stainless steel or cobalt-chromium-molybdenum alloy or from rigid, ultra-high-molecular-weight polyethylene, or combinations or alloys thereof.

Figure 11:
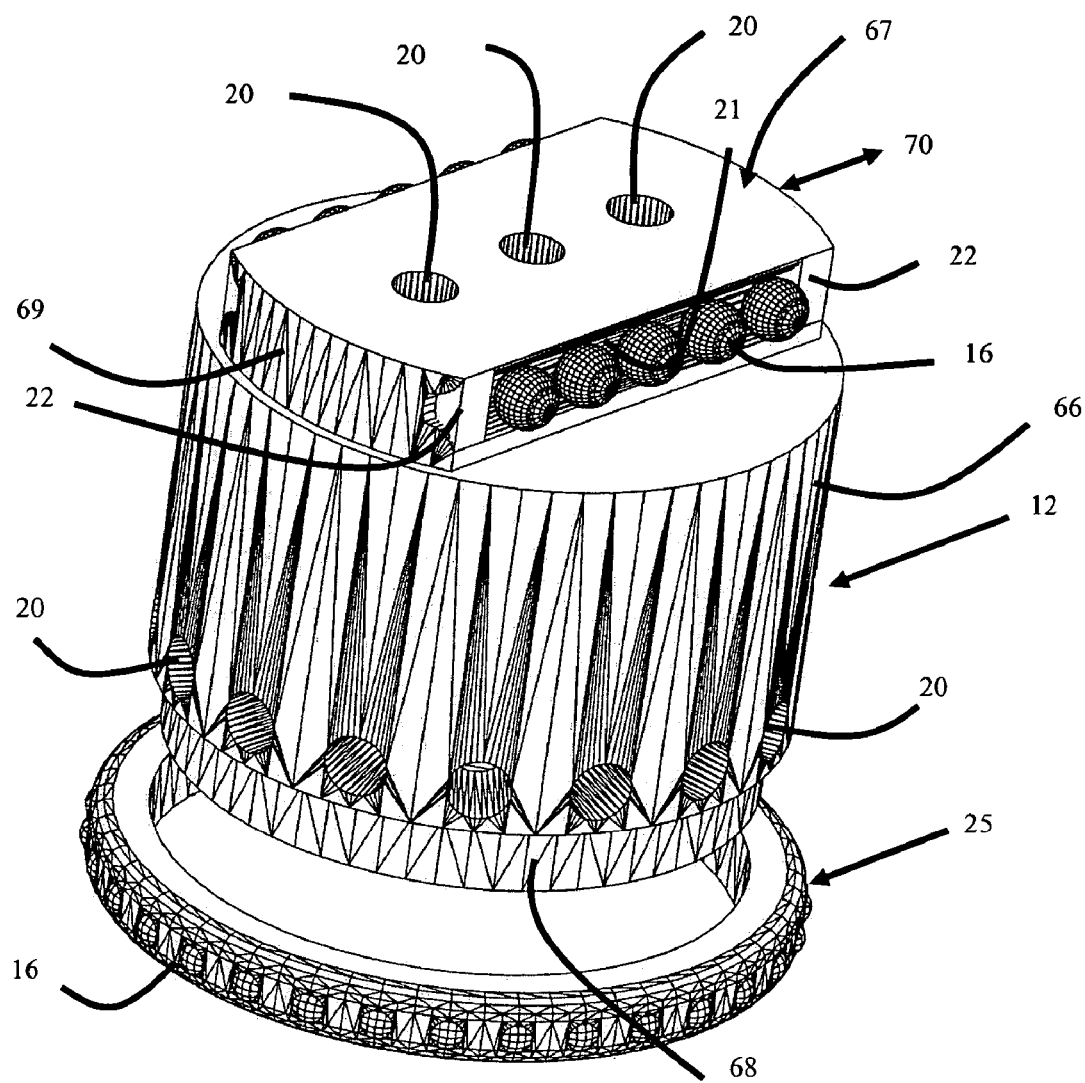
FIG. 11 shows an embodiment of the piston as a right-circular cylinder with ring-bearing and hydraulic portals. The hydraulic portals allow passage of fluid in and out of the piston cavity. The hydraulic portals at the top of the piston allow lubricating fluid to pass over the prismatic joints.
Figure 12:
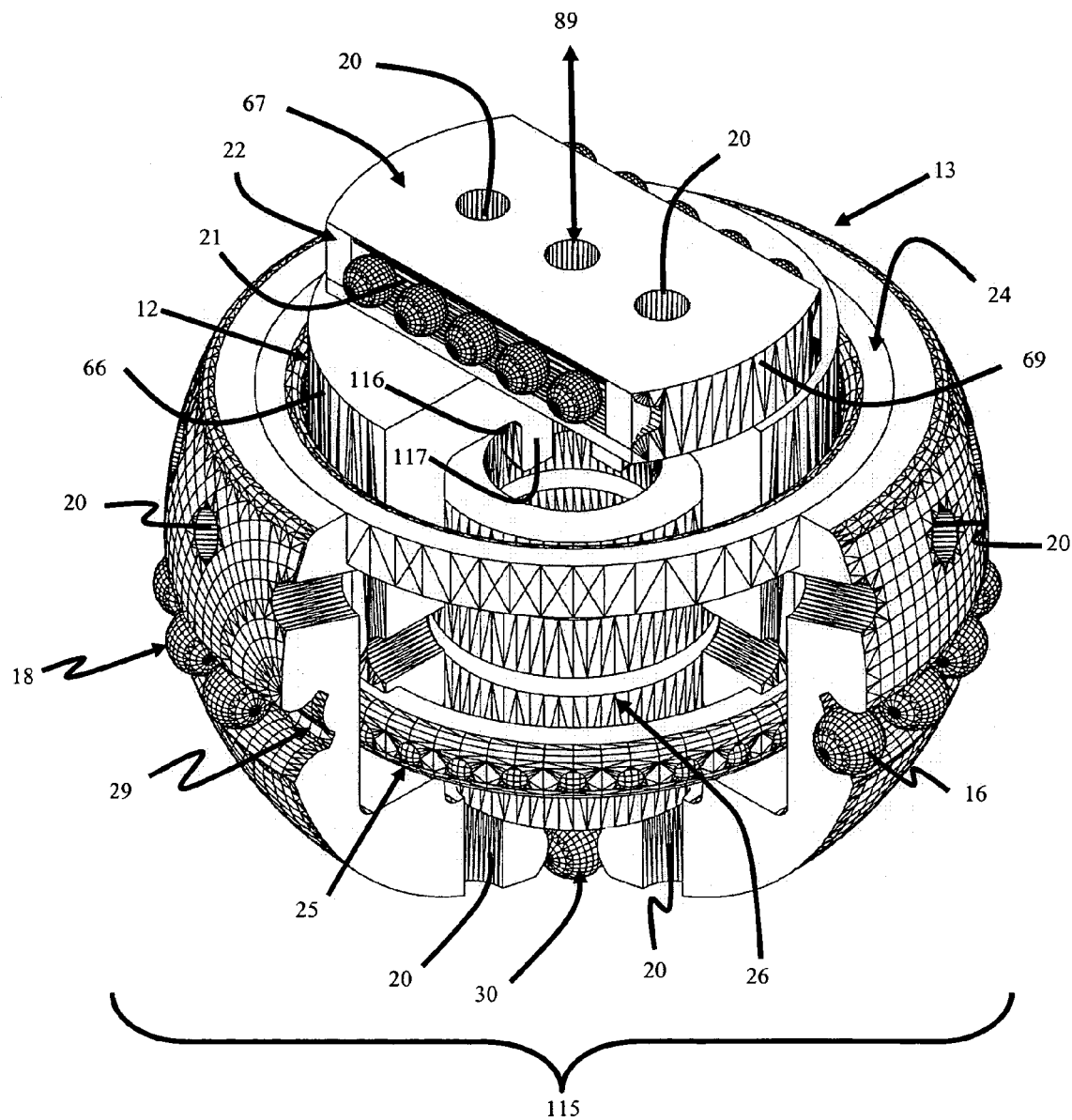
FIG. 12 illustrates the piston positioned within the chambered-ball to create the polar-axis prismatic joint.
Figure 13:
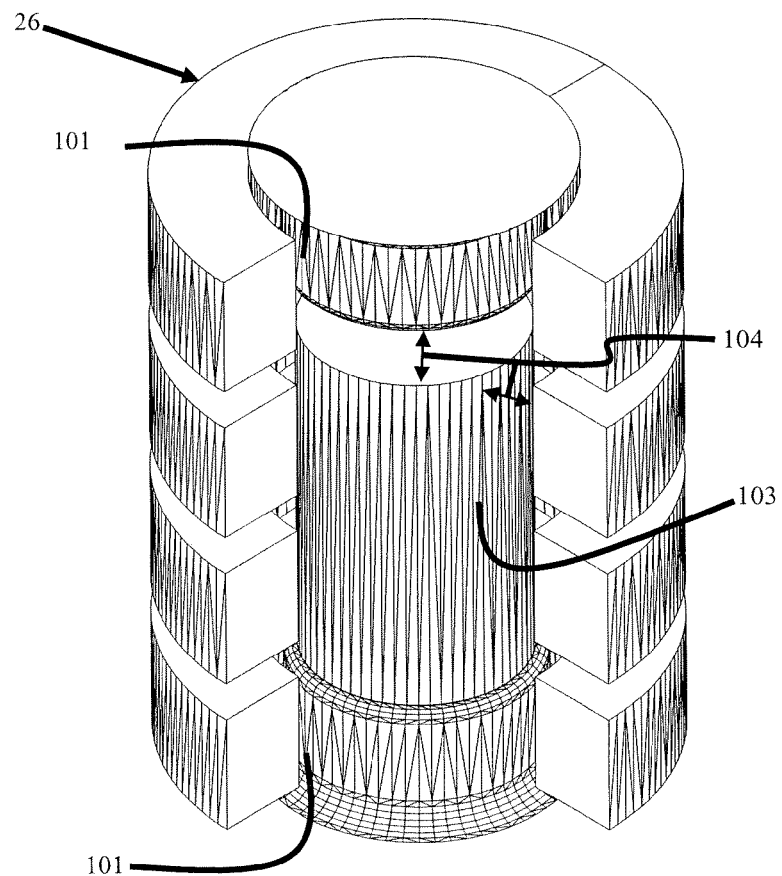
FIG. 13 stylistically depicts a threaded, helical spring. A fraction of the spring cavity can be filled with a compressible elastomer and/or hydrophilic gel to assist in shock absorption and compressive load bearing near the maximal compression configuration of the device.

In yet a further embodiment, the piston has a cylindrical cavity 83 (FIG. 22) to contain, for example, a spring, elastomeric device, or other shock absorbing material 26 (FIGS. 12 and 13). The lower element of the sagittal prismatic joint 67 (FIG. 11) with lateral bearing raceways 21, which may be machined, sits on top of the piston.

Hydraulic portals 20 (FIG. 11) surround the piston, in one embodiment, just above the piston ring-bearing, and one or more, preferably three, pierce the piston top. During movement of the FSU, the piston can pump lubricating fluid out of the piston cavity as the piston telescopes into the chambered-ball and can take or "pull" lubricating fluid into the piston cavity as it creates a negative pressure gradient in the piston core when it telescopes out from the chambered-ball. The number, size, and placement of hydraulic portals on the piston can affect fluid flow distribution, hydraulic damping, and shock absorption.

Combining the polar-axis prismatic joint with the ball-and-socket orienting joint produces a 4-DOF spherical joint 115 (FIG. 12) that orients the piston that then telescopes in or out as FSU motion requires. From spherical symmetry, this portion of the prosthesis is capable of orienting the piston at any sagittal, frontal, and axial angles and positioning the piston at any radius within the piston stroke distance.

In a further preferred embodiment, the device of the subject invention utilizes two dual-track, orthogonal linear bearings to produce two further, orthogonal, independent translational degrees-of-freedom, referred to as the lateral prismatic joint and the sagittal prismatic joint. These two prismatic joints define an imaginary plane of motion called the superior vertebral plane, which is fixed in the superior vertebral plate and always orthogonal to the polar axis. In a preferred embodiment, three elements with dual-track linear raceways assemble to form the sagittal and prismatic joints: the cap-plate is fixedly attached onto the plane-bearing guide that is fixedly attached onto the piston sagittal bearing support. For all motions the prosthesis maintains the bottom surface of the plane-bearing guide parallel to the moving superior vertebral plane whose motion the FSU generally dictates.

In a preferred embodiment, the prismatic joint dual tracks resist moments of force to provide smoother operation and joint stability. In the presence of external forces, the chambered ball-and-socket joint and polar-axis prismatic joint orient and position this imaginary superior vertebral plane to keep it fixed relative to the superior vertebra. The combined action of the sagittal and lateral prismatic joints allows a fixed point in the superior vertebral plane to slide into any position in that plane dictated by natural FSU motion.

In yet a further embodiment, ball- or rod-bearings can be utilized with the prismatic joint raceways to couple the two raceway elements: the cap-plate and the plane-bearing guide for the lateral prismatic joint, and the plane-bearing guide and the piston for the sagittal prismatic joint; thus, integrating and linking all three elements together.

To clarify by way of example, the plane-bearing guide essentially hangs from the cap-plate and the piston essentially hangs from the plane-bearing guide with bearings locking the elements together.

The raceway bearing may utilize, for example, spherical, cylindrical, or rod bearings and comprise, for example, titanium steel, titanium-carbide-coated stainless steel, thermoplastic, various plastics, glass, or other durable, rigid material or combinations or alloys thereof. In addition, rod-bearings may utilize different cross-sectional shapes to effect lubrication flow and bearing contacts. The raceway may also utilize materials that maximize interface with the bearings. Linear bearing stops and separators can assist with maintaining proper ball-bearing position, but rod-bearings usually do not require separators.

Alternative styles of rod-bearings (FIG. A, B, C, D) may be used to replace ball-bearings in the prismatic joints. For example, linear bearings that do not roll but have different contact surfaces, resulting from different choices of cross-sections and lateral surface shapes can be utilized. Such linear bearings can also have grooves for lubrication flow along the length of the bearing. In circular form, they can also be used to replace the ring bearings in the subject invention.

Additional embodiments utilize bearing stops that extend a sliding member of a prismatic joint to reduce the amount of translation motion from the maximum since the extended bearing-stop will impact the skirt of the cap-plate of the prosthetic disc linkage before the sliding member does. In a preferred embodiment, the cap-plate skirt limits the maximum range of motion of both the sagittal and lateral prismatic joint. However, if the maximum permissible workspace must be reduced for clinical or other reasons, oversized linear bearing stops can be utilized. For example, if a patient must restrict lateral bending of the spine at the site of the prosthesis, the lateral prismatic joint bearing stops can be made large enough to limit translation in the left or right lateral direction by independent amounts. In like manner, oversized bearing stops on the sagittal prismatic joint limit flexion and extension by independent amounts. Bearing stops, therefore, can provide a means to control the amount of workspace volume realized by the prosthesis.

For flexion and extension, the sagittal prismatic joint and the polar-axis prismatic joint together allow translation of the superior vertebral plate in the sagittal plane while rotating it about the sagittal axis. The lateral prismatic joint does not enter into pure flexion and rotation movements. For pure lateral bending, the polar-axis and lateral prismatic joints provide the joint motion components while rotating about the lateral axis with the piston. Natural lateral motion of the cervical spinal generally includes some axial rotation, motion to which the device automatically accommodates. In each case, the spherical joint automatically rotates and extends or retracts the piston according to the forces exerted on the prosthesis.

The lubricating fluid contained within the prosthetic device of the subject invention by the boot seal, can be pumped or otherwise moved around the elements of the device by the piston during spinal motion, which tends to separate all the interacting bearing surfaces in a manner similar to the action of synovial fluid in a diarthrodial joint; this can increase the efficiency of the bearing surface and reduce wear.

A yet further embodiment includes a rotating, helical central-spring with, for example, an undersized elastomer or hydrophilic-gel core (Bao and Higham's hydrogel, U.S. Pat. No. 5,192,326, provides shock absorption under impulsive loads, acting much like the nucleus pulposus of a natural disc) for controlling or managing static and dynamic loads near maximum flexion. These load-bearing elements, in a preferred embodiment, fit into the right-circular cylinder cavity of the piston to control maximal compression. Inside threading on the top and bottom of the helical spring provides a means of screwing the spring to threaded mounting posts on the ceiling of the piston cavity and the floor of the chambered-ball cavity. However, those with skill in the art will recognize that other means of securing the spring may be utilized. Thus, the spring, a flexible load bearing mechanism, is the element that links the piston to the chambered-ball.

In an alternative embodiment, the piston itself can be modified so as to mimic the helical spring with threads at its base that protrude much like the piston-ring bearing. This protrusion can create a bearing gap between the piston and the chambered-ball lateral surface. A matching threading at the bottom of the chambered-ball cavity allows the piston to screw into the chambered-ball cavity. In a further alternative embodiment, the outer/exterior, lateral, helical surface of a piston configured as a helical spring may also be configured with rounded, protruding edges to provide bearing surfaces that slide over the smooth, chambered-ball cavity lateral surface. This embodiment eliminates the need for piston and chambered-ball ring-bearings, because the helical piston-spring can maintain joint connection integrity because the piston base is able to screw into the bottom of the chambered-ball cavity.

In a preferred embodiment, the rotating, helical central-spring, as described above, is able to provide a balancing force to nominal gravitational loading in the neutral position of the FSU. Somewhere between neutral and maximum extension, for example, at approximately halfway, the spring attains an unloaded state. From that point to maximum extension, the spring then opposes the extension motion and stretches. The spring reaches greatest compression in maximum flexion and greatest extension in maximum extension of the FSU.

In an even further embodiment, the spring can provide different spring constants in series or even non-linear spring characteristics to match application load requirements. Since the piston constrains the spring to align with the polar-axis of the ball-and-socket, regardless of relative vertebral orientation or position, external forces principally act along the length of the spring or cause joint motion, which can be a desirable feature. Thus, in this embodiment, non-polar external forces acting on the prosthesis will cause the mechanism to orient itself so as to align the piston top surface with the superior vertebral plane as it moves under muscle control. The spring is able to balance central forces in a spherical robot and prevent/oppose the collapse of the mechanism under load. Proper spring design can also accommodate the various intervertebral distances required during FSU motion, which can eliminate excessive forces on the facet joints in the process.

Forces acting on the prosthetic disc linkage move the various prismatic and orienting joints allowing them to follow the natural motion of the superior vertebra with respect to the inferior vertebra of an FSU. Generally, forces acting on the superior vertebral plate decompose into a force tangent to the defining sphere of the chambered-ball and a force directed along the polar-axis of the ball. The former force provides rotational motion of the chambered-ball in its socket and the latter force provides a compression or extension load on the load-bearing system, regardless of the complexity of the superior vertebral motion.

A further embodiment of the device of the subject invention exhibits flexion and extension in only the sagittal plane. Thus the socket-base cavity can be devised as a right-circular cylinder with its principal axis aligned with the sagittal axis and with two ring-bearings, one at each end of the cylinder. In this embodiment, the "chambered-ball" becomes a chambered-cylinder with a piston and sagittal prismatic joint, providing a total of 3-DOF, all that is necessary for arbitrary position and orientation in the sagittal plane only. If the chambered-cylinder cavity is a right-circular cylinder as in a preferred embodiment, then there follows a fourth degree of freedom that allows axial rotation. In this embodiment, the plane-bearing guide and cap-plate integrate into a single unit with only bearing supports for the sagittal prismatic joint.

Figure 28:
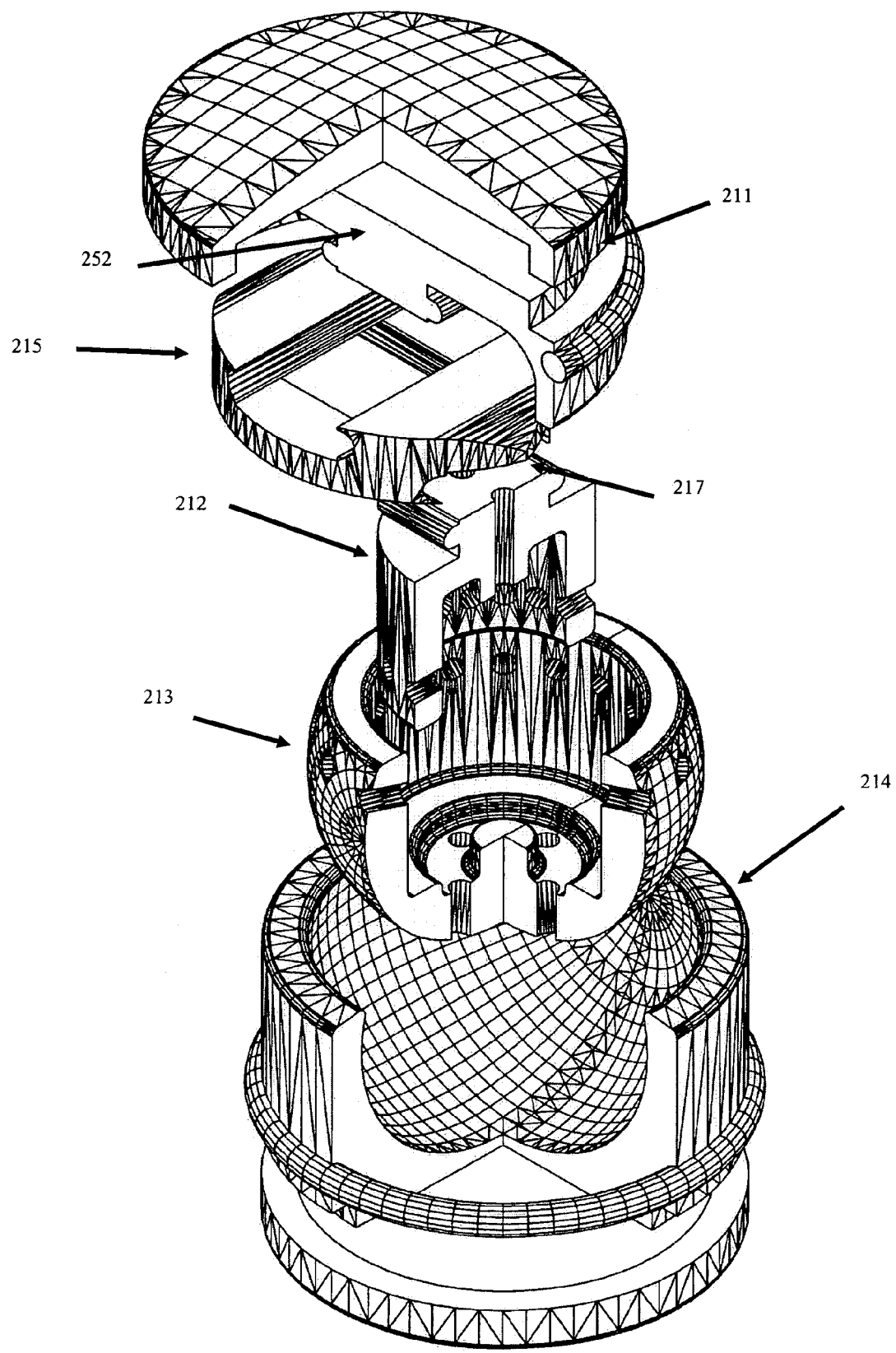
FIG. 28 illustrates an embodiment of the invention using only lower pairs for all joints, making it a true 6-DOF linkage as opposed to 6-DOF mechanism illustrated in alternative multi-point or line contact bearings. This embodiment employs surface contacts for all joints. A realization could employ a mix of surface, line, and point contact bearings for the motion interfaces.
Figure 29:
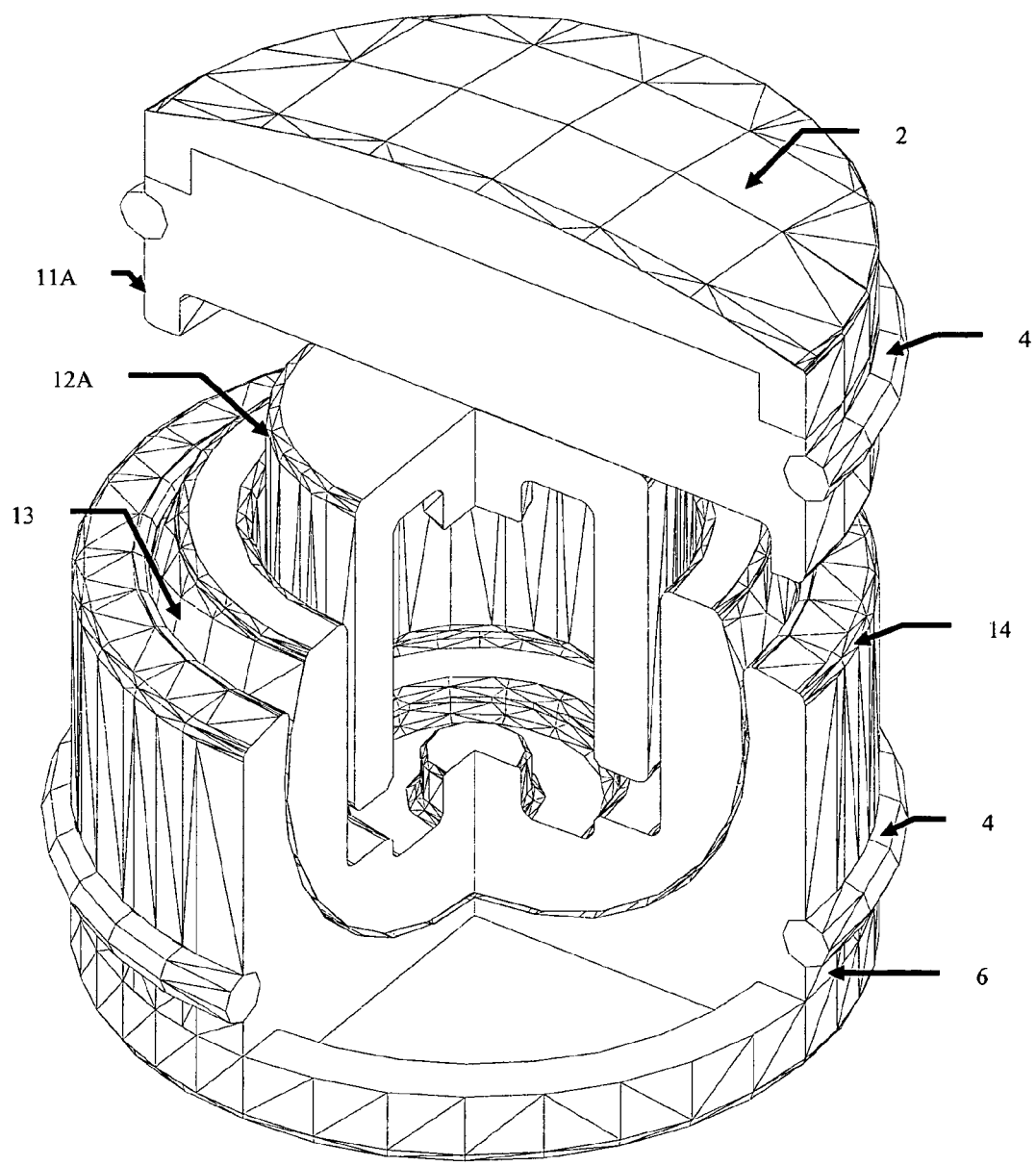
FIG. 29 illustrates a cut-away view of the embodiment shown FIG. 28 with the components assembled.

A further alternative embodiment utilizes lower kinematic pairs for all joints (FIG. 28). This alternate embodiment eliminates or reduces the use of ball- and rod-bearings, replacing some or all of them with surface bearings. To facilitate motion, both surfaces of a pair are, for example, but not limited to, tough thermoplastic bearing material or titanium or other hard, low friction biocompatible material or combinations thereof. By way of further example, the cap-plate, piston and socket-base could comprise for example, titanium-carbide-coated stainless steel, and the plane-bearing guide and chambered-ball could further comprise for example, a suitable thermoplastic. Another example is that all elements but the superior and inferior vertebral plates are thermoplastic bearing material. These alternative embodiments may increase friction in the joints that can reduce muscle stress, facilitate easier construction, require fewer parts, and provide a more robust device capable of managing greater loads.

Embodiments of the spatial mechanism will differ from each other at various levels of the spine, primarily in engineering design choices regarding materials (for example, but not limited to, titanium steel, titanium-carbide-coated stainless steel, cobalt-chromium-molybdenum alloy, polyurethane, high-molecular-density polyethylene, biologically derived materials and alloys or combinations thereof), size, strength, thicknesses, and so forth. The configuration, interaction, geometry, kinematics and shape of the basic structural elements that generate the motion, apply equally along the spine.

Figure 10:
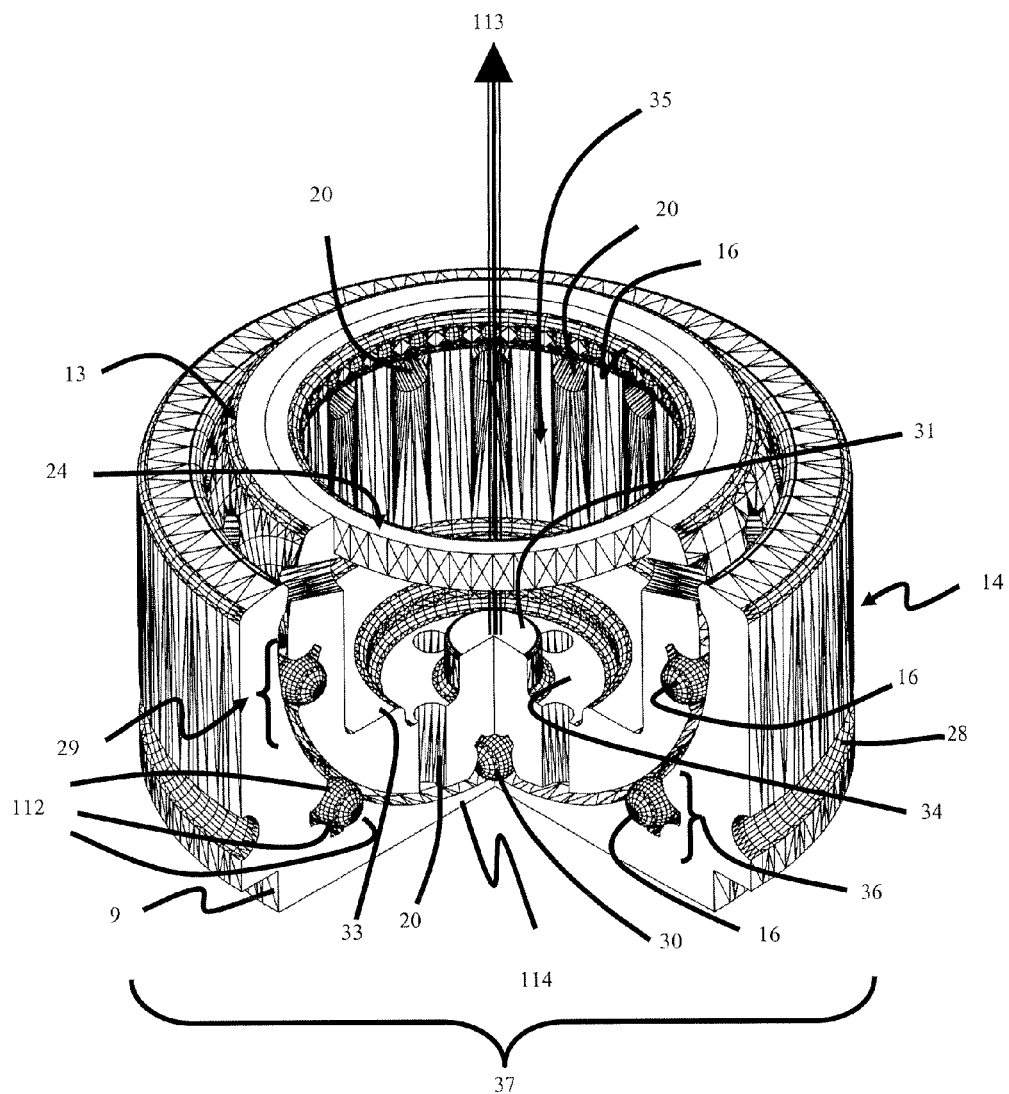
FIG. 10 illustrates a cut-away view of the chambered-ball and the socket-joint and shows the placement of the chambered-ball within the socket cavity and the arrangement of the girdle, socket-base, and chambered-ball ring-bearings. The chambered-ball and the socket-base combined form an essentially spherical joint.
Figure 21:
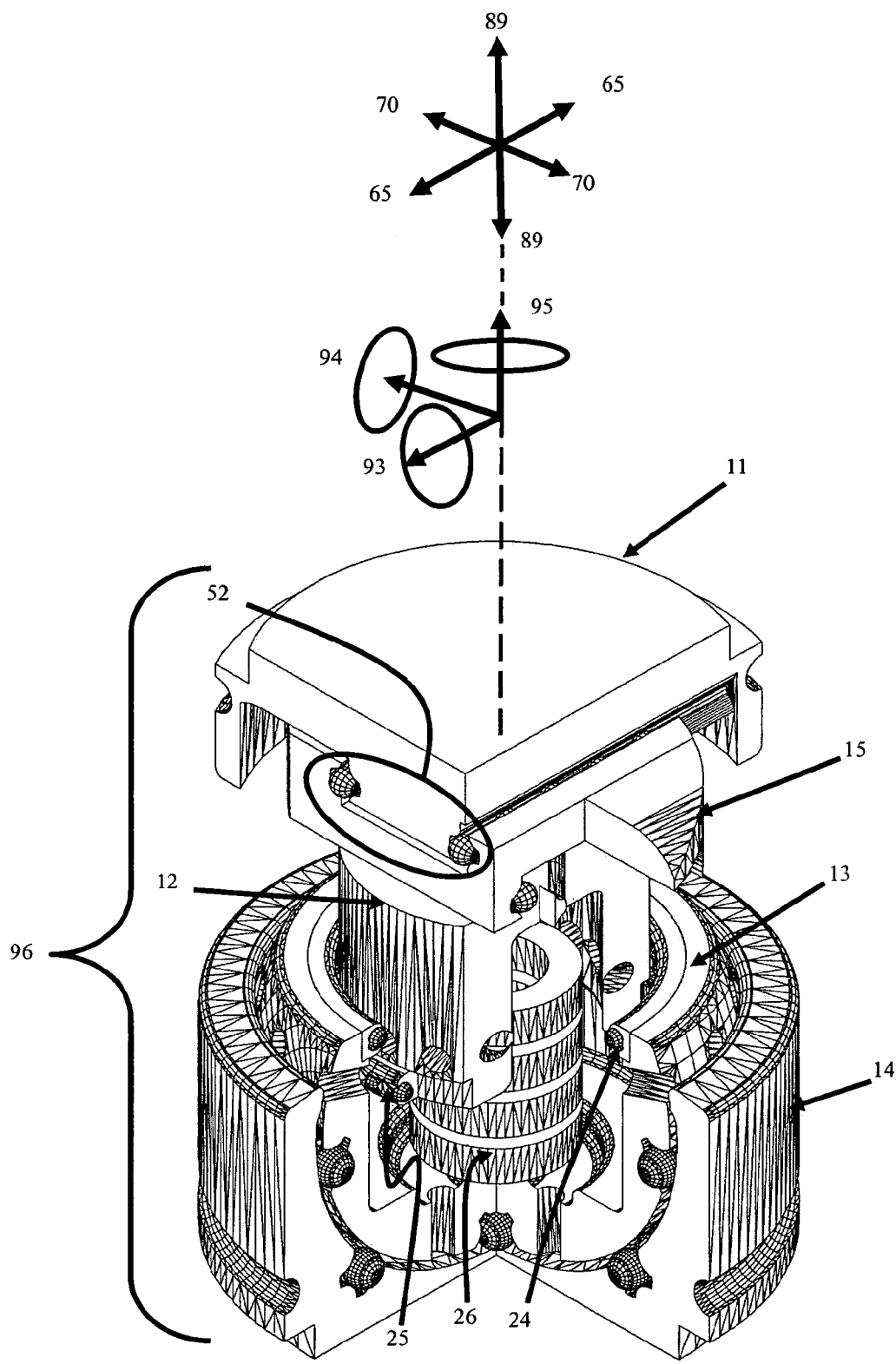
FIG. 21 illustrates all the joint mechanisms of the modular 6-DOF spatial mechanism for human disc prosthesis with a cut-away view.

The foregoing general discussion of the devices of the subject invention can be further illuminated by reference to the detailed drawings provided herein. As noted above, the spatial mechanism for spinal disc prosthesis of the subject invention provides up to six-degrees-of-freedom of motion throughout the natural workspace of a functional spinal unit (FSU). The mechanism comprises at least three orthogonal prismatic joints; sagittal 17 (FIG. 19), lateral 52 (FIG. 19) and polar-axis 115 (FIG. 12); and one ball-and-socket joint 37 (FIG. 10). The ball-and-socket joint 37 provides up to three degrees-of-rotational-freedom equivalent to combined axial 95, sagittal 94, and frontal 93 plane rotations (FIG. 21). The three orthogonal prismatic joints allow arbitrary positioning in the FSU workspace.

Figure 17:
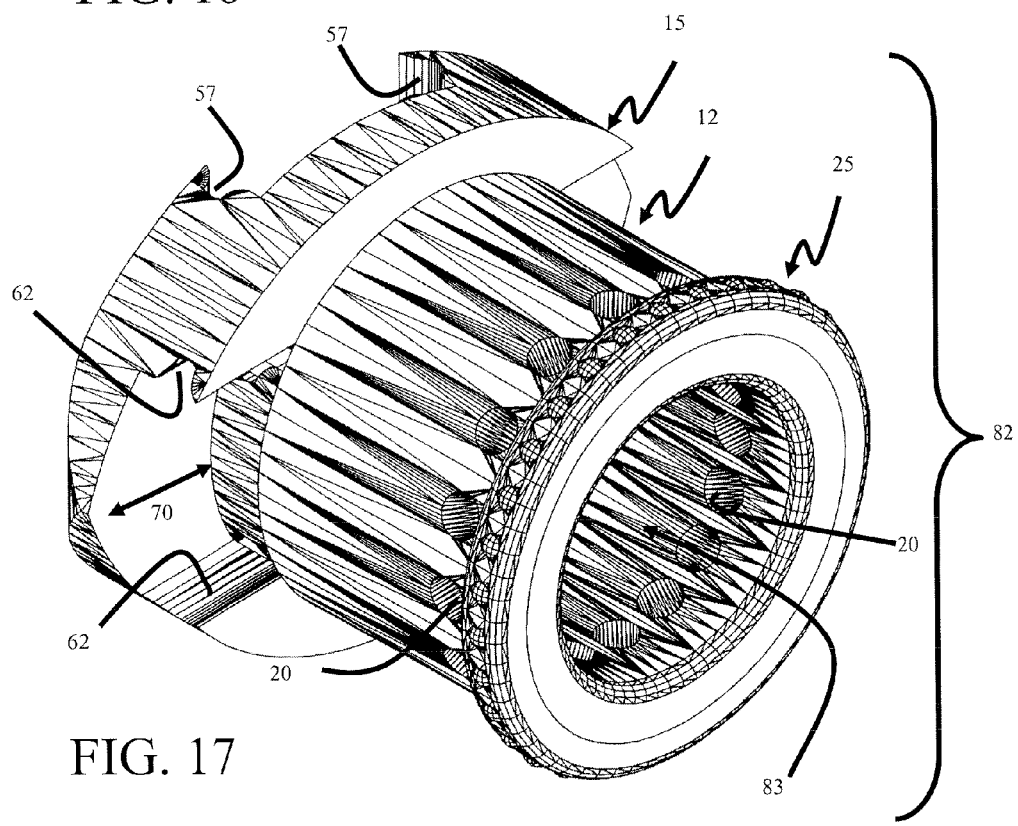
FIG. 17 shows the plane-bearing guide fitted with the piston to form the sagittal prismatic joint.

In a preferred embodiment, the device of the subject invention supports hydraulic lubrication, shock absorption, and damping. In one embodiment, a helical spring 26 (FIGS. 12, 13 and 14) may be used in conjunction with hydraulic damping to provide compression and extension loading and shock absorbing capabilities. In another embodiment, a spring can be installed into the piston cavity 83 (FIG. 17). In still a further embodiment, a boot 5, 107 (FIG. 2, FIG. 3A and FIG. 3B) provides additional torsion and extension loading response. The boot can comprise, for example, a tough, flexible, fiber reinforced elastomer matrix (FIG. 2).

FIG. 2 depicts the anterior view of a completely assembled, modular, six-degrees-of-freedom (6-DOF) spinal mechanism 1, 106 (FIG. 2) in a neutral position. The superior vertebral plate element 2 and the inferior vertebral plate element 6 fuse to the corresponding superior vertebra and inferior vertebra of the FSU in which a surgeon inserts the prosthesis. A tough, flexible corrugated boot, which can be, for example, cylindrical 5 or spherical 107 in shape, attaches to the unit with, for example, clamping rings or bands, various applicable adhesives, pins, screws, elastic means, or combinations thereof.

Figure 2A:
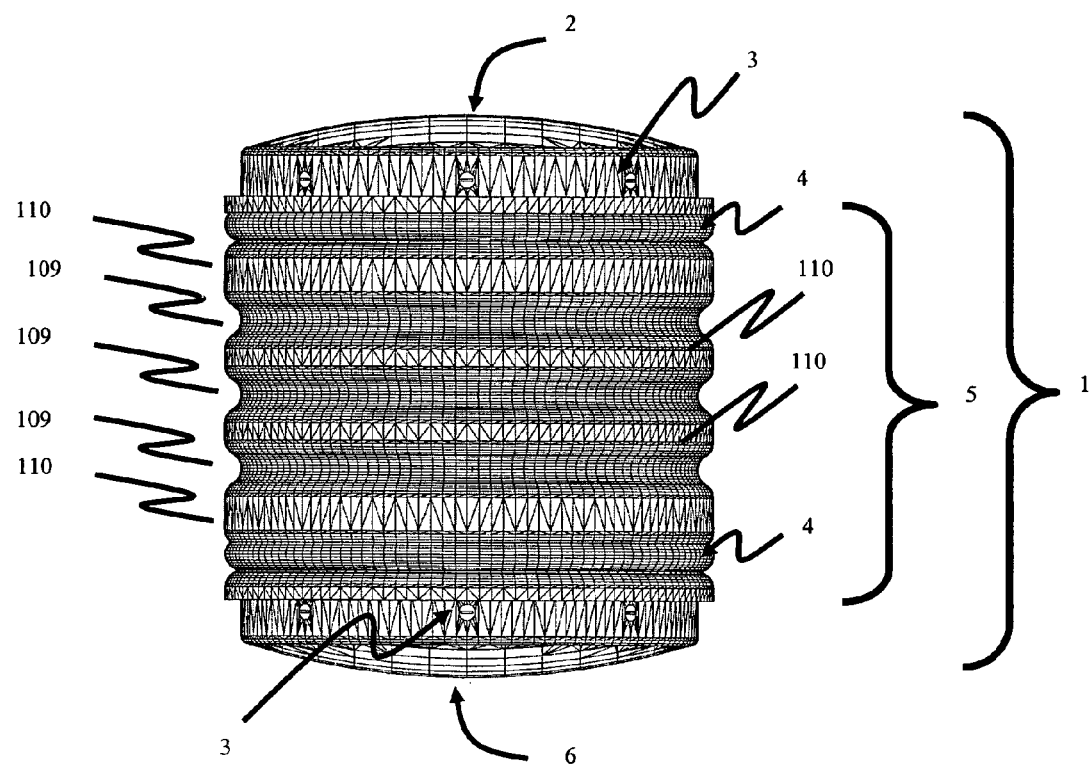
FIGS. 2A and 2B illustrate an anterior view of two versions of a completely assembled spinal disc prosthesis.
Figure 2B:
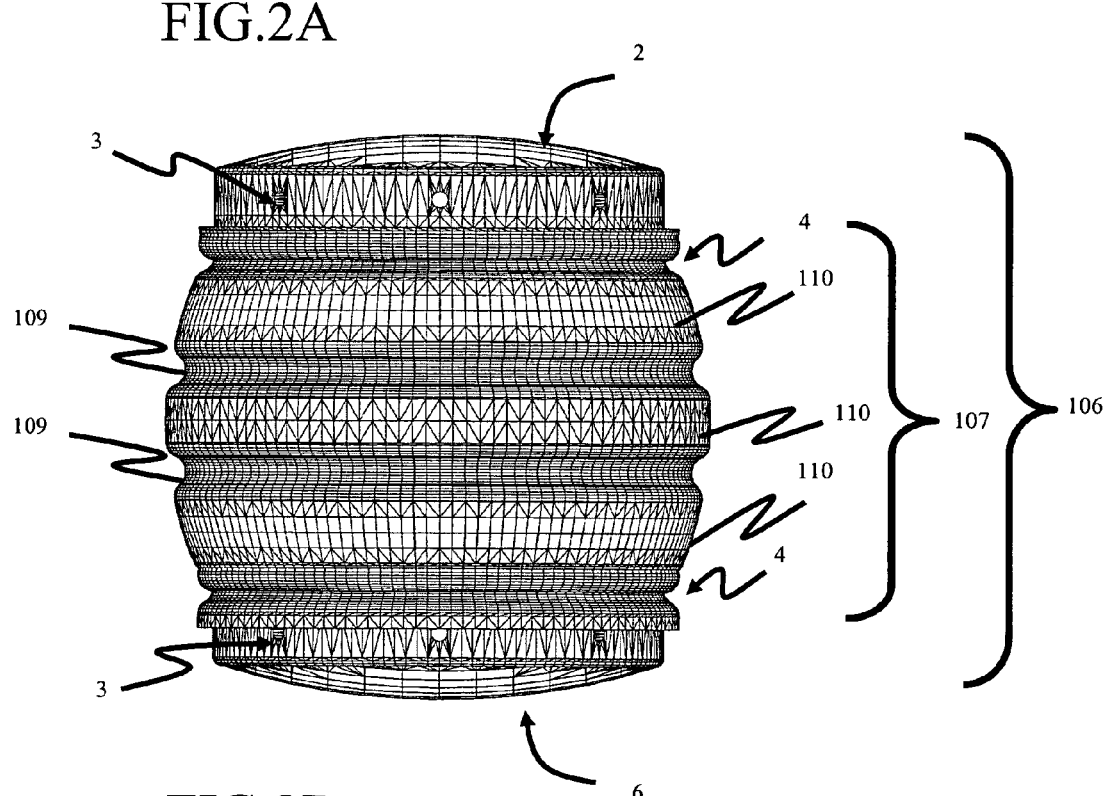

In one embodiment, the boot is fixedly attached to the device by means of clamping rings 4 FIG. 2A. In a further embodiment, the boot structure comprises a fiber reinforced diagonal weave that can be embedded into a low durometer, flexible elastomer matrix with alternating tough, thick segments 110 separated by more elastic, thinner segments 109. Between maximum flexion and maximum extension the anterior surface of the boot varies in length up to about 40% while the posterior surface varies up to about 20%. In a preferred embodiment, the boot has higher density fiber belts in regions 110 to make those regions tougher and less flexible than regions 109 (FIG. 2A, FIG. 2B). With this construction the boot is able to open and close in a billows-like fashion, yielding mobility in all directions while assisting in the maintenance of prosthesis integrity.

Figure 3A:
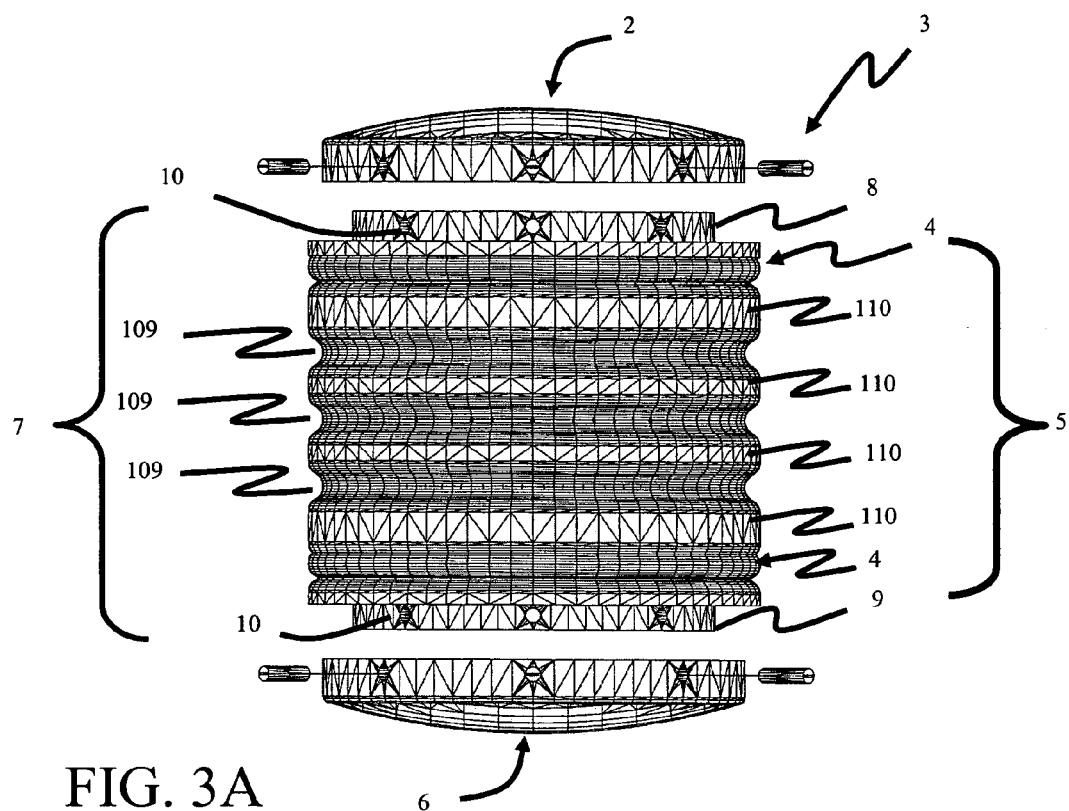
FIGS. 3A and 3B show the vertebral plates of the subject invention disengaged from the modular prosthetic disc linkage to indicate how the latter can form a replaceable, independent unit or module.
Figure 3B:
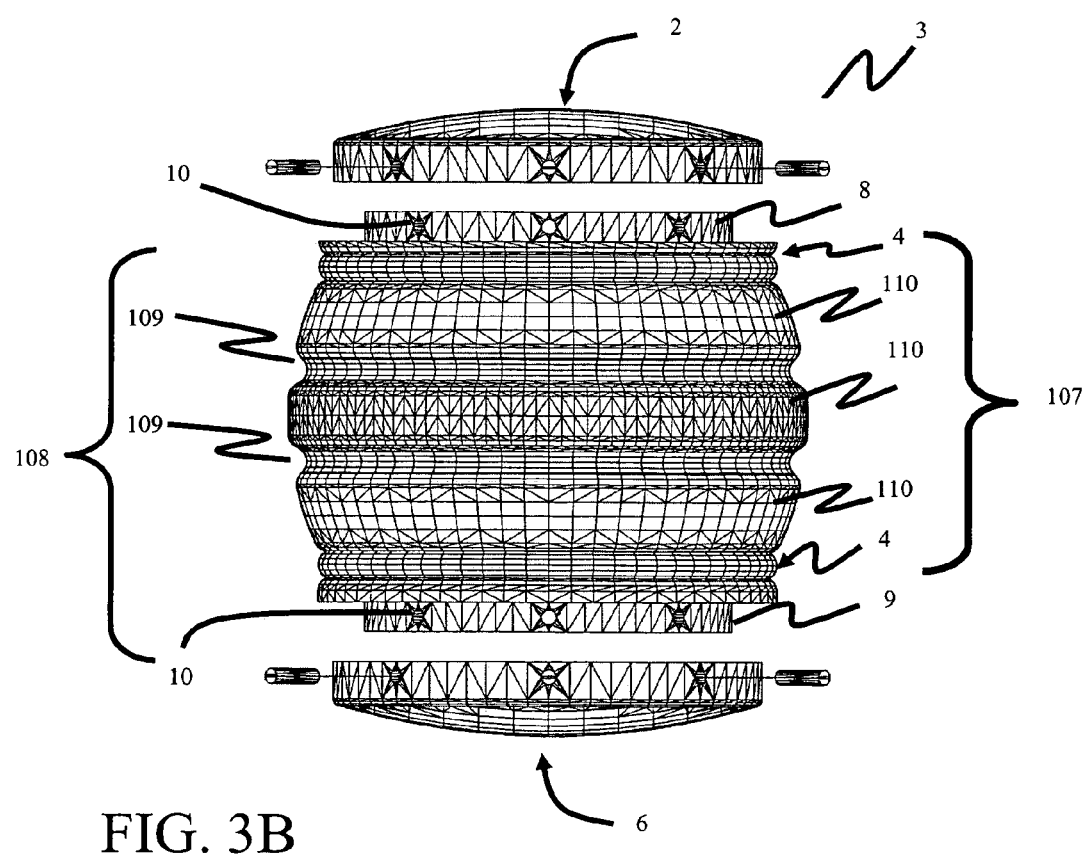
Figure 4:
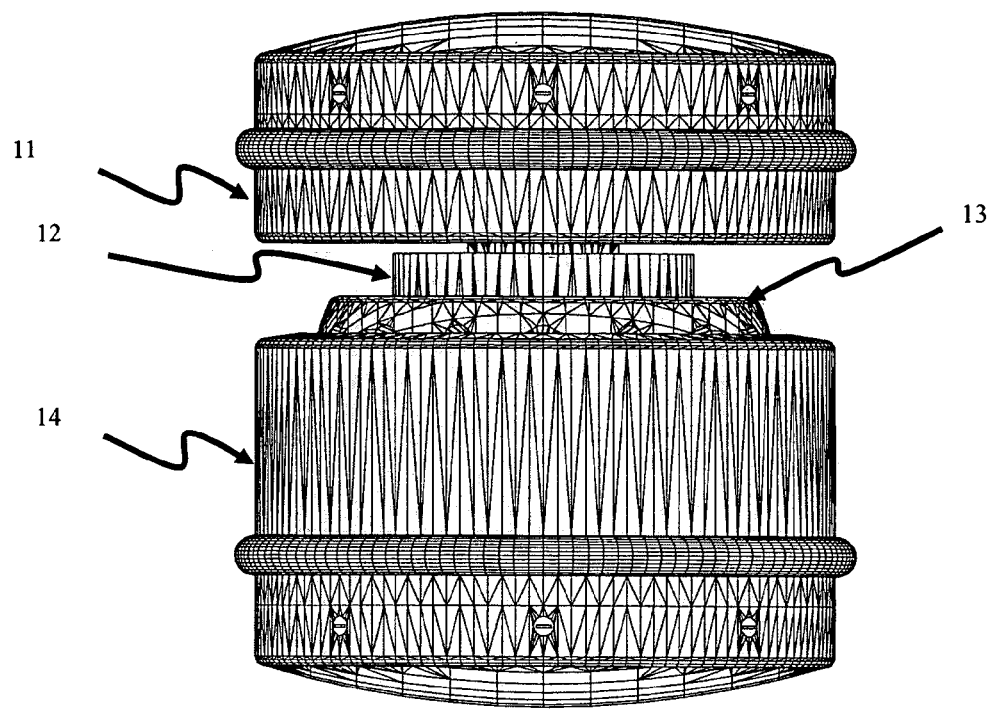
FIG. 4 shows the boot removed from the prosthesis to reveal the cap-plate, piston, chambered-ball and socket-base.
Figure 9:
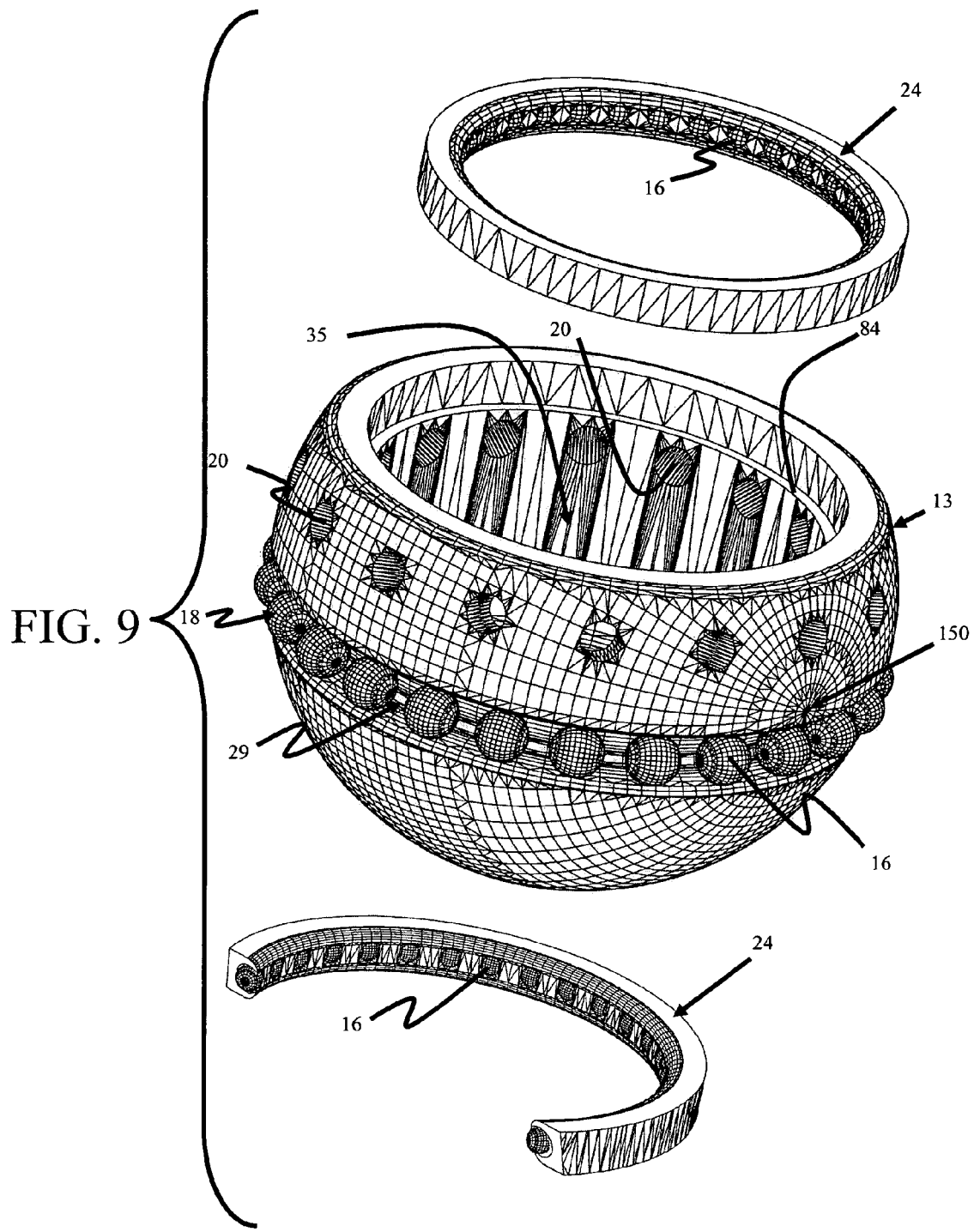
FIG. 9 shows an embodiment utilizing a spherical chambered-ball, which is slightly larger than a hemisphere with a right-circular cylindrical cavity for containing a piston. Also shown in FIG. 9 are the girdle ring-bearing and the hydraulic portals around the mouth of the chambered-ball.

FIGS. 3A and 3B highlight the modular aspect of one embodiment of the prosthesis of the subject invention: a modular prosthetic disc mechanism 7, 108 screws into, or otherwise firmly, but reversibly, attaches, to the vertebral plates 2, 6. To effect joining the modular prosthetic disc mechanism 7, 108 to the vertebral plates, one embodiment utilizes a threaded projection 8 on the cap-plate 11 (FIG. 7A) that engages with threaded lips 43 within the superior vertebral plate 2 (FIG. 6A) and threaded projection 9 on the socket-base 14 (FIG. 7A) engages with threaded lips within the inferior vertebral plate 6 (FIG. 6B). In a further embodiment, the threading on the cap-plate 11 and superior vertebral plate 2 possess opposite threading sense of the socket-base 14 and inferior vertebral plate 6 to allow screwing the modular prosthetic disc mechanism 7, 108 into both vertebral plates simultaneously with the same turning action FIG. 4, with the boot 5 (or 107) removed, reveals an anterior view of the cap-plate 11, socket-base 14, and partial views of the piston 12 and chambered-ball 13. Removal of the cap-plate 11 and socket-base 14 in FIG. 5 further exposes the spherical chambered-ball 13 and a further element, the plane-bearing guide 15. In one embodiment, the chambered-ball 13 possesses hydraulic portals 20 in a circle of latitude above the equator near the mouth of the chambered-ball cavity 35 (FIG. 9). In a further embodiment, there are four other hydraulic portals 20 at the base of the chambered-ball 13 (FIG. 10). In yet a further embodiment, the four hydraulic portals are distributed 90 degrees apart at the base of the chambered-ball. These hydraulic portals 20 allow the passage of fluid in and out of the chambered-ball cavity to lubricate the bearing surfaces, contact points and lines as the ball rotates.

The superior 2 and inferior 6 vertebral plates (FIG. 6) of the device may be identical in structure and composition. In one embodiment, at least one surface of a vertebral plate is convex 38, further comprising a recessed, flat underside 39 (FIG. 6B) with a rim or lip 40. The cavity 44 of each vertebral plate matches the threaded mounting extensions of the cap-plate 11 and the socket-base 14. Threads on the inside surface of the lip 43 possess a different turning sense on the superior 2 and inferior 6 vertebral plates so that the superior plate 2 screws onto the cap-plate 11 and the inferior plate 6 screws onto the socket-base 14 with the same turning motion. One or more, preferably three, through-holes 41 in the anterior surface of each vertebral plate rim 40 allow for the insertion of, for example, lock-and-align screws 3 through the rim of the plates. These screws fasten into the threaded holes 10 (FIG. 7A) on the cap-plate 11 and socket-base 14.

In a further embodiment, central-anterior through-holes on the superior and inferior vertebral plates define a line that lies in the sagittal midline plane. The angle of that line with its projection onto the horizontal plane facilitates orientation of the prosthesis in the FSU. The x-y coordinates of the chambered-ball center in the sagittal midline plane, is dictated by the geometry of the FSU utilizing the prosthesis. With the lock-and-align screws in place, the modular prosthetic disc mechanism 7, 108 is properly oriented with respect to the vertebral plates 2, 6.

In one embodiment, the vertebral-plate has a roughened spherical surface 38 and consists of titanium alloy with a porous matrix for bone infusion. The spherical center and solid angle subtending the spherical surface are, in a preferred embodiment, alterable design parameters that dictate the size of the vertebral top surface. In a further embodiment, the vertebral plates comprise cobalt-chromium-molybdenum alloy with vertical teeth as well as a porous mesh on the spherical surface to further enhance bone infusion and mechanically securing the plates to bone.

Figure 8:
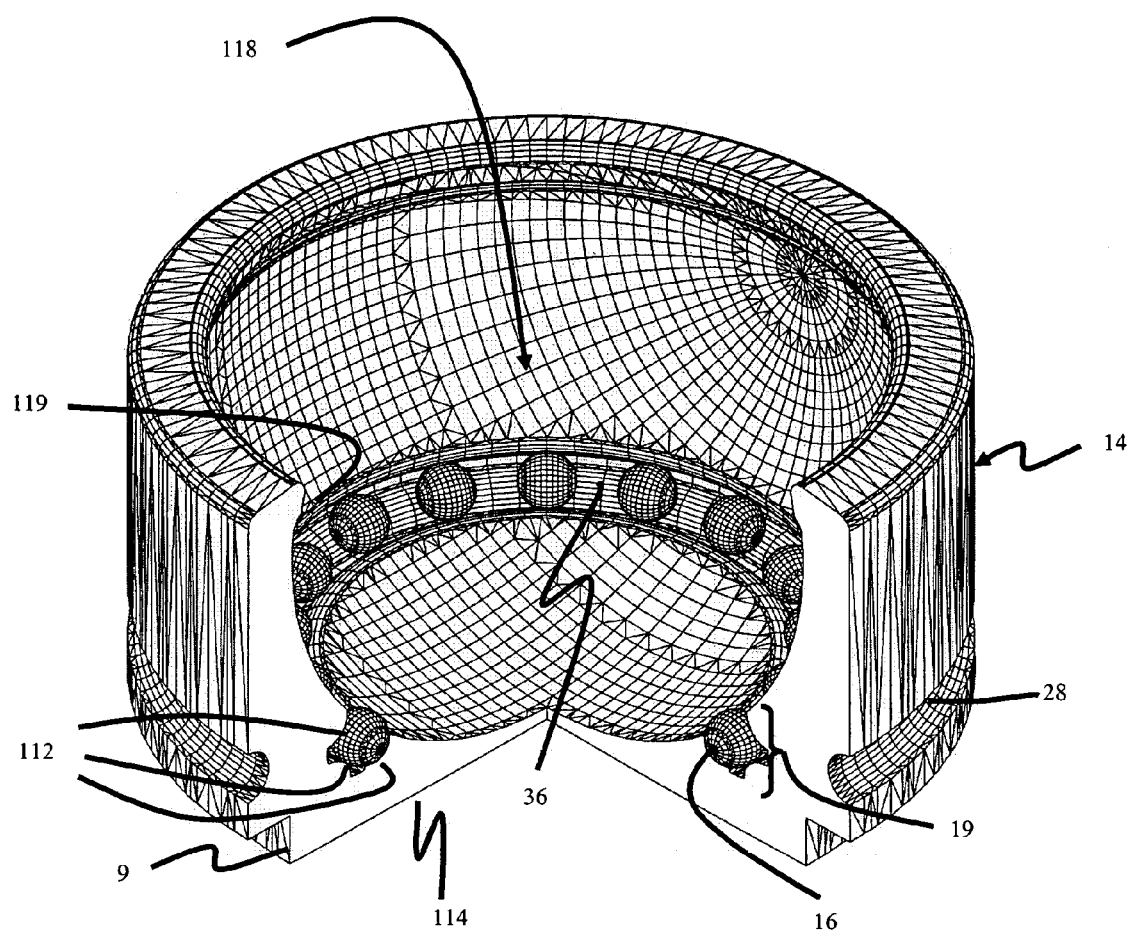
FIG. 8 is a cut-away view of the socket-base, which reveals the spherical cavity that, in a preferred embodiment, contains the chambered-ball. The socket ring-bearing supports the chambered-ball and can reduce friction between the ball and socket.

A non-reactive, biocompatible liquid gasket may be applied to one or more threaded surfaces, for example surfaces 8, 9, and 10 and other interface surfaces before mating the modular prosthetic disc mechanism 7, 108 with the vertebral plates 2, 6 in order to seal and protect elements of the prosthesis from chemical reaction with the bioenvironment. The interface surfaces consist of 1) the recessed, flat section of the superior vertebral plate 39 and the flat surface on top of the cap-plate 51 (FIG. 18B) and 2) the recessed flat portion of the inferior vertebral plate 39 and the flat bottom of the socket-base 114 (FIG. 8). The utilization of gasket seals protects the interfaces and threads from corrosion, degradation, and molecular bonding, making modularity of the modular prosthetic disc mechanism realistic.

Below are specific examples of the design, construction and/or operation of various components of the system of the subject invention. These examples should not be construed as limiting.

EXAMPLE 1

Ball-and-Socket Joint

In one embodiment, the chambered-ball 13 (FIG. 9) fits into the spherical cavity 118 of the socket-base 14 (FIG. 8) to form a ball-and-socket joint 37 (FIG. 10). In a preferred embodiment, the ball is free to rotate about three orthogonal axes 93, 94, and 95 (FIG. 14) within the socket cavity. Thus, in one embodiment, the ball-and-socket joint allows the spatial mechanism to arbitrarily orient or point in three-dimensional space, within the angle limits of the linkage, the more distal elements of the device: the piston 12, plane-bearing guide 15, cap-plate 11, and superior vertebral plate 2. In the lower pair embodiment, FIG. 28, the elements 214, and 213 form a spherical kinematic pair, i.e., the ball-and-socket joint.

Figure 5:
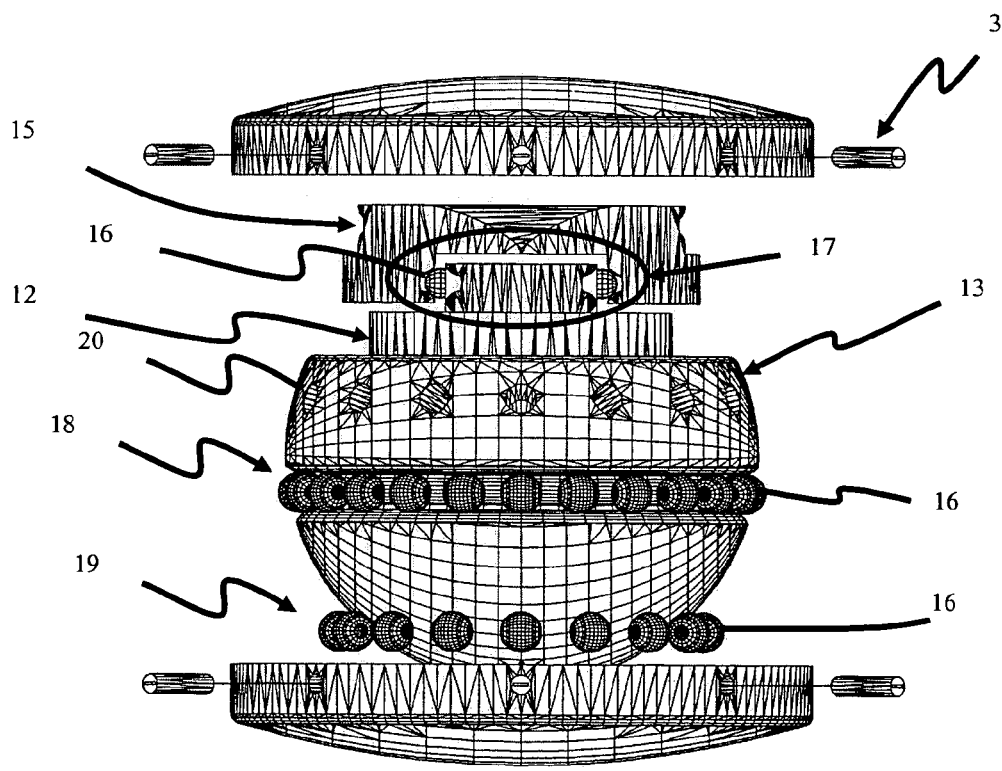
FIG. 5 further illustrates the subject invention with the cap-plate and socket-base removed to further reveal the spherical shape of the chambered-ball and to expose the plane-bearing guide that can be used to support the lateral and sagittal prismatic joints of the mechanism. The figure also exposes the girdle and socket-base ring-bearings.
Figure 6A:
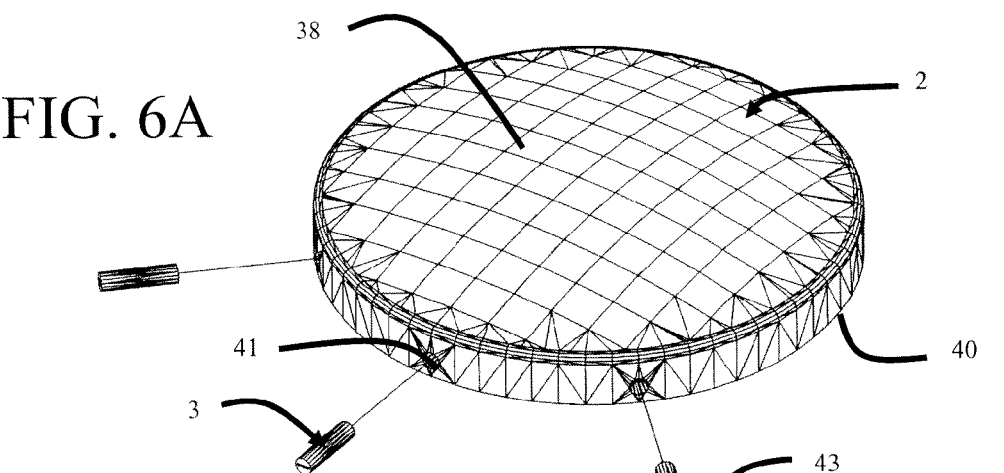
FIGS. 6A and 6B are illustrations of a preferred embodiment of the superior vertebral plates (FIG. 6A) and the inferior vertebral plate (FIG. 6B) of the subject invention. Illustrated is the threading of the elements and the locking screws by which they can be attached to the modular prosthetic disc mechanism.
Figure 6B:
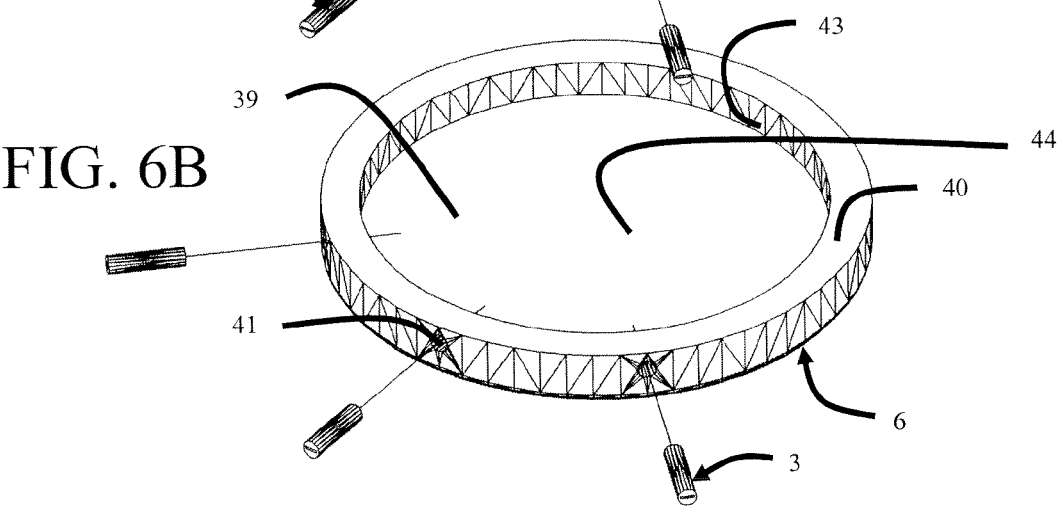

In an alternative embodiment, a girdle ring-bearing 18 and a socket ring-bearing 19, illustrated in FIG. 5, can be utilized with the ball-and-socket joint. FIG. 5 does not illustrate bearing separators and retention matrices that may be utilized in yet a further alternative embodiment, for these particular bearings. In one embodiment, bearing separators and retention matrices are not used, allowing the bearings to move freely within the raceways. In alternative embodiments, interlocking mechanical constraints can prevent the bearings from leaving their raceways.

In one embodiment, the girdle ring-bearing raceway 29 and the socket ring-bearing raceway 36 (FIG. 10) are within the chambered-ball and socket-base respectively. A variety of cross sections can be employed for these raceways. In one embodiment, three bearing contact points 112 (FIG. 10) maintain ball-bearings within the raceways. These ring-bearings, in an alternative embodiment, can comprise separate, complete ring-bearing units that install in seats within the chambered-ball 13 and socket-base 14. These bearings can have a variety of cross-sections, contact points, lubrication tracks and materials, for example, but not limited to, polyurethane, or titanium-hardened-stainless steel alloys. Refer to FIGS. 23A and 23B and FIGS. 24A and 24B for illustrated examples of alternative bearing embodiments.

In an alternative embodiment, the surface bearings in the lower kinematic pair joints of FIG. 28 may comprise for example, high molecular density polyethylene or thermoplastic. In still a further alternative embodiment, the cap-plate 211, piston 212 and the socket-base 214 comprise of, for example, titanium steel.

As illustrated in FIG. 9, the girdle ring-bearing 18 surrounds the chambered-ball 13 in a circle of latitude near, but below the figurative equator 150 (FIG. 9). The socket ring-bearing 19, FIG. 5 (shown as loose bearings suspended in space), and FIG. 8 can be embedded 36 (FIG. 10) into the spherical cavity of the socket-base 14 and in a preferred embodiment, do not move or rotate with the chambered-ball 13 as can the girdle ring-bearing 18. In one embodiment, the ball-bearings 16 in the socket ring-bearing 19 contact the chambered-ball surface at the intersection of that surface and the line between the ball-bearing center and the common center of the chambered-ball 35 and socket cavity 118. In still a further embodiment, each ball-bearing 16 in the girdle ring-bearing 18 (FIG. 9) contacts the socket-base surface at the intersection with that surface of the extended line between the ball-bearing center and the common center of the chambered-ball and socket cavity.

Thus, in one embodiment, the socket ring-bearing 19, 36 provides support (FIG. 10) for the chambered-ball 13 and transmit contact forces to the socket-base 14, and thence to the inferior vertebral plate 6 and inferior vertebra of the FSU into which the inferior vertebral plate 6 fuses. In a further alternative embodiment, the girdle ring-bearing 18, 29 (FIG. 9) supports the chambered-ball, transmits load forces to the socket, and moves with the chambered-ball as it orients the upper elements of the prosthesis during spinal motion.

In summary, the socket 19, 36 and girdle 18, 29 ring-bearings provide separate regions of support for the chambered-ball to prevent jamming and aid in smooth ball-and-socket joint action.

EXAMPLE 2

Polar-Axis Prismatic Joint

The polar-axis prismatic joint can comprise the combination of the spherical chambered-ball 13 (FIG. 9) and the cylindrical piston 12 (FIG. 11) to form a prismatic pair. In one embodiment, the prismatic pair also comprises bearings 24 and 25. In a further embodiment, the cross-section of the chambered-ball cavity 35 is similar or identical to the piston cross-section, but should possess slightly greater radius of curvature to accommodate the piston and allow for bearing clearances. In the lower pair embodiment as illustrated in FIG. 28, the elements 213, and 212 form a cylindrical pair to provide a polar-axis prismatic joint.

Figure 14:
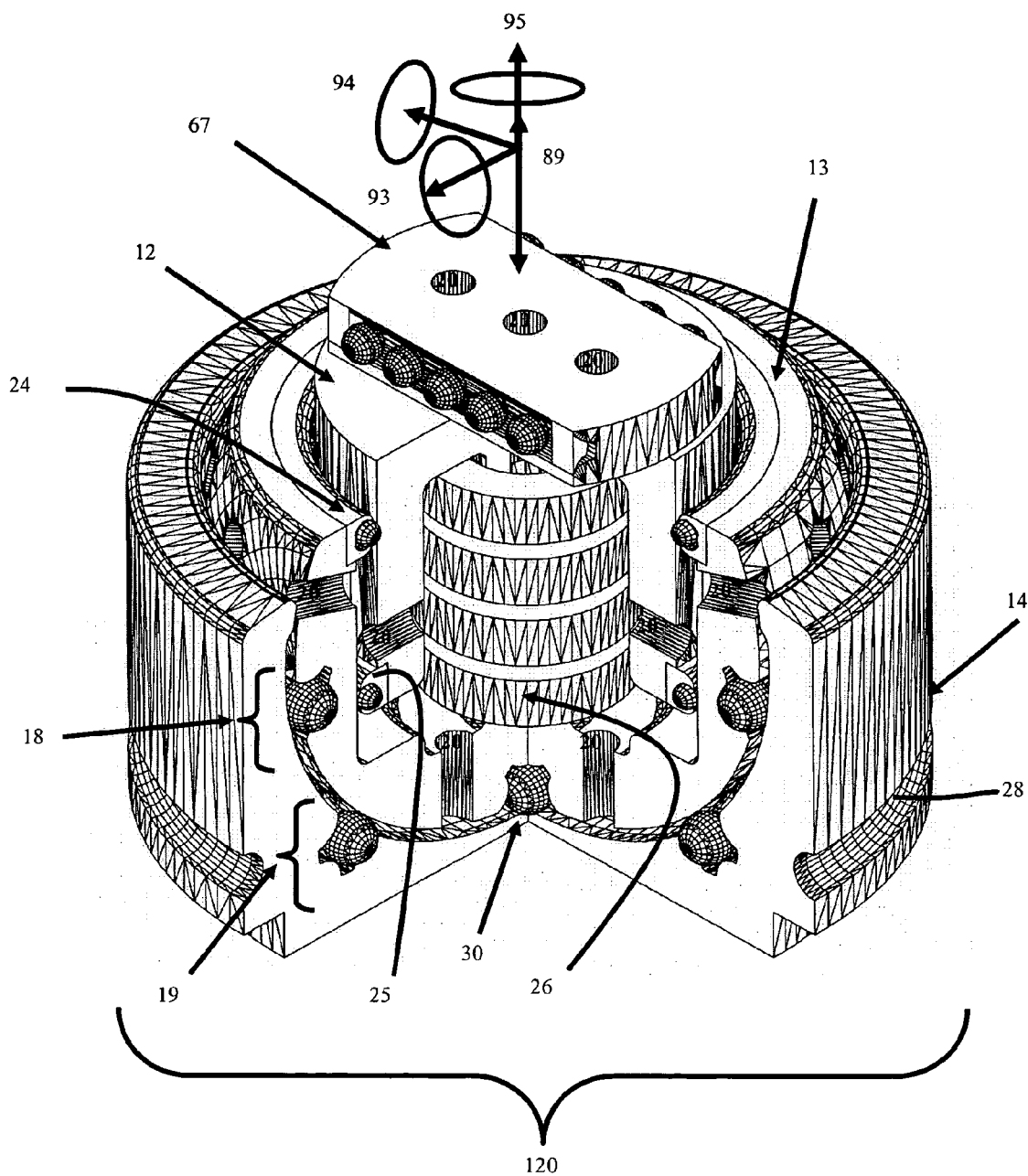
FIG. 14 illustrates the piston, inserted within the chambered-ball, which is positioned within the socket-base. This configuration enables a 4-DOF spherical-polar-axis linkage that orients and projects, or retracts, the piston. The installed helical spring opposes compression and extension loads.
Figure 22:
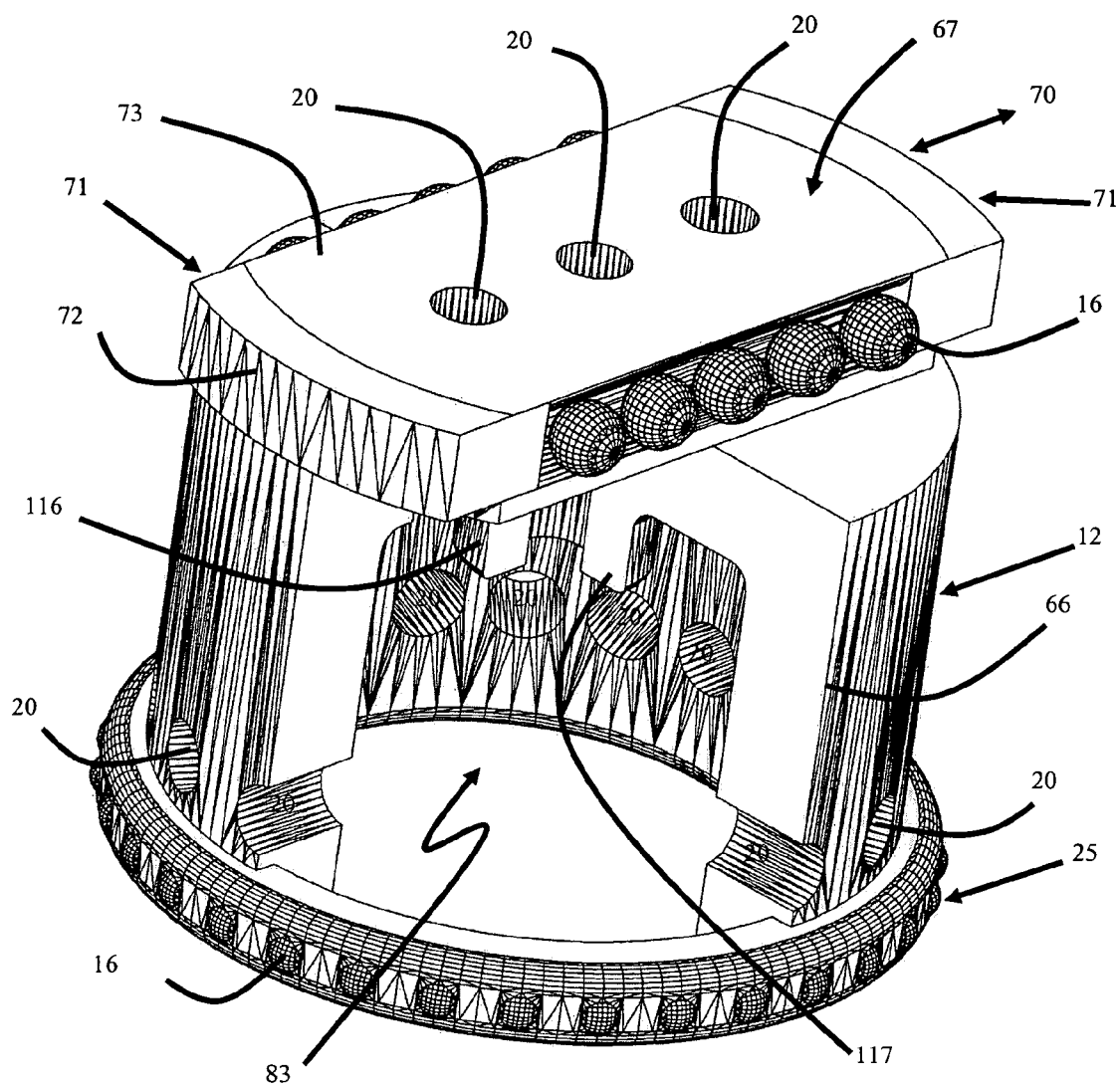
FIG. 22 demonstrates the use of oversized sagittal bearing-stops on the piston, a form of mechanical programming of the sagittal angle limits. The cut-away opens up into the piston cavity and reveals the spring mounting post at the center-top of the cavity.

Hydraulic portals 20 circle the mouth of the chambered-ball 13 to allow lubricating fluid to flow out of the chambered-ball cavity 35 to other moving parts. Four hydraulic portals 20 may pierce the bottom, circling a polar bearing 30 (FIG. 10, FIG. 12) that can be positioned in the base of the chambered ball The piston 12 (FIG. 11, FIG. 22), in one embodiment, comprises a right-circular cylinder 66. In yet a further embodiment, the piston has a cylindrical cavity 83 to contain, for example, a spring, elastomeric device, or other shock absorbing material 26 FIG. 12. The lower element of the sagittal prismatic joint 67 (FIG. 11) with lateral bearing raceways 21, which may be machined, sits on top of the piston. One or more bearing stops 22 may be placed, for example by welding or pressure fitting into the two raceways 21, preferably one at each end, after bearing insertion. The lower element 67 of the sagittal prismatic joint, in a preferred embodiment, is fixedly attached on the top of the piston (FIG. 11, FIG. 14 and FIG. 22). The lower element of the sagittal prismatic joint 67 may consist of the same material as the piston 12. Alternative embodiments may utilize different materials for these two elements. But, in a preferred embodiment these two elements are rigidly joined.

Figure 16:
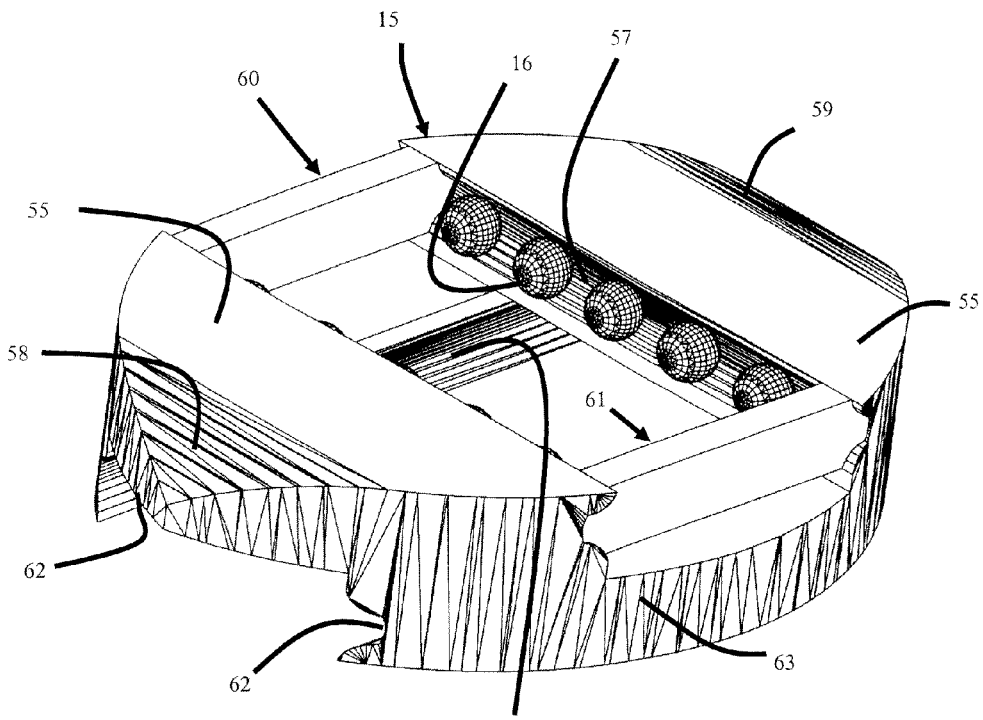
FIG. 16 illustrates the plane-bearing guide to show the complex surfaces and shapes involved, and reveal bearing and bearing-stop placement. The plane-bearing guide supports two, orthogonal, dual-track raceways that help realize the sagittal and lateral prismatic joints of the spatial mechanism.

In an alternative embodiment, one or more bearing stops 22 (FIGS. 11 and 12) are utilized to retain the bearings in the sagittal raceways 21 when the lower half of the sagittal prismatic joint 67 links (as shown in FIG. 17) with the plane-bearing guide 15 (FIG. 16). In one alternative embodiment, bearing stops are utilized at either end of the raceways. In still a further alternative embodiment, the bearing stops are not inhibited by the plane-bearing guide 15 and do not interfere with joint motion. In alternative embodiments, the lateral surface 69 (FIGS. 11 and 12) of sagittal joint element 67 may not extend the full radius of the piston cylinder, but is slightly recessed to provide a seat for oversized bearing stops 71, 72 (FIG. 22). In further alternative embodiments, a recess may not be required and the bearing stops, whether oversized or not, may be integrated as part of element 67.

Sagittal bearing stops should contact the cap-plate as a hard joint stop, restricting joint travel in flexion and/or extension. In this manner, flexion and extension limits may be independently controlled.

Figure 19:
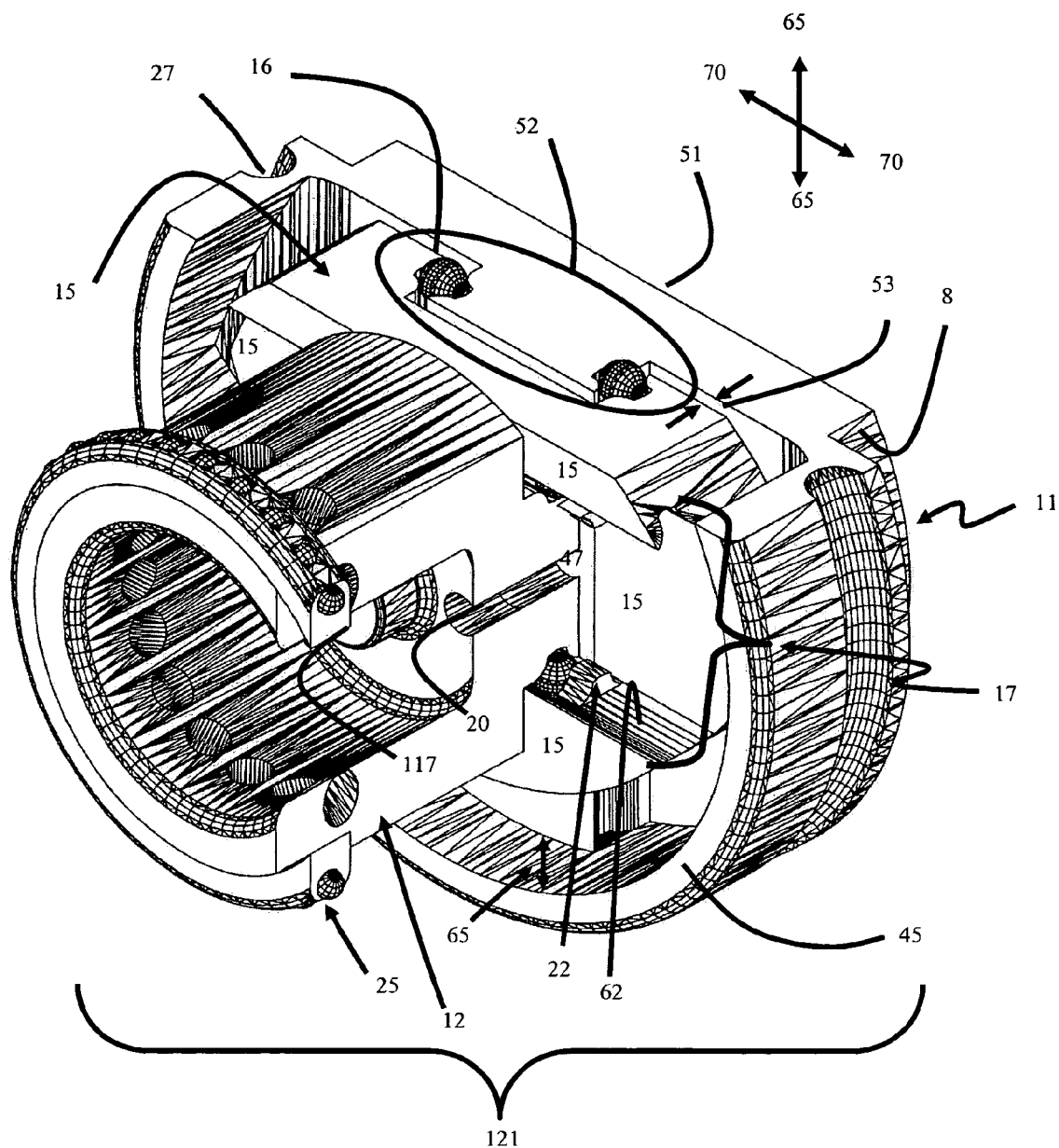
FIG. 19 shows the combined cap-plate, plane-bearing guide and the piston to realize a 2-DOF linkage for motion in the superior vertebral-plane. This cut-away view reveals the lateral and sagittal prismatic joints and their configuration within the plane-bearing guide. The lateral prismatic joint, circled at the top of the figure, allows the piston and plane-bearing guide to move "up and down" ("left to right", i.e., laterally, when installed) with respect to the cap-plate while the sagittal prismatic joint allows the piston to move "left and right" ("fore and aft", i.e., sagittally, when installed) with respect to the plane-bearing guide and the cap-plate. During pure sagittal prismatic joint motion, the plane-bearing guide and cap-plate do not undergo any relative motion with respect to each other.

The piston ring-bearing 25 (FIG. 11) may be press fit or otherwise firmly attached to the seat 68 (FIG. 7A, FIG. 11) at the base of the piston 12 (as shown in FIG. 17). In one embodiment, just above the piston ring bearing seat 68 is a circle of hydraulic portals 20 (FIGS. 7A and 12) within the lateral surface of the piston 12 which lead into the piston cavity 83 (FIGS. 17 and 22). In a further preferred embodiment, three additional hydraulic portals 20 within the top of the piston 12 lead into the piston cavity 83 (FIG. 22). In a preferred embodiment, these hydraulic portals allow lubricant, or other fluids within the boot cavity, to pass to the sagittal prismatic joint 17, 82 (FIG. 5, FIG. 17) and the lateral prismatic joint 52 (FIG. 19).

Figure 7A:
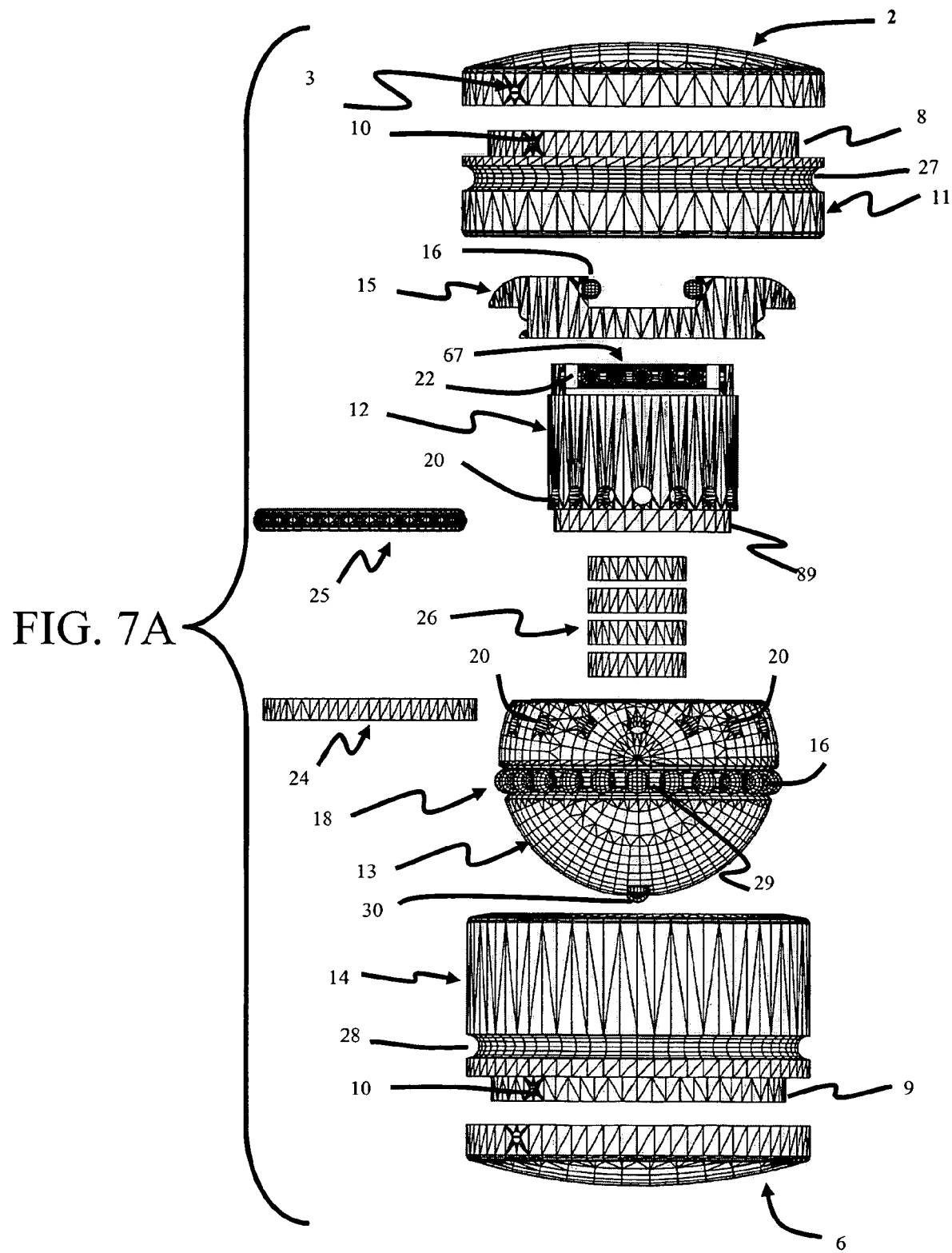

A further embodiment utilizes hydraulic portals 20 on top of the piston 67 and around the base of the piston, just above the piston ring-bearing seat 68, to allow fluid to flow between the inner cavity 83 of the piston and the rest of the prosthetic mechanism encased and sealed by the boot. In a preferred embodiment, as the piston 12 moves in and out of the chambered-ball cavity 35 to match the required intervertebral gap as required by the movement of the FSU, it can also function as a hydraulic pump. The hydraulic portals 20 circling the bottom of the piston 12 above the piston ring-bearing 25 provide an outlet from the piston cavity 83 of hydraulic fluid sealed inside the prosthetic by the boot, even at maximum flexion and extension of the piston 12. Fluid pumped through hydraulic portals 20 at the base of the piston 12 can pass into a cavity between the piston 12 and the chambered-ball 13 and lubricate the piston and chambered-ball ring-bearings 25, 24. Compression of the piston 12 during FSU movement can also force fluid between the piston and the chambered-ball into the ball-and-socket bearing gap, lubricating the chambered-ball and socket-base ring-bearings 18, 19 and the polar bearing 30 (FIG. 7A, FIG. 10). Fluid flowing out of the bottom of the chambered-ball cavity 35 can also perform this function. Fluid forced out of the hydraulic portals 20 that penetrate the piston top into the piston cavity 83 can automatically lubricate the sagittal and lateral prismatic joints 17, 52 during normal operation of the FSU. In a preferred embodiment, the prosthesis is able to automatically lubricate most or all of the bearing surfaces, points and lines of the spinal disc prosthesis during normal operation.

In other embodiments, the piston 12 can be a variety of, preferably hollow, prismatic shapes, preferable right angled, with arbitrary cross-section shape, preferably, though not limited to, a simple convex curve, with a variety of desired cavities therein. In a preferred embodiment, the piston can slide in and out of the chambered-ball to provide an equivalent of the polar-axis prismatic joint 115 and a piston cavity similar to 83 (FIG. 17) to allow installation of an effective spring, or spring-like,-damping system and to enable hydraulic pumping action.

The piston ring-bearing 25, shown separated from the piston in FIG. 11, may be press fit or welded to the seat 68 and, in one embodiment, forms an integral part of the polar-axis prismatic joint 115 consisting of the piston 12 sliding in and out of the chambered-ball 13 (FIG. 12). The chambered-ball ring-bearing 24 and the piston ring-bearing 25, revealed by the cutaway in FIG. 12, prevent the outside piston surface 66 from engaging the surface of the chambered-ball cavity 35 except through ball-bearings. In a further embodiment, the piston ring-bearing 25 ball-bearings face radially outward and contact the inner surface of the chambered-ball cavity 35 while the chambered-ball ring-bearing 24 ball-bearings 16 face radially inward to contact the outside surface 66 of the piston 12. This provides the bearing mechanism of the polar-axis prismatic joint 115.

The ring-bearing dimensions, can depend upon the application sizing of the mechanism, and place an upper bound on the number and size of the ball bearings. After placement of the piston 12 and spring 26 into the chambered-ball 13 to realize the polar-axis prismatic joint 115 (FIG. 12), the chambered-ball ring-bearing 24 may be press fit or otherwise fixedly attached to the mouth of the ball's cavity. In one embodiment, the ring-bearing 24 is fixedly attached to a seat 84 in the mouth of the ball's cavity 35 (FIG. 9). In a further embodiment, it is the placement of the ring-bearing 24 that secures the piston into the cavity 35 of the chambered-ball. Together, the chambered-ball and piston ring-bearings 24, 25 provide smooth piston motion 89 in and out of the chambered-ball cavity 35 along the polar axis 113 of the ball (FIG. 10, FIG. 12). The central axis 113 of the chambered-ball 13 rotates with the ball as it moves in the socket-base. This rotating axis defines the direction of piston motion 89 of the polar-axis prismatic joint 115 (FIG. 12). In a preferred embodiment, the polar-axis prismatic joint 115, enables telescoping of the piston 12 in and out of the chambered-ball cavity 35 to match the required intervertebral gap currently demanded by the position of the FSU.

EXAMPLE 3

Spherical-Polar-Axis Linkage

In one embodiment, linking the piston 12, with a spring 26, chambered-ball 13, and socket-base 14 provides a 4-DOF spherical-polar-prismatic manipulator with load bearing capacity (FIG. 14). As the more distal elements of the prosthesis, i.e., the plane-bearing guide 15, cap-plate 11, and superior vertebral plate 2, move, the spherical manipulator (ball-and-socket joint) track their orientation 93, 94, 95 and distance traveled 89 along the polar axis 113 (FIG. 10) from the chambered-ball center.

Figures 15A, 15B, 15C:
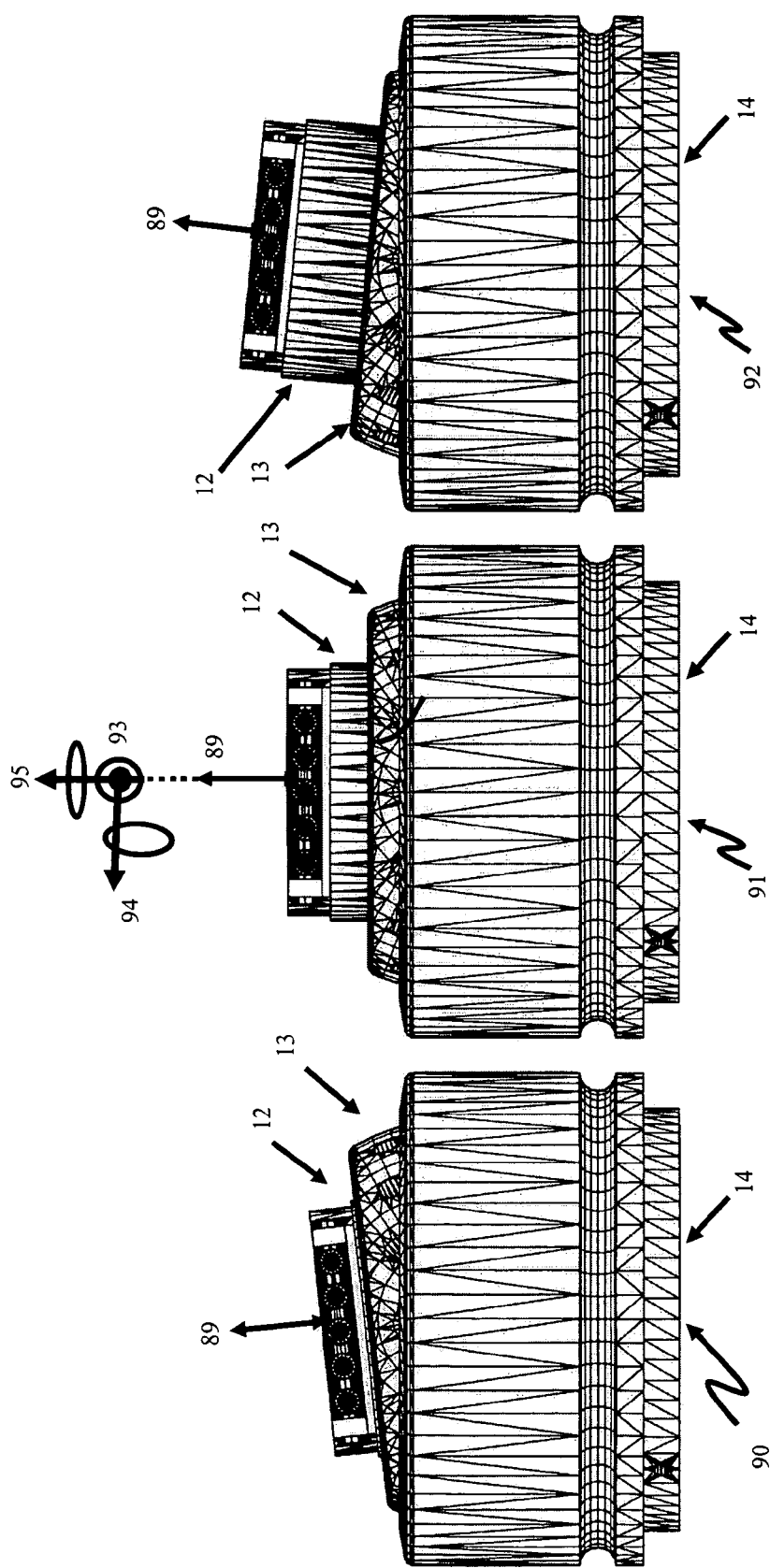
FIGS. 15A, 15B, and 15C illustrate, from left-lateral view, the 4-DOF spherical-polar-axis linkage manipulating the piston to achieve a final position and orientation in flexion (FIG. 15A), neutral (FIG. 15B) and extension (FIG. 15C).

FIGS. 15A, 15B and 15C show the operation of the spherical-polar-axis linkage 115 in flexion 90, neutral 91 and extension 92. As spinal muscles move the superior vertebra of the FSU, loading on the spring or spring-like mechanism or material within the piston changes. In a further embodiment, the principal spring axis coincides and, thus, rotates with, the polar-axis 113, causing the forces acting on the spring to either rotate the spring by means of the ball-and-socket joint or engage the spring along its principal axis. FIGS. 15A, 15B and 15C also indicate the relative, nominal orientations of the chambered-ball for vertebrae C2-C3 in the three configurations.

EXAMPLE 4

Sagittal Prismatic Joint

In one embodiment, the plane-bearing guide 15 (FIG. 16) in conjunction with the piston 12 creates the sagittal prismatic joint 17, 82 (FIG. 5, FIG. 17). FIG. 19 illustrates a cut-away of this joint along with the lateral prismatic joint. In one embodiment, the joint movement 70 tracks along raceways 62 of the plane-bearing guide 15, between the anterior 58 and posterior 59 poles of the plane-bearing guide 15. The plane-bearing guide 15 (FIG. 16) supports two orthogonal, dual-track raceways, one dual-track raceway for lateral bending 57 and one for sagittal flexion-extension 62 of the prosthetic disc linkage. In a further embodiment, there are downward, pointed, compound-curved surfaces anterior 58 and posterior 59 to the plane-bearing guide that allow more structural material for the guide and the cap-plate than would otherwise be possible. One or more lateral bearing stops 60, 61 can be, for example, pressure fitted or welded into the raceway and prevent the bearings from leaving the raceway of the lateral prismatic joint 52 (FIG. 19).

A frontal view of a preferred embodiment of the sagittal prismatic joint 17 in FIG. 5 illustrates how the bearings 16 interlock the plane-bearing guide 15 to the sagittal bearing support 67 (FIG. 11) that is fixedly attached to, or can be manufactured as an integral part of, the piston 12. In this embodiment, the sagittal prismatic joint facilitates the superior vertebral plate 2, the cap-plate 11 and the plane-bearing guide 15 to slide along the axis of the joint. Since the piston 12 rotates with the chambered-ball 13 as the device accommodates muscle commands, the sagittal prismatic joint line of action rotates in space as dictated by FSU movement.

In one embodiment, the lower tracks of the plane-bearing guide slidably connect with the piston linear bearing guides to form the sagittal prismatic joint 17, 82 (FIG. 5, FIG. 17). In alternative embodiments, ball-bearings of, for example, titanium steel, or, in a further embodiment, rod-bearings of different cross-section and material composition (FIGS. 23A, 23B, and FIGS. 24A and 24B), are positioned in the sagittal bearing raceways and can lock the two pieces together. The rod bearings can also be formed or integrated directly into the contact surfaces of the joint. Thus, in a further alternative embodiment, the surface of the plane-bearing guide 15 does not contact the top surface of element 67 on top of the piston 12. Thus, in this embodiment, the only contact between the two elements should be through the sagittal raceway bearings.

To increase the rigidity of the joint so that it is able to support greater loads, a further embodiment incorporates bearings distributed on the top surface of element 67 of the piston. For example, two bearing raceways may be provided on the top surface of 67, parallel to raceways 62. In a preferred embodiment, the piston 12 and plane-bearing guide 15 typically move 70 with respect to each other only along the sagittal prismatic joint 17, 82 (FIG. 5, FIG. 17). At extremes of the sagittal prismatic joint movement 70, the piston should not, in a preferred embodiment, contact the rim 45 of the cap-plate 11. In one embodiment, as illustrated in FIG. 28, the elements (212, 215) form a prismatic pair for the sagittal prismatic joint and uses only surface bearings. This arrangement provides the greatest load-bearing and greatly simplifies the joint, eliminating all roller and rod bearings.

EXAMPLE 5

Lateral Prismatic Joint

The lateral prismatic joint 52 (FIG. 19) comprises the linking of the bearing raceways 49 of the lateral bearing support 47 of the cap-plate 11 (FIGS. 18A and 18B) with the upper bearing raceways 57 of the plane-bearing guide 15 (FIG. 16). In one embodiment, the guide 15 moves laterally 65 (FIG. 19) along the raceways with respect to the cap-plate. Thus, in a preferred embodiment, it is the lateral prismatic joint 52 that facilitates lateral translations. In the lower pair embodiment, FIG. 28, the elements (215, 211) form a prismatic pair for the lateral prismatic joint, providing greater strength and load carrying capacity, as well as bearing simplification.

Figure 18A:
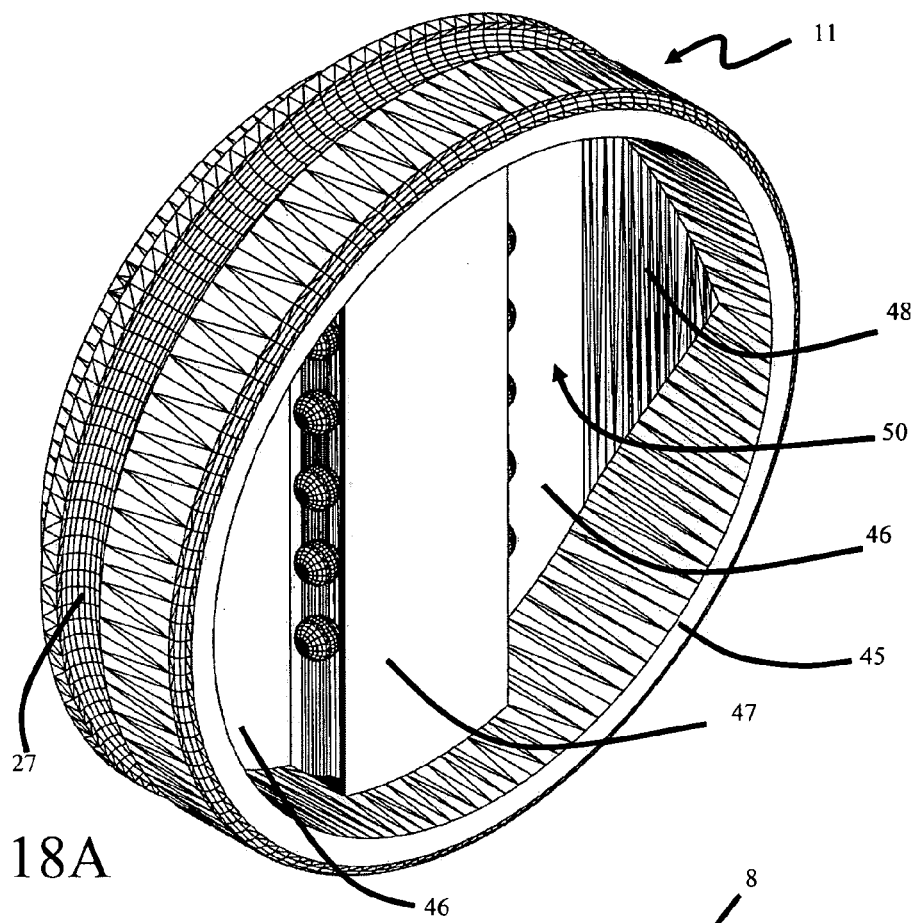
FIGS. 18A, and 18B show the underside of the cap-plate (FIG. 18A), exposing the upper half of the dual-track bearing raceways for the lateral prismatic joint. The cutaway view of the cap-plate (FIG. 18B) shows the cavity structure of the cap-plate and the cap-plate rim as well as the lateral prismatic joint bearings and bearing raceways.
Figure 18B:
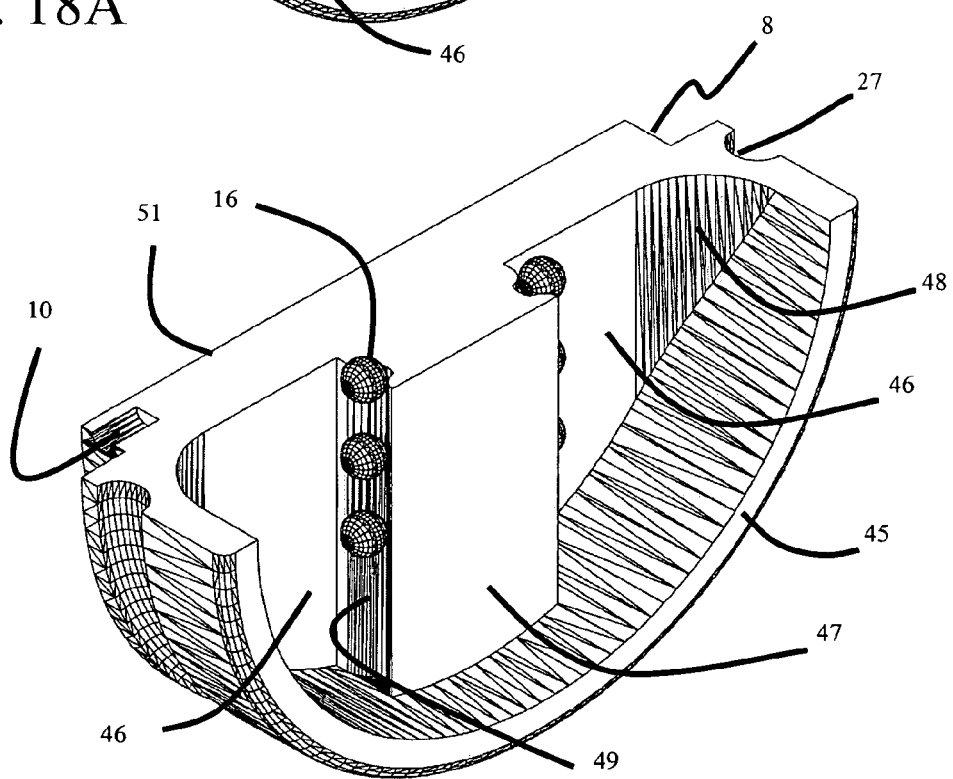

FIG. 18A illustrates the cap-plate 11 and the position of the lateral linear bearing support structure 47 and cap-plate's projecting rim 45. As seen in FIG. 18B, the lateral linear bearing raceways 49 are positioned on each side of the support structure 47. The cap-plate 11 and bearing support structure 47 may be integrated as a single part or manufactured as separate units that are fixedly attached. In one embodiment, additional surface curvature 48 (FIGS. 18A and 18B) at the anterior and posterior sections of the cap-plate can increase strength of the cap-plate. In this embodiment, the convex curvature 58, 59 of the plane-bearing guide 15 (FIG. 16) should be complimentary with the concave curvature 48 of the cap-plate. In a preferred embodiment, the lateral prismatic joint 52 (FIG. 19) maintains a small gap 53 (FIG. 19) between the cap-plate surfaces 46, 47 and plane-bearing guide surfaces 55 (FIG. 16) that reduces interference between those elements during FSU movements with lateral components.

In a further embodiment, this clearance of cap-plate and plane-bearing guide surfaces applies to the entire cap-plate cavity 50 interior surfaces and plane-bearing surfaces 55, 58, and 59. The cap-plate rim 45 and the width of the plane-bearing guide 15, in addition to extensions in width that may be contributed by oversized left or right lateral bearing stops, are able to limit the amount of lateral travel 65 of the plane-bearing guide within the cap-plate 11, and, therefore, in one embodiment the amount of left and right lateral bending. In a preferred embodiment, the center of curvature for the curved lateral surface 63 (FIG. 16) of the plane-bearing guide provides clearance for the guide as it moves laterally underneath the cap-plate. In a further embodiment, the center of curvature for the left and the right lateral surfaces 63 are not the same.

In an even further embodiment, these surfaces are not centered with the plane-bearing guide, but are offset so the lateral surfaces of the plane-bearing guide will not interfere with the cap-plate rim 45 during lateral movement. In one embodiment, the plane-bearing guide 15 mated with the cap-plate 11 forms the lateral prismatic joint 52 (FIG. 19). In a further embodiment, titanium steel ball-bearings, or, in an alternative embodiment, for added stiffness, rigid rod-bearings of desired cross sections, lateral surface geometries and material compositions (FIGS. 23A, 23B and FIGS. 24A, 24B), are positioned in the lateral bearing raceways 49, 57 to slidably connect the two pieces to form the lateral prismatic joint 52. Thus, in this embodiment, the plane-bearing guide 15 and the cap-plate 11 relate and move relative to each other through the bearing contacts. In a further embodiment, the plane-bearing guide 15 moves laterally 65 along the raceways with respect to the cap-plate 11. In a still further preferred embodiment, at or near the limits of the lateral prismatic 52 joint motion, the plane-bearing guide 15 contacts the rim 45 of the cap-plate 11. Thus, in this embodiment, the cap-plate 11 acts as a hard joint stop, placing a maximum travel limit on the prismatic joint 52 in lateral bending.

To increase the rigidity of the lateral prismatic joint 52 so that it supports greater loads, another alternative embodiment can utilize bearings and bearing raceways distributed on the flat portion 55 of the top surface of the plane-bearing guide 15 (FIG. 16). In a further alternative embodiment, bearing raceways can be utilized on surface 55 (FIG. 16) parallel to raceways 57.

EXAMPLE 6

Spring-Damping System

Preferably the subject invention utilizes a central shock-absorbing material within the core of the piston to reduce the effects of sudden motion on the prosthetic device and to support static loads placed on the prosthetic device. This central shock-absorbing material can comprise a variety of materials, for example, springs, elastomeric materials, or gel inserts.

One embodiment utilizes a central, helical spring 26 (FIG. 13). The spring may comprise a variety of materials, for example, plastics, metals, or a variety of alloys. In a preferred embodiment, the spring comprises machined titanium stainless steel alloy. In an alternative embodiment, the spring further comprises, for example, an elastomer or hydrophilic gel core or other shock-absorbing material structures 103, with sufficient spring constant to sustain the required intervertebral spacing of the FSU in the neutral position under gravitational load and sufficient compression-extension properties to allow the spring to fit into the piston cavity 83 under maximum compression. This spring based system for dealing with static and dynamic loads is referred to as the spring-damping system.

In the neutral position the machined helical spring 26 should be loaded so as to oppose the normal compressive force produced by anatomical structures under gravity.

In one embodiment, the shock absorbing elastomer or hydrophilic gel core does not fill the spring cavity 104, thus allowing for expansion under compression. The spring core materials utilized in the subject invention experience primarily axial forces, and are designed to take advantage of that fact.

In one embodiment, the machined helical spring screws onto the thread 116 of the mounting post 117 on the roof of the piston cavity 83 (FIG. 22) and the thread 32 of the mounting post 31 on the floor of the chambered-ball cavity 35 (FIG. 10). In a further embodiment, the threading sense of the two spring mounting posts 31 and 117 can be the same and are compatible with the threads 101 of the spring 26 (FIG. 13).

Forces acting on the prosthesis of the subject invention resolve into a force along the polar-axis 113 of the prosthesis and a force orthogonal to the axis. The polar-axis component of the force compresses or stretches the spring and the other force component moves the linkages. However, if the resultant force on the polar-axis 113 is not sufficient to compress or stretch the spring as required, there is no motion and the joint structure bears the force load without linkage motion.

In one embodiment, the piston, excluding the sagittal bearing support structure, may act as the machined helical spring itself. In this embodiment, there would be no hydraulic portals other than the separations of the spring rungs and those on top of the sagittal bearing support structure 67, would comprise a large threaded mounting post for the piston-spring to screw onto. In this embodiment, the piston-spring does not slide, but can be anchored into the chambered-ball at the piston seat and under nominal load in the neutral position of the FSU. The increased size of the piston-spring can enhance spring constant design options, but the piston-spring compresses and extends appropriately to match the previous polar-axis prismatic joint motion requirements. In these embodiments, the lateral stiffness of the spring should be greater than the axial stiffness of the spring.

In yet another embodiment, a second, smaller machined helical spring can be mounted on the threaded posts inside the much larger machined piston-spring and chambered-ball cavities. The second machined helical spring parallels the machined piston-spring and may not have to be particularly stiff except as the device nears maximum extension so as to provide additional extension loading capability.

The modular prosthetic disc mechanism is filled with biocompatible lubricating fluid in its minimal volume configuration, typically at maximum flexion. The fluid volume surrounding the piston and the bulging of the boot is sufficient to fill the piston cavity 83 and chambered-ball cavity 35 when the FSU is in the neutral position.

During flexion, the hydraulic system increases fluid pressure in the gap between the chambered-ball and socket base surfaces to reduce friction during motion of the ball-and-socket joint. This effect is similar to the operation of a synovial joint. A similar synovial action takes place at the piston and chambered-ball gap during piston motion along the polar-axis.

To increase the synovial effect between the chambered-ball 13 and socket-base 14, another embodiment eliminates the hydraulic portals 20 around the mouth of the chambered-ball cavity 35 and adds a bearing pressure seal at the mouth of the socket-base cavity 118. This seal prevents, or greatly reduces, the escape of fluid being pumped, during compression, into the bearing gap between the chambered-ball 13 and socket-base 14 through the hydraulic portals 20 at the base of the chambered-ball 13. During extension, the synovial effect is minimal, but then so is the loading on the joint surfaces.

To increase the synovial effect in the polar-axis prismatic joint 115 during compression, another embodiment eliminates the hydraulic portals 20 around the mouth of the chambered-ball cavity 35 and adds pressure seals to the chambered-ball and piston ring-bearings. All cavities in the device fill completely at minimum volume. As the piston extends the fluid in the gap, now under negative pressure, flows into the piston cavity. As the piston compresses, the fluid in the cavity flows into the polar-axis prismatic bearing gap under pressure since bearings seal both ends of the gap. This alternative embodiment preserves the hydraulic damping and shock absorbing characteristics for the polar-axis prismatic joint 115 and its characteristics can be engineered by the number, size and distribution of the hydraulic portals 20 on the top surface of the piston. During compression the hydraulic pressure in the gap between the piston 12 and the chambered-ball 13 also adds stiffness of the joint to lateral forces. This embodiment is compatible with the previous one that increases the synovial effect on the ball-and-socket joint 37. The piston 12 cannot be the helical spring for embodiments that enhance synovial operation.

EXAMPLE 7

Bearings

The subject invention can incorporate one or more bearing types and sizes. In one embodiment, the largest ball-bearings comprise the polar bearing 30 and the bearings utilized in the girdle and socket-base ring-bearing raceways 29, 36; the next largest ball-bearings are utilized in the plane-bearing guide raceways 57, 62; and the smallest ball-bearings comprise the chambered-ball and piston ring-bearings. In a preferred embodiment, the ball-bearings consist of titanium-carbide-covered hardened stainless steel. The size of the ball-bearings depends upon the raceways cross-sections and the number of ball-bearings in each raceway depends upon the scale of the prosthesis.

Other embodiments may vary the number, size, placement and material construction of the bearings and the bearing types. For example, a further embodiment replaces the ball-and-socket ring-bearings 18, 29, 19, 36 with ultra-high-molecular-weight polyethylene or similar thermoplastic bearing material on the exterior surfaces of the chambered-ball 13 and socket's spherical cavity 118. This embodiment may include one of the two polymer surfaces smooth and the other micro-rough, i.e., covered with enough randomly placed micro-bumps that can decrease friction between the surfaces, but not so many as to cause abrasion. The sizes of the micro-bumps may be dictated by desired wear, friction and stiction characteristics.

Another embodiment of the subject invention comprises coating the outer spherical surface of the chambered-ball 13 with, for example, relatively large, fixed, polar spherical sections of polymer material and coating the socket-cavity with a smooth layer of, for example, bearing thermoplastic. The polar spherical sections on the chambered-ball are then able to act as sliding point contact bearings and are arranged to uniformly distribute forces on the socket-base cavity 118. The latter embodiment eliminates the girdle and socket-base ring-bearings 18, 19 and polar bearing 30. Since the spherical sections of thermoplastic can be rigidly attached to the chambered-ball, and/or constitute surface features of a totally thermoplastic chambered-ball, they will not block the orifice of any distribution of hydraulic portals 20 elsewhere on the chambered-ball's surface.

Another alternative embodiment realizes the lateral and sagittal linear bearings with a tongue-and-groove arrangement comprising, for example, a mix of ultra-high-molecular-weight polyethylene or similar thermoplastic bearing material and biocompatible metal alloys. The tongue cross-sectional shape allows a variety of embodiments, for example, but not limited to: half a right-circular cylinder or half the more exotic cross-sections 76 in FIGS. 23B and 81 in FIG. 24B. In the latter case, the spherical surfaces 79 can offer point contacts between the sliding surfaces of the joint and reduce friction over the line contact of 75 or the surface contact of a tongue with a semicircle cross-section. While creating more friction than roller bearings, the tongue-and-grove arrangement can make the joint stiffer, especially when the tongue embodiment comprises a metal alloy, by eliminating bearing separators and bearing stops. The additional friction and stiction can provide an advantage by increasing FSU stability.

In yet another embodiment of the sagittal and lateral bearings, a bearing-thermoplastic can be utilized to coat portions of the raceway, in addition, titanium-carbide-coated hardened stainless steal cylindrical rod-bearings with various cross-sections 76, 81, may be utilized, with or without lubricant grooves 74, 80, that run the length of the raceway to the bearing stops. FIG. 23A shows a rod bearing 76 with four lubricating grooves 74 and four lines of contact 75, one per quadrant. This arrangement can provide stiffness and support.

Still other embodiments of prismatic joints may employ, for example, rigid rods with different surface geometries and characteristics. In a further embodiment, the rod-bearing geometry in FIG. 24A can contact the raceway surfaces in multiple points 79 on the spherical sections, reducing friction over the length of the cylindrical rod bearing. Rod-bearing 78 may not require lubricant grooves, even though shown, since the gaps between the slightly overlapping spheres could allow lubricant to feed into the raceways.

Further alternative embodiments for the piston and chambered-ball ring-bearings 25, 24 can entertain many of the options mentioned for the other bearings such as for example, comprising a single piece of material, for example, but not limited to, thermoplastic or titanium-covered stainless steel, with a variety of one or more cross-sections for different contact surfaces, lines or points. As mentioned previously, the embodiment illustrated in FIG. 28 utilizes surface bearings that may vary in material composition.

EXAMPLE 8

Corrugated Boot

In one embodiment, the corrugated boot 5, 107 (FIGS. 3A and 3B) consists of a strong, flexible-fiber, for example, but not limited to nylon, polyethylene, polyurethane, or spandex-like fiber (with 100% or greater elongation at break) woven screen mesh embedded into a biocompatible elastomer, for example, but not limited to silicones, isotactic polypropylenes with durometer of about 30 to about 40 and a tensile strength of about 5 MPA to about 10 MPA that makes a strong, flexible covering impervious to fluids. The boot thickness, depending upon spinal or other application, can vary from about 0.1 mm to about 1.0 mm or larger. In a preferred embodiment, the boot can be corrugated, much like a billows, with thicker, relatively stiff, fiber-belted annular sections 110 between thinner, non-belted, more flexible annular sections 109. In general, the boot corrugated thickness scales to the application requirements.

The weave and structure of the fiber within the elastomeric matrix may vary in the construction of the boot. In one embodiment, tough fiber belts can be embedded into sections 110 of the corrugated boot that can enable sections 110 to hold their shape better under compression and extension. Flexible fiber with a coarse weave, preferably diagonal to the central-axis of the boot, can be embedded in the entire boot elastomer matrix. The diagonal weave can provide more torsion resistance and the flexibility of the fibers can allow the boot to stretch up to about 50% without appreciable degradation in performance. Kevlar, and most commercial polyurethane fibers, may possess an elongation at break percentage that is too low for this application. The fiber size, from about 0.1 mm to about 0.5 mm, cross-section, for example, but not limited to, rectangular, circular, oval, or other polygonal shape, material, for example, but not limited to, nylon, polyurethane, spandex-like fiber, etc., and tightness, for example from about 0.1 to about 1 threads per millimeter) of the fiber weave constitute boot design parameters as well as the choice of elastomer substrate, for example, but not limited to, silicon rubbers. To increase boot strength in some applications, such as the larger FSUs, other embodiments may utilize stacked woven layers of boot fabric in conjunction with, or embedded in, a flexible elastomer substrate.

The posterior section of the boot typically stretches very little from a minimum at flexion to a maximum at extension of the FSU. The anterior section of the boot, in some cases, stretches up to about 7 times as much as the posterior portion. Therefore, the fiber density may comprise nonuniform materials throughout the elastomeric matrix.

In yet a further embodiment, the boot may comprise two or more sections, which can be joined to form the boot. In this alternative embodiment, a fluid-impervious, flexible (to about 100% elongation to break) membrane, can be utilized to cover the entire prosthesis. This membrane may not have fiber reinforcement, or very little, and does not utilize the corrugated structure discussed above.

In a further embodiment, two or more sections of thicker, tougher corrugated boot material may be used over the anterior surface of the membrane and one or more over the posterior surface of the membrane, for example extending from the cap-plate 11 to the socket-base 14. The corrugated strips may function somewhat like separate anterior and posterior ligaments, providing stability and strength to the joint. Both the strips and the membrane may be clamped together into the cap-plate grooves 27 and socket-base grooves 28 by means of clamping rings.

In a preferred embodiment, the boot wraps around the modular prosthetic disc mechanism 7, 108 (FIGS. 3A and 3B) and clamps securely to the cap-plate and socket-base to prevent fluid seepage into or out of the modular prosthetic disc mechanism that it encases. In a further preferred embodiment, the boot is open at each end with an internal diameter that can be slightly less than the outer diameter of the cap-plate and socket-base at the openings. The boot stretches some and slips snuggly over the cap-plate and socket base.

EXAMPLE 9

Vertebral-Plane Linkage and Operation

Figure 20:
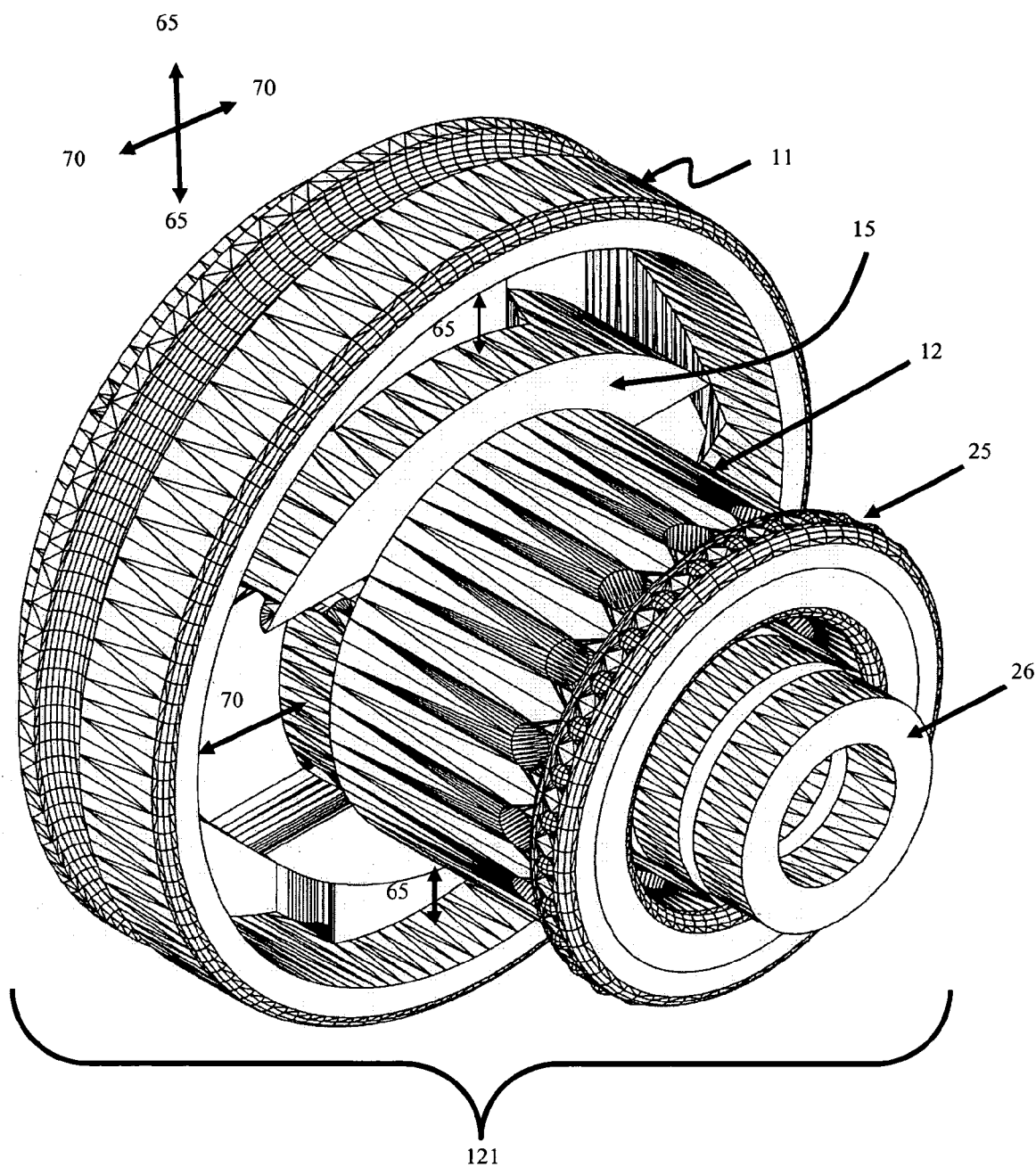
FIG. 20 presents a full, underneath view of the 2-DOF linkage, which can be referred to as the superior vertebral-plane linkage, realized by the cap-plate, plane-bearing guide, and the piston. A stylized spring is shown mounted onto the piston. The open end of the spring connects to the mounting post at the floor of the chambered-ball cavity.

In one embodiment, the cap-plate 11, plane-bearing guide 15, and the piston 12 are joined to provide a 2-DOF linkage called the vertebral-plane linkage 121 (FIG. 19, FIG. 20). In an alternative embodiment, interlocking bearings are utilized as the points of connection between these elements of the spinal disc prosthesis. In one embodiment, two orthogonal lines of movement 65 and 70 (FIG. 19) are able to adjust the position of the vertebral plane. Further, in one embodiment, the vertebral plane is oriented to be perpendicular to the polar axis 113. The vertebral-plane linkage 121 can position any vertebral-plane frame that is fixed to the superior vertebra of the FSU in which the prosthesis is installed to any position in the vertebral-plane contained in the FSU workspace. The 2-DOF vertebral-plane linkage 121 coupled with the 4-DOF spherical-polar-axis linkage 120 can provide a general purpose, 6-DOF linkage 96 (FIG. 21) between the superior and inferior vertebral plates, hence, superior and inferior vertebrae into which the plates are fused.

The vectors, 65, 70, and 89, in FIG. 21 indicate the three orthogonal translational degrees of freedom that can be obtained with the 6-DOF linkage 96 of the subject invention. The three translational motions 65, 70, and 89 correspond to the movements that can be generated by the lateral, sagittal, and polar-axis prismatic joints 52, 17, and 115, respectively. The ball-and socket joint 37, of the subject invention, can generate the three independent angular orientations 93, 94, and 95.

Figure 25A:
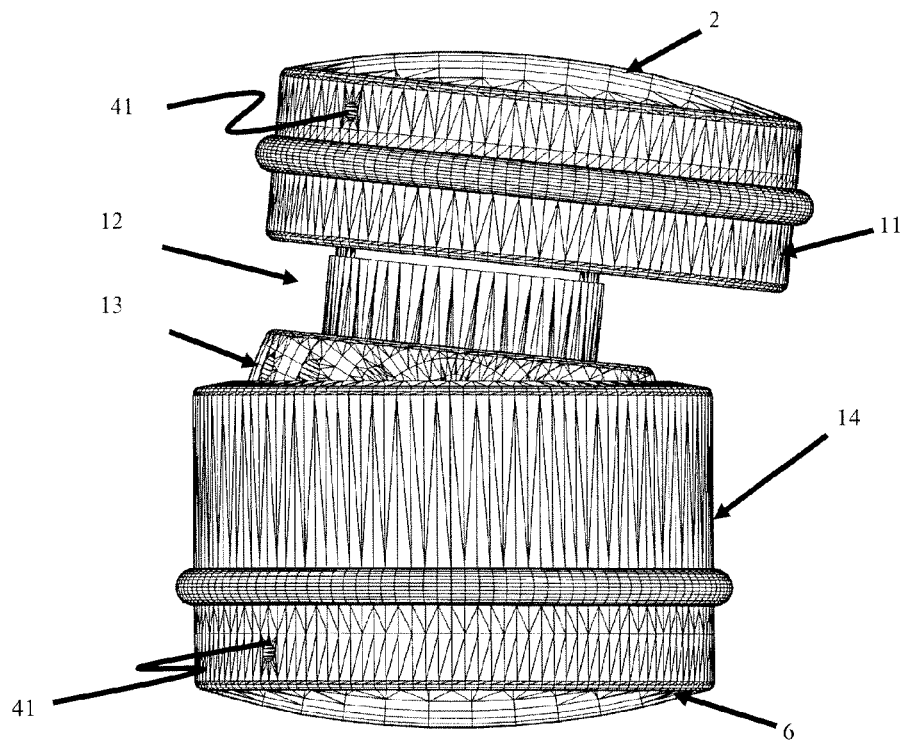
FIGS. 25A and 25B show the spatial mechanism in extension as seen from the left-lateral side of the device.
Figure 25B:
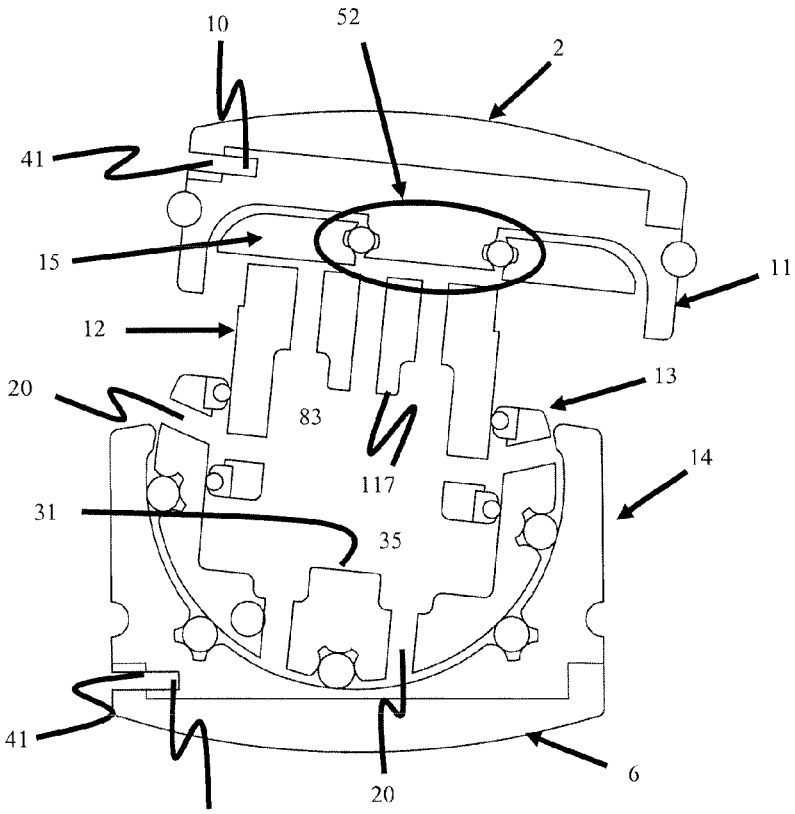

In a preferred embodiment, when the FSU moves to extension, the prosthesis moves into the configuration illustrated in FIG. 25A. FIG. 25A illustrates the prosthesis as seen from a left-lateral 3-D viewpoint while FIG. 25B is a mid-line sagittal plane cross-section of the device in the same configuration. In this preferred embodiment, there should be an equal tilt of the superior vertebral plate 2, the cap-plate 11, the plane-bearing-guide 15, piston 12 and chambered-ball 13 towards the posterior, but the cap-plate 11 and plane-bearing guide 15 will be more posterior than the piston 12. This indicates that the former translates posteriorly with respect to the piston 12 along the sagittal prismatic joint 17. The extension of the piston 12 along the polar axis 113 and out of the chambered-ball 13 is near maximum in this configuration. Although, as seen in the projection, there is yet more room for the piston 12 to extend since the piston ring-bearing 25 has not yet come up against the chambered-ball ring-bearing 24. As the piston 12 moves into extension, fluid in the upper cavities of the prosthesis drains into the chambered-ball and piston cavities 35, 83.

Figure 26A:
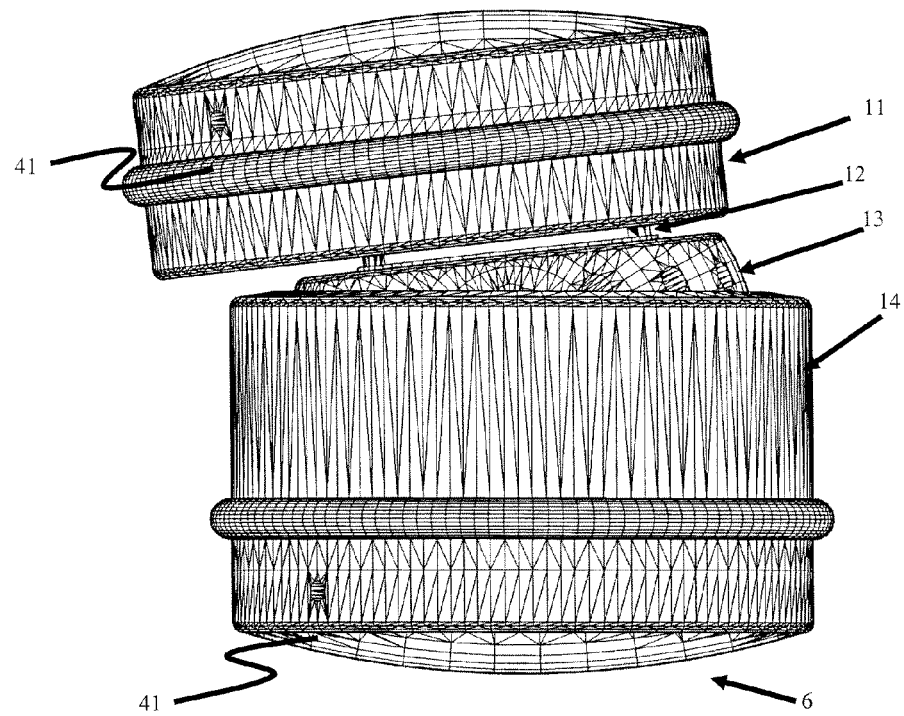
FIGS. 26A and 26B illustrate the spatial mechanism in flexion as seen from the left-lateral side of the device.
Figure 26B:
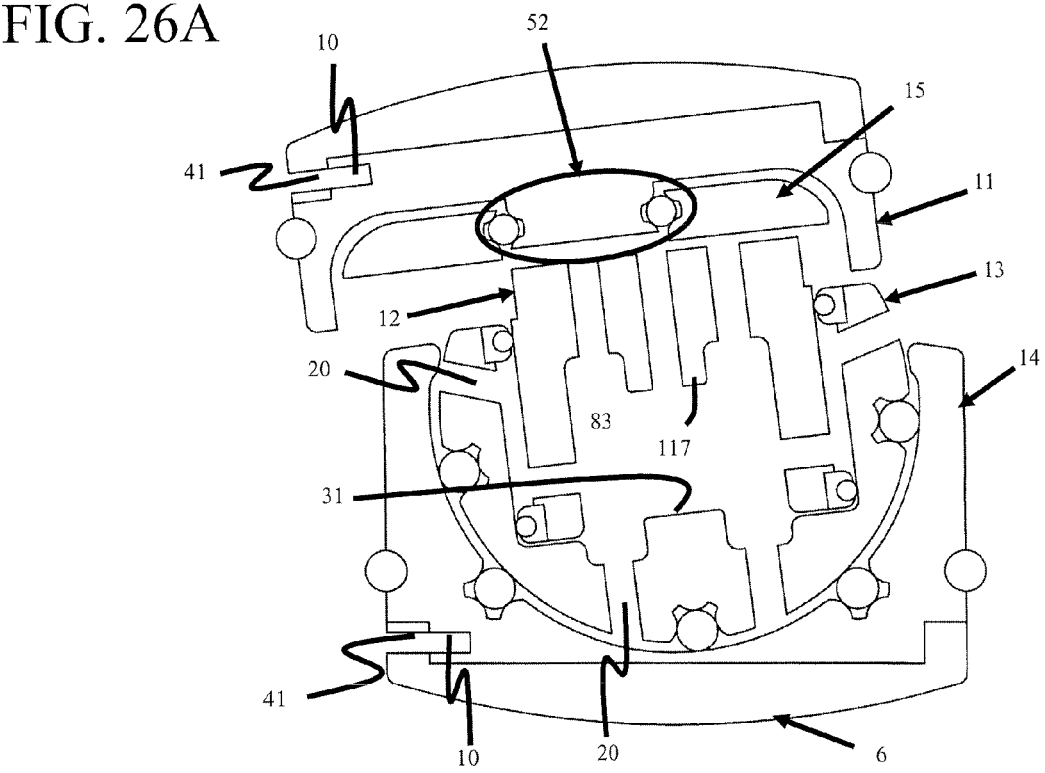

In a further embodiment, during flexion of the FSU, the prosthesis is able to move into the configuration drawn in FIG. 26A. FIG. 26A illustrates the prosthesis as seen from a left-lateral 3-D viewpoint while FIG. 26B is a mid-line sagittal plane cross-section of the device in the same configuration. In this embodiment, there is an equal tilt of the superior vertebral plate 2, the cap-plate 11, the plane-bearing-guide 15, piston 12 and chambered-ball 13 towards the anterior, but the cap-plate 11 and plane-bearing guide 15 are more anterior than the piston 12. This indicates that the former translates anteriorly with respect to the piston 12 along the sagittal prismatic joint 17. The piston 12 maximally slides into the chambered-ball 13 along the polar axis 113 in this configuration. In this embodiment, the piston-ring bearing 25 sits on the piston seat 33 within the chambered-ball cavity 35. The prosthetic should not be able to flex further when the piston sits on the piston seat 33 (FIG. 10) of the chambered-ball cavity 35. In this preferred embodiment, the shock absorbing material, for example a spring 26, elastomer, or various hydrophilic gel materials, inserted into the spring core reach maximal compression.

The extension and flexion configurations in FIGS. 25A and 25B and FIGS. 26A and 26B make apparent the relative angle of chambered-ball rotation from flexion to extension, with neutral as the zero reference. In a preferred embodiment, the swing angle of the polar axis 113 of the chambered-ball between maximum flexion and maximum extension is from about 5° to about 10°. In an even more preferred embodiment, the swing angle of the polar axis 113 of the chambered-ball between maximum flexion and maximum extension is from about 10° to about 20°. Additionally, in a preferred embodiment, the lateral bending swing angle of the polar-axis 113 between maximum left-lateral bending and maximum right-lateral bending is from about 3° to about 8°. In an even more preferred embodiment, the lateral bending swing angle of the polar-axis 113 between maximum left-lateral bending and maximum right-lateral bending is from about 8° to about 14°. In an alternative embodiment, the lateral bending angle limits can be increased by about 1° by narrowing the width of the plane-bearing guide. Axial rotation of the piston and chambered-ball can also be partially constrained by the boot and by the natural limits of the FSU muscles and ligaments.

Figure 27A:
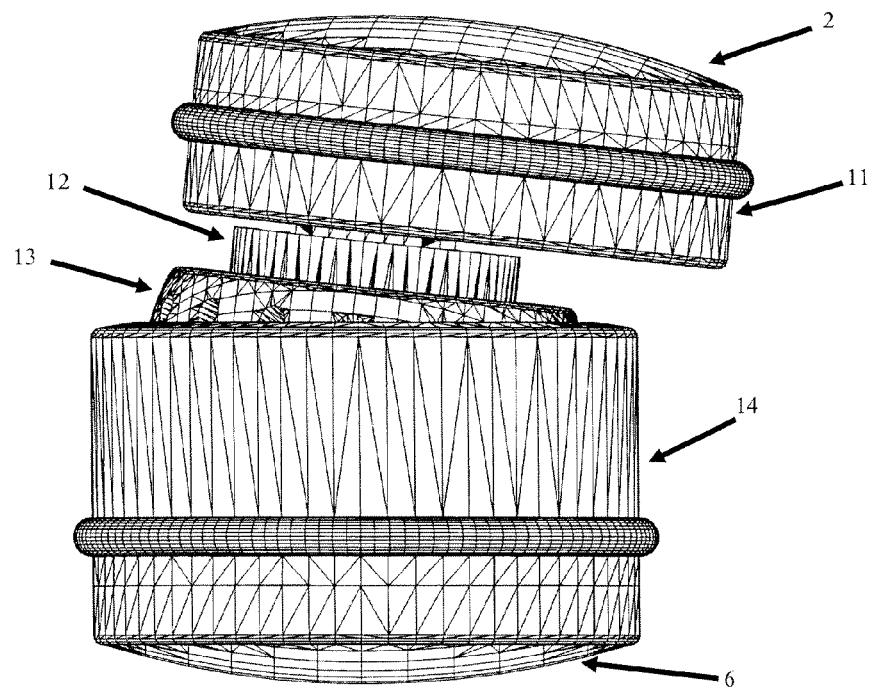
FIGS. 27A and 27B are views of the spatial mechanism from the posterior side executing pure right-lateral bending.
Figure 27B:
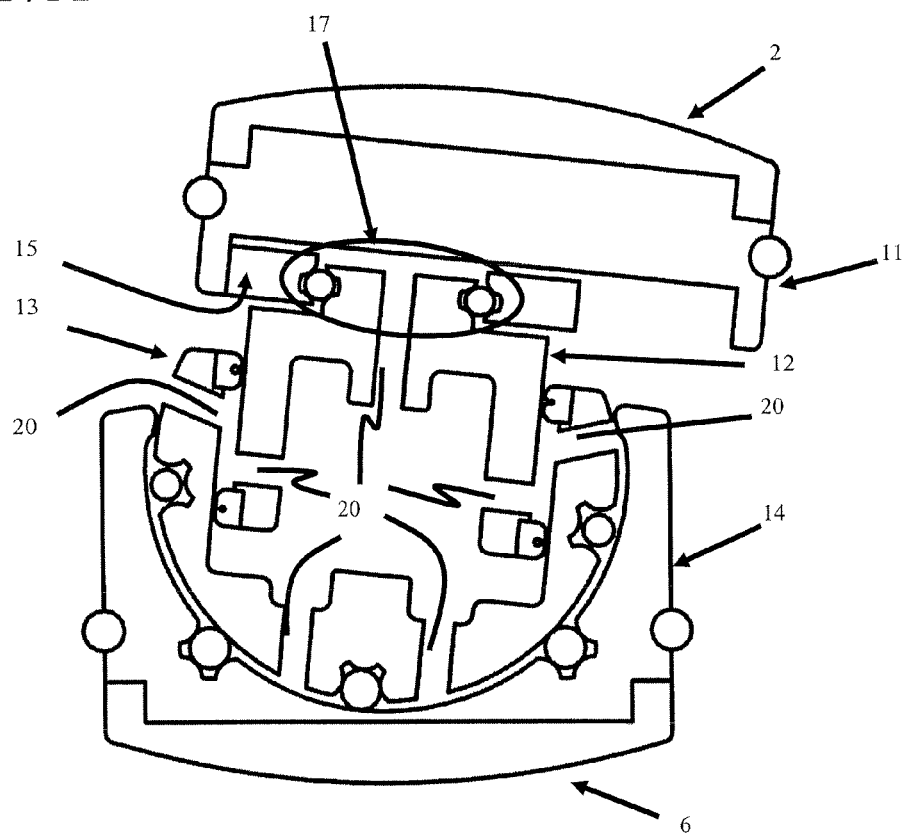

Pure right-lateral bending of the prosthesis, shown from a 3-D posterior viewpoint in FIG. 27A, differs in several respects from extension in FIG. 25A. The ball-and-socket joint 37 rotates more distal elements of the device about the frontal axis instead of the sagittal axis, but in all other respects the function performed by the orienting joint is essentially the same. From the midline frontal plane projection of the prosthesis in pure right-lateral bending, however, the plane-bearing guide 15 moves with respect to the cap-plate 11 and contacts the cap-plate rim 45, which can function as an effective, mechanical stop for the lateral prismatic joint. Finally, the piston may not extend as far at maximum lateral motion as it does at maximum extension due to the motion allowed by the facet joints of a typical spine.

In a preferred embodiment, the ball-and-socket joint 37 orients the more distal elements, the piston 12 extends or retracts, and the plane-bearing guide 15 will slide into place with respect to the cap-plate and the piston simultaneously. In a further preferred embodiment, within the workspace of the linkage, forces will either cause movement along prismatic joint axes, rotate the chambered-ball 13 in its socket-base 14, or compress or stretch the spring 26. The modular 6-DOF prosthetic device structure itself bears torsion loads about the frontal and sagittal axis, but the corrugated boot in the subject invention may offer the only resistance to axial torsion loads.

In a further embodiment the assembled, kinematically-linked, 6-DOF linkage of the device is approximately 50 millimeters or less from end to end. In an even more preferred embodiment, the assembled, kinematically-linked, 6-DOF linkage of the device is approximately 20 millimeters or less from end to end.

The 6-DOF linkage 96 (FIG. 21) can achieve most combinations of sagittal, lateral, and axial rotations within the above angle limits while performing the necessary translations along the polar-axis, sagittal, and lateral prismatic joints 115, 17, 52 induced by the displacement of the superior vertebra with respect to the inferior vertebra of an FSU. This range of motion is suitable for any disc replacement along the spine.

EXAMPLE 10

Alternative Embodiments for Use with Non-General FSU

Mechanical programming of the prosthesis may utilize oversized joint stops on the lateral and sagittal prismatic joints to create a prosthetic workspace that 1) can more nearly match a patient's nominal FSU workspace and flexibility or 2) can accommodate clinical conditions that indicate movement restrictions or workspace reductions of the modular 6-DOF spinal disc prosthesis.

Essentially the spatial mechanism may be tailored to meet individual client specifications through mechanical programming with oversized joint stops. Lateral bearing stops 60, 61, if oversized, limit the travel of the lateral prismatic joint 52 to less than the maximum by extending beyond the edge of the plane-bearing guide's lateral surface 63 with the same surface curvature as the guide. As the unit performs lateral bending, the oversized stops will contact the cap-plate rim 45 for smaller lateral angular displacements. These stops need not be identical in size. Equal extension of the oversized bearing stops yield the same movement reduction in the left-lateral or right-lateral direction of the lateral prismatic joint 52, which translates into reduced lateral angles. Unequal sized bearing stops yield different limits in opposing traversals along the lateral prismatic joint 52, which translates into different limits for left and right lateral bending. Similarly, oversized sagittal bearing stops 71, 72 make the effective diameter of the piston 12 just that much larger, causing the piston 12 to jam against the cap-plate rim 45 as a hard stop for smaller angles of flexion and extension. These stops need not be identical in size. Equal extension of the oversized bearing stops yield the same movement reduction anteriorly or posteriorly of the sagittal prismatic joint, which translates into reduced angles of flexion or extension of the unit. Unequal sized bearing stops yield different limits in opposing traversals along the sagittal prismatic joint 17, which translates into different limits for flexion and extension Some workspace and movement restrictions, while mechanically programmable with oversized joint stops, lead to modifications of the invention that reduce the degrees-of-freedom, hence, complexity and number of kinematic pairs. For example, if clinical conditions indicate that axial rotations must be eliminated, an alternative embodiment replaces the ball-and-socket joint 37 (FIG. 10) by a universal joint (Hooke joint) to eliminate axial rotation in the modular prosthetic disc mechanism 7, 108 (FIGS. 3A and 3B) and make it stiff to torsion. For even more severe restrictions that require the elimination of lateral bending, another embodiment replaces the ball-and-socket joint 37 by a simple rotating joint about the sagittal axis. A non-circular piston 12 cross-section eliminates axial rotation in this latter embodiment.

EXAMPLE 11

Spinal Disc Prosthesis Utilizing Lower Pair Elements

All joint elements of the modular prosthetic disc mechanism 7, 108 can be replaced by lower pairs, a choice that eliminates all ball-bearings and rod-bearings and, technically, makes the modular prosthetic disc mechanism into a prosthetic disc linkage (FIG. 28). The ball-and-socket joint 37 becomes a spherical pair (213, 214) and the polar-axis, sagittal, and lateral prismatic joints 115, 17, 52 (FIG. 12, FIG. 19) become true prismatic pairs (212, 213), (215, 217) and (215, 252) respectively, with only surface contact for all joints, no multi-point or line bearings.

In this alternative linkage embodiment, the bearings become the surface contact of the various pairs as follows. The spherical surface of the socket-base 214 and the chambered-ball 213 contact each other directly, with a small clearance to form the ball-and-socket joint. The cylindrical pair (212, 213) forms the polar-axis prismatic joint. The plane-bearing guide 215 raceways are grooves for sliding tongues 252 mounted on the cap-plate 211 and tongues 217 mounted on the piston 212. The sliding surfaces for both lateral and sagittal prismatic pairs on the cap-plate 211 and the upper flat surface 55 on the plane-bearing guide 215 become part of the load bearing surfaces of the lateral prismatic joint, yielding greater strength and load capacity. The surface 73 (FIG. 22) on top of the piston 212 FIG. 28) and the lower flat surface on the plane-bearing guide 215 next to the piston become part of the load bearing surfaces of the sagittal prismatic joint, yielding greater strength and load capacity. Finally, this alternative embodiment eliminates the piston and chambered-ball ring-bearings and increases the thickness of the chambered-ball so that the piston's lateral surface 66 slides against the cylindrical surface of the chambered-ball cavity 35. To reduce friction in the sagittal and lateral prismatic joints, the plane-bearing guide may be, for example, machined or cast out of high molecular density polyethylene or other rugged thermoplastic to reduce friction between it and titanium-carbide-coated stainless steel embodiments of the cap-plate 211 and piston 212. The chambered-ball too is made from tough, durable thermoplastic to reduce friction in the ball-and-socket joint while the socket-base 214 is titanium-carbide-coated stainless steel.

Even though this embodiment increases friction in the joints, it is simpler to build, has fewer parts, and is more robust and able to handle greater loads. These considerations might favor the lower-pair embodiment over the ball-bearing version. In another embodiment of FIG. 28, the superior and inferior plates are a titanium alloy and the remaining elements are high molecular density polyethylene or similar thermoplastic.

EXAMPLE 12

Assembly of the Prosthetic Disc Linkage

An exploded view of the modular 6-DOF spatial mechanism spinal disc prosthesis (FIG. 7A) identifies the principle elements of the prosthesis in a preferred embodiment. In this view of a preferred embodiment of the disc prosthesis (FIG. 7A), the socket ring-bearing 19 is hidden in the socket-base 14 and the upper part of the lateral prismatic joint is hidden within the cap-plate 11.

An example of the modular prosthetic disc mechanism 7, 108 (FIG. 3) assembly sequence of a preferred embodiment helps to visualize the linkage and interaction between the various components of the module.

The opening of the socket-base spherical cavity 118 (FIG. 8) is less than the circumference of the spherical chambered-ball 13 (FIG. 9), which itself exceeds a hemisphere in size. Additionally, a protruding lip 119 (FIG. 8) along the socket cavity opening narrows the opening further (FIG. 8) and blocks the girdle ring-bearing 18 (FIG. 5) from exiting the socket cavity 118. In a preferred embodiment, this lip has a smaller radius of curvature than the socket cavity, but larger than the chambered-ball 13 and shares the same center with the ball and socket cavity. To join the ball and socket and form a spherical joint 37 (FIG. 10) the socket-base can comprises two or more sections. In one embodiment, the socket-base comprises two halves. In a further embodiment, the chambered-ball and the ball-bearings for the girdle 18 and socket 19 ring bearings are placed into the raceways 29 (FIG. 9) and 36 (FIG. 10) respectively, the socket-base sections, preferably halves, are placed over the ball, and fixedly attached by, for example, welding, or otherwise fastened, joining the socket sections or halves, to enclose the chambered-ball and lock it and the ball-bearings into the socket cavity 118. Under normal operation, it is preferable that the chambered-ball 13 not pull out of the socket-base 14. In an alternative embodiment, the socket-base 14 and chambered-ball 13 form an essentially spherical pair (213, 214). In a further preferred embodiment, the socket-base and chambered ball utilize spherical surface bearings (FIG. 28).

To continue assembly of a preferred embodiment of the subject invention, the spring 26 (FIG. 13) is screwed onto the threaded 32 mounting post 31 (FIG. 10) at the floor of the chambered-ball cylindrical cavity 35 (FIG. 9). Further, the piston is inserted with piston ring-bearing 25 (FIG. 11) mounted onto the bearings seat 89 (FIG. 11), into the cylindrical chambered-ball cavity. The piston and ball are locked together by mounting the chambered-ball ring-bearing 24 into the seat 84 on the chambered-ball 13 (FIG. 9). Continuing with a preferred embodiment the piston's threaded 116 mounting post 117 (FIG. 12) is connected to the spring 26. The piston 12 and chambered-ball 13 form the polar-axis prismatic joint 115 that slides along the central axis of the piston (FIG. 12), which also defines the polar-axis 113 (FIG. 10) of the chambered-ball 13. The spring 26, provides a spring-damping system for the prosthesis and enables the prosthesis to accommodate compression and extension loads. In one embodiment, the spring also comprises an undersized elastomer 104 or hydrophilic gel core 103 (FIG. 13). As the piston moves in and out 89 of the chambered-ball cavity, the spring 26 compresses or extends. Increased compression on the spring causes the top of the piston to come into contact with the elastomer or gel core material 103 and provide additional load bearing and shock absorbing capacity.

Thus, in one embodiment, this subassembly 120 (FIG. 14) constitutes a 4-DOF Spherical-polar-prismatic linkage that is able to orient, or point, the piston 12 in any direction and extend or retract it radially along the chambered-ball's polar-axis 113. Actuation of the spherical-polar-axis linkage 120 facilitates the movement of, for example, lubricating fluid through hydraulic portals 20 located on the piston 12 and chambered-ball 13 to bearing surfaces, points and lines. In a further preferred embodiment, the number, size and distribution of the hydraulic portals 20 on these elements determine the amount of hydraulic damping, shock absorption, and lubrication distribution and flow.

In one embodiment, the anterior to posterior raceways 62, the sagittal raceway, (FIG. 19) of the plane-bearing guide 15 (FIG. 16) are slidably connected within with the sagittal prismatic joint raceways 21 located at the distal end of the piston 12 (FIG. 11). In an alternative embodiment, ball-bearings 16 are utilized with joint stops 22 to slidably connect the plane-bearing guide 15 (FIG. 19) and the piston to form the sagittal prismatic joint 17 (FIG. 5, FIG. 19), 82 (FIG. 17).

In a further embodiment, an additional prismatic joint in the kinematic chain is created by a cap-plate 11 that is slidably connected to the plane-bearing guide 15 (FIG. 20) while aligning the two lateral raceways 57 (FIG. 17) of the plane-bearing guide 15 with the two raceways 49 on the lateral prismatic joint support 47 (FIG. 18A). In an alternative embodiment, ball-bearings 16 can be utilized with joint stops 60 and 61 (FIG. 17) to slidably connect the plane-bearing guide 15 and the cap-plate 11 to form the lateral prismatic joint 52 (FIG. 19). The plane-bearing guide 15, which slides laterally within the cap-plate cavity 50, in an alternative embodiment, provides ample clearance for utilizing various point, line and surface bearings. To complete the assembly of the modular prosthetic disc mechanism of a preferred embodiment 7, 108, a boot 5, 107 is utilized over the subassembly, and aligned with a cap-plate groove 27 and a socket-base groove 28 (FIG. 7A) having corresponding depressions 109 (FIG. 2A, FIG. 2B) in the boot. In a further preferred embodiment, the boot position is maintained with the use of clamping rings 4 (FIG. 2A, FIG. 2B) which are positioned over the boot and securely clamp the boot into the grooves, sealing the mechanism from external fluids. In yet a further preferred embodiment, a corrugated boot is utilized comprising sections of alternating thickness around the circumference of the boot as illustrated in FIGS. 2A and 2B. Thus, as the corrugated boot compresses, the more elastic, thin sections 109 collapse and the thicker less-elastic sections 110 resist the hydraulic pressure inside the prosthesis. At maximal extension, a negative pressure develops as the amount of fluid will not fill the prosthesis cavities.

In one embodiment, lubricating fluid is inserted into the boot cavity filling up to about 95% of the cavity when in a neutral position. In yet a further preferred embodiment, the cavity space not filled with lubricating fluid is filled with air, or other gases, to equalize internal pressure with ambient pressure. The fluid and air inserted into the modular prosthetic disc mechanism may cause bulging of the corrugated boot 5, 107 when the piston 12 assumes maximum compression. Thus, at maximal flexion, the fluid pressure inside the prosthesis is positive. During compression, the air or other gases within the boot can provide additional shock absorption. In yet a further embodiment, a syringe can be used to insert various fluids, for example lubricating fluids, into the device. In a still further embodiment, an opening within the central, threaded screw hole 10 in the cap-plate rim 45 could be used to introduce various fluids within the boot of the subject invention. In yet a further preferred embodiment, a screw 3, in conjunction with, for example, a liquid gasket, can be used to seal this opening from the environment and prevent leakage.

In one embodiment, assembly of the prosthetic disc linkage 7, 108 requires aligning the module properly with respect to the vertebral plates 2, 6 as the module requires a definite orientation with respect to the vertebral plates. When inserting a new prosthetic disc of the subject invention, the vertebral plates can be properly aligned on the modular disc prior to installation. In one embodiment lock-and-align screws 3 (FIG. 5, FIG. 6A and FIG. 6B) can be used to join the superior vertebral plate 2 to the cap-plate 11 and to join the inferior vertebral plate 6 to the socket-base 14. In a further embodiment, lock-and-align screws 3 are inserted through holes 41 in the anterior lip 40 of the vertebral plates (FIG. 6) and screw into threaded holes 10 (FIGS. 3A and 3B) of the cap-plate 11 and socket-base 14 (FIG. 4) of the mechanism. In a still further embodiment, three lock-and-align screws are utilized with the cap-plate 11 and three lock-and-align screws are utilized with the socket-base 14. When utilized, the screws can prevent the modular prosthetic disc mechanism 7, 108 from disengaging or misaligning with the vertebral plates.

In yet a further embodiment, a center-anterior positioned screw hole may provide the surgeon a fiducial mark for prosthesis insertion. The other matching lock-and-align holes may vary in number and location on the vertebral plates, cap-plate and socket-base, depending on spinal location and surgical convenience for easy insertion and removal.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A prosthetic device for approximating spinal disc movement comprising:
   a socket-base;
   a means for providing at least one and up to three, independent or dependent, degrees of rotational freedom positioned and secured within said socket-base;
   a piston for providing prismatic joint motion parallel to the axis of the piston, having a first end slidably attached to said means for providing at least one and up to three degrees of freedom;
   a sagittal prismatic joint element having a first side fixedly attached to a second end of said piston;
   a plane-bearing guide having a first side that is slidably affixed to a second side of the sagittal prismatic joint element, via a first bearing raceway, and having a second side comprising a second bearing raceway generally perpendicular to the first bearing raceway to form an element of a lateral prismatic joint; and
   a cap-plate which is slidably affixed to said lateral prismatic joint element;
   wherein said device has, at one end, means for attachment to a first vertebra and said device has, at a second end, means for attachment to a second vertebra and, when said device is implanted in the spine with said attachment means engaged with a first and second vertebra, said device forms a kinematic chain of connected, articulating components between said first and second vertebra, wherein said device has means for providing at least one and up to three independent rotational degrees of freedom and additional means for providing at least one and up to three independent linear degrees of freedom.

2. The device, according to claim 1, wherein said means for providing rotational degrees of freedom is selected from the group consisting of a ball and socket, a cylinder and socket, a piston and socket and a universal (Hooke) joint.

3. The device, according to claim 1, further comprising a cavity within said means for providing rotational degrees of freedom for containing the slidably attached piston therein.

4. The device, according to claim 3 wherein said piston further comprises an exterior lateral surface surrounding a means facilitating linear movement selected from the group consisting of springs, elastomers and compressible fluids.

5. The device, according to claim 4, wherein said means for facilitating linear movement along the axis of the piston is attached at one end to the cavity containing said piston and at the opposite end to the piston.

6. The device, according to claim 4, wherein said means for facilitating linear movement further comprises load-bearing capabilities that can support the piston and control maximal compression of the piston within the cavity containing said piston.

7. The device, according to claim 6, wherein the piston rotates via the means for providing at least 1 rotational degree of freedom, such that forces or loads applied to the piston are translated to said means for facilitating linear movement.

8. The device, according to claim 7, further comprising a damping system within the means for facilitating linear movement.

9. The device, according to claim 8, wherein said damping system comprises an elastic material and/or compressible fluids with sufficient viscosity and spring constant to provide sufficient load-bearing and shock absorbing compression before maximal piston compression.

10. The device, according to claim 1, further comprising vertebral plates for fixedly attaching the device between two vertebrae.

11. The device, according claim 10, further comprising threads located at one or both ends of the device, wherein said threads are compatible with threads on the vertebral plates such that one or more vertebral plates may be screwably attached to one or both ends of the device.

12. The device, according to claim 11, wherein opposable threads are located at each end of the device, and wherein said opposable threads are compatible with threads on the vertebral plates such that the device may be positioned between the vertebral plates and twisted or turned in one direction to secure and/or lock the device simultaneously between two vertebral plates.

13. The device, according to claim 1, wherein said means for providing rotational and linear degrees of freedom comprise a material selected from the group consisting of titanium steel, titanium-carbide-coated stainless steel, polyurethane, polyurethane thermoplastic, cobalt-chromium-molybdenum alloy, plastic, and glass.

14. The device, according to claim 10, wherein said vertebral plates comprise a material selected from the group consisting of titanium, cobalt-chromium-molybdenum alloy, and titanium-carbide-coated stainless steel with a bone fusion matrix.

15. The device, according to claim 1, further comprising a boot fixedly engaged with each of said means for attachment to the vertebrae, such that the means for providing said degrees of freedom are sealed within the boot thereby preventing fluids external to said device from contacting moveable elements of the device.

16. The device, according to claim 15, further comprising a biocompatible lubricant sealed within the boot.

17. The device, according to claim 16, further comprising hydraulic portals that allow said biocompatible lubricant to be circulated around and through the moveable elements of the device.

18. The device, according to claim 1, further comprising one or more ring-bearings positioned between and in contact with the socket and the means for providing at least one degree of rotational freedom such that the means for providing at least one degree of rotation freedom, when positioned within the socket is supported by and swivels on the one or more bearings of the ring-bearings.

19. The device, according to claim 1, further comprising one or more bearings positioned within one or both of the bearing raceways within the plane-bearing guide such that the sagittal and/or lateral prismatic joints when coupled are supported by and slide upon the one or more bearings.

20. The device, according to claim 1, further comprising one or more piston ring-bearings along the central axis of the piston, positioned between and in contact with the piston and said means for providing at least one degree of rotation such that said piston is supported by and slides upon the piston ring-bearings.

21. The device, according to claim 1, wherein at least one of said means for providing degrees of freedom utilizes surface, line, and point contact bearings.

22. The device, according to claim 15, wherein said boot comprises a strong, flexible, non-homogeneous, fiber reinforced elastomer matrix.

23. The device, according to claim 22, wherein said boot is capable of providing torsional load bearing.

24. The device, according to claim 15, wherein said boot is capable of providing non-linear compression and extension.

25. The device, according to claim 1, further comprising bearing stops affixed within one or more bearing raceways of the plane-bearing guide to control and/or limit sagittal and/or lateral motion.

26. The device, according to claim 1, further comprising linkage to control and/or limit vertebral plate separation.

27. The device according to claim 1, wherein the length of the device, between said first and said second end, is less than about 50 mm.

28. The device, according to claim 1, wherein the length of the device, between said first and said second end is less than about 25 mm.

29. A prosthetic device for approximating spinal disc movement comprising:
a socket-base;
a means for providing at least one and up to three, independent or dependent, degrees of rotational freedom positioned and secured within said socket-base;
a piston for providing prismatic joint motion parallel to the axis of the piston, having a first end slidably attached to said means for providing at least one and up to three degrees of freedom;
a sagittal prismatic joint element having a first side fixedly attached to a second end of said piston; and
a plane-bearing guide having a first side that is slidably affixed to a second side of the sagittal prismatic joint element, via a first bearing raceway, and having a second side comprising a second bearing raceway generally perpendicular to the first bearing raceway;
wherein said device has, at one end, means for attachment to a first vertebra and said device has, at a second end, means for attachment to a second vertebra and, when said device is implanted in the spine with said attachment means engaged with a first and second vertebra, said device forms a functional spinal unit of connected, articulating components between said first and second vertebra, wherein said device has means for providing at least one and up to three independent rotational degrees of freedom and additional means for providing at least one and up to three independent linear degrees of freedom.

30. A method for approximating spinal disc movement comprising:
a socket-base;
a means for providing at least one and up to three, independent or dependent, degrees of rotational freedom positioned and secured within said socket-base;
a piston for providing prismatic joint motion parallel to the axis of the piston, having a first end slidably attached to said means for providing at least one and up to three degrees of freedom;
a sagittal prismatic joint element having a first side fixedly attached to a second end of said piston; and
a plane-bearing guide having a first side that is slidably affixed to a second side of the sagittal prismatic joint element, via a first bearing raceway, and having a second side comprising a second bearing raceway generally perpendicular to the first bearing raceway;
wherein said method comprises securing within the spine of an animal, a prosthetic device wherein said device has, at one end, means for attachment to a first vertebra and said device has, at a second end, means for attachment to a second vertebra and, when said device is implanted in the spine with said attachment means engaged with a first and second vertebra, said device forms a kinematic chain of connected, articulating components between said first and second vertebra, wherein said device has means for providing at least one and up to three independent rotational degrees of freedom and additional means for providing at least one and up to three independent linear degrees of freedom.

31. The method according to claim 30, wherein said means for providing rotational degrees of freedom is selected from the group consisting of a ball and socket, a cylinder and socket, a piston and socket and a universal (Hooke) joint.

32. The method, according to claim 31, wherein said means for providing linear degrees of freedom comprises a cavity with a movable piston therein.

33. The method, according to claim 32, wherein said piston further comprises an exterior lateral surface surrounding a means for facilitating linear movement selected from the group consisting of springs, elastomers and compressible fluids.

34. The method, according to claim 33, wherein said means for facilitating linear movement along the axis of the piston is attached at one end to the cavity containing said piston and at the opposite end to the piston.

35. The method, according to claim 33, wherein said means for facilitating linear movement further comprises load-bearing capabilities that can support the piston and control maximal compression of the piston within the cavity containing said piston.

36. The method, according to claim 35, wherein the piston rotates via the means for providing at least 1 rotational degree of freedom, such that forces or loads applied along the axis of the piston are translated to said means for facilitating linear movement.

37. The method, according to claim 36, further comprising a damping system within the means for facilitating linear movement.

38. The method, according to claim 37, wherein said damping system comprises an elastic material and/or compressible fluids with sufficient viscosity and spring constant to provide sufficient load-bearing and shock absorbing compression before maximal piston compression.

39. The method, according to claim 30, comprising vertebral plates attached to each end of the device, wherein said vertebral plates can be used for fixedly attaching the device between two vertebrae.

40. The method, according to claim 39, further comprising threads located at one or both ends of the device, wherein said threads are compatible with threads on vertebral plates such that one or more vertebral plates may be screwably attached to one or both ends of the device.

41. The method, according to claim 40, further comprising opposable threads located at each end of the device, and wherein said opposable threads are compatible with threads on the vertebral plates such that the device may be positioned between the vertebral plates and twisted or turned in one direction to secure and/or lock the device simultaneously between two vertebral plates.

42. The method, according to claim 30, wherein said means for providing rotational and linear degrees of freedom comprise a material selected from the group consisting of titanium steel, titanium-carbide-coated stainless steel, polyurethane, polyurethane thermoplastic, cobalt-chromium-molybdenum alloy, plastic, and glass.

43. The method, according to claim 39, wherein said vertebral plates comprise a material selected from the group consisting of titanium, cobalt-chromium-molybdenum alloy, and titanium-carbide-coated stainless steel with a bone fusion matrix.

44. The method, according to claim 30, further comprising a boot fixedly engaged with each of said means for attachment to the vertebrae, such that the means for providing said degrees of freedom are sealed within the boot thereby preventing fluids external to said device from contacting moveable elements of the device.

45. The method, according to claim 44, further comprising a biocompatible lubricant sealed within the boot.

46. The method, according to claim 45, further comprising hydraulic portals that allow said biocompatible lubricant to be circulated around and through the moveable elements of the device.

47. The method, according to claim 30 farther comprising one or more bearings positioned between and in contact with elements of said kinematic chain such that said elements of said kinematic chain can be supported by and swivel on the one or more bearings.

48. The method, according to claim 47, wherein said bearings are selected from the group consisting of surface, line, and point contact bearings.

49. The method, according to claim 44, wherein said boot comprises a strong, flexible, non-homogeneous, fiber reinforced elastomer matrix.

50. The method, according to claim 49, wherein said boot is capable of providing torsional load bearing.

51. The method, according to claim 49, wherein said boot is capable of providing non-linear compression and extension.

52. The method, according to claim 30, further comprising bearing stops affixed within the means for providing at least one and up to three independent linear degrees of freedom to control and/or limit sagittal and/or lateral motion.

53. The method, according to claim 30, further comprising linkage to control and/or limit vertebral plate separation.

54. The method, according to claim 30, wherein the animal is a human.

* * * * *